US011288327B2

(12) United States Patent
Fanberg

(10) Patent No.: US 11,288,327 B2
(45) Date of Patent: Mar. 29, 2022

(54) USER CONFIGURABLE ELECTRONIC MEDICAL RECORDS BROWSER

(71) Applicant: Victor V. Fanberg, Dublin, OH (US)

(72) Inventor: Victor V. Fanberg, Dublin, OH (US)

(*) Notice: Subject to any disclaimer, the term of this patent is extended or adjusted under 35 U.S.C. 154(b) by 214 days.

(21) Appl. No.: 16/781,800

(22) Filed: Feb. 4, 2020

(65) Prior Publication Data

US 2020/0250242 A1    Aug. 6, 2020

Related U.S. Application Data

(60) Provisional application No. 62/918,580, filed on Feb. 5, 2019.

(51) Int. Cl.
| | |
|---|---|
| *G06F 16/93* | (2019.01) |
| *G06F 16/908* | (2019.01) |
| *G06K 9/00* | (2022.01) |
| *G16H 15/00* | (2018.01) |

(52) U.S. Cl.
CPC ............ *G06F 16/93* (2019.01); *G06F 16/908* (2019.01); *G06K 9/00463* (2013.01); *G16H 15/00* (2018.01)

(58) Field of Classification Search
CPC ...... G06F 16/93; G06F 16/907; G06F 16/908; G16H 15/00; G06K 9/00463
See application file for complete search history.

(56) References Cited

U.S. PATENT DOCUMENTS

2016/0092638 A1* 3/2016 Padmani ............... G16H 40/20
 705/2
2016/0321399 A1* 11/2016 Ramachandran ... G06F 16/9024

\* cited by examiner

*Primary Examiner* — Scott T Baderman
*Assistant Examiner* — Seung Woon Jung
(74) *Attorney, Agent, or Firm* — Standley Law Group LLP; Jeffrey S. Standley; Kenny W. Pung

(57) ABSTRACT

A method for displaying a plurality of documents on a screen. Each document of the plurality of documents defines a plurality of document criteria. The method includes: selecting a first document criterion and a second document criterion; storing and retrieving the first and second document criterion on a computer readable medium; filtering based on the first document criterion to yield a first plurality of filtered documents, each filtered document of the first plurality of filtered documents includes the first document criterion; filtering based on the second document criterion to yield a second plurality of filtered documents, each filtered document of the second plurality of filtered documents includes the second document criterion; generating a placeholder for each filtered document of the second plurality of filtered documents; and displaying the first plurality of filtered documents and each generated placeholder on a tab on the screen based on the date.

19 Claims, 37 Drawing Sheets

| Type of prompt | Example of data entry prompts from a data entry form | Example converted to pure text |
|---|---|---|
| Multi-select check boxes | Prompt ☒ Response 1<br>☐ Response 2<br>☒ Response 3 | Prompt: Response 1 \| Response 3 |
| Single select option groups | Prompt ● Response 1  ○ Response 2  ○ Response 3 | Prompt: Response 1 |
| Combo boxes, multi-select dropdown lists | Prompt [Response 1 / Response 2 / Response 3 ▼] | Prompt: Response 1 \| Response 3 |
| Free text boxes, edit boxes | Prompt [Response (free text)] | Prompt: Response (free text) |
| Likert groups | Prompt ● 1  ○ 2  ○ 3  ○ 4  ○ 5 | Prompt: 1 |
| Numeric | Prompt [1] | |
| Yes / No prompts | Prompt ● Yes  ○ No | Prompt: Yes |
| Date | Prompt [7/1/90] | Prompt: Jul 1, 1990 |
| Date with age | | Prompt: Jul 1, 1990 (Age: 29) |
| Individual check boxes | Prompt 1 ☒ Response 1<br>Prompt 2 ☐ Response 2<br>Prompt 3 ☒ Response 3<br>Response 4 ☒<br>☒ Response 5 | Prompt 1: Response 1<br>Prompt 3: Response 3<br>Response 4<br>Response 5 |

| LOCATION OF SERVICE (select one) | |
|---|---|
| ☐ school and child care (all ages through college) | ☒ temporary home (including friend or family homes, group homes, shelters, apartments, trailers, and other dwellings) |
| ☐ community center (e.g., recreation club) | ☐ IF A TEMPORARY HOME: PLEASE CHECK THIS BOX IF ANY CHILDREN UNDER AGE 18 LIVE IN THIS HOME. |
| ☐ provider site/mental health agency (agency involved with the CCP) | ☐ permanent home |
| ☐ workplace (workplace of the disaster survivor and/or first responder) | ☐ IF A PERMANENT HOME: PLEASE CHECK THIS BOX IF ANY CHILDREN UNDER AGE 18 LIVE IN THIS HOME. |
| ☐ disaster recovery center (e.g., Federal Emergency Management Agency [FEMA], American Red Cross) | ☐ phone counseling (15 minutes or longer) |
| ☐ place of worship (e.g., church, synagogue, mosque) | ☐ IF HOTLINE, HELPLINE, or CRISIS LINE, please check here. |
| ☐ retail (e.g., restaurant, mall, shopping center, store) | ☐ medical center (e.g., doctor, dentist, hospital, mental health specialty center) |
| ☐ public place/event (e.g., street, sidewalk, town square, fair, festival, sports) | ☐ other (specify in box) [_____] |

Prior art           308                    FIG. 4A 320   322   324

LOCATION OF SERVICE (select one): temporary home (including friend or family homes, group homes, shelters, apartments, trailers, and other dwellings)

FIG. 4B 340   340   340   340   350
                                352
1    10   20   30   40   50   60   70   354
|    |    |    |    |    |    |    |
LOCATION OF SERVICE (select one): temporary home (including friend or family homes, group
                                                    364            80
FIG. 4C                                             362            340
                                                    360

320  372  322           376              378
          374
LOCATION OF SERVICE (select one): temporary home (including friend or family homes...

FIG. 4D

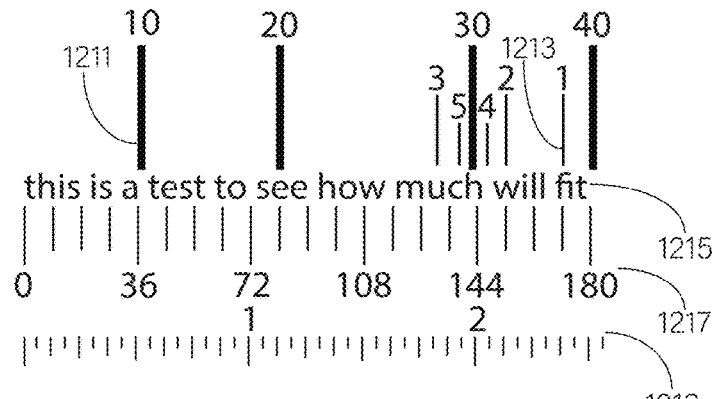
FIG. 15
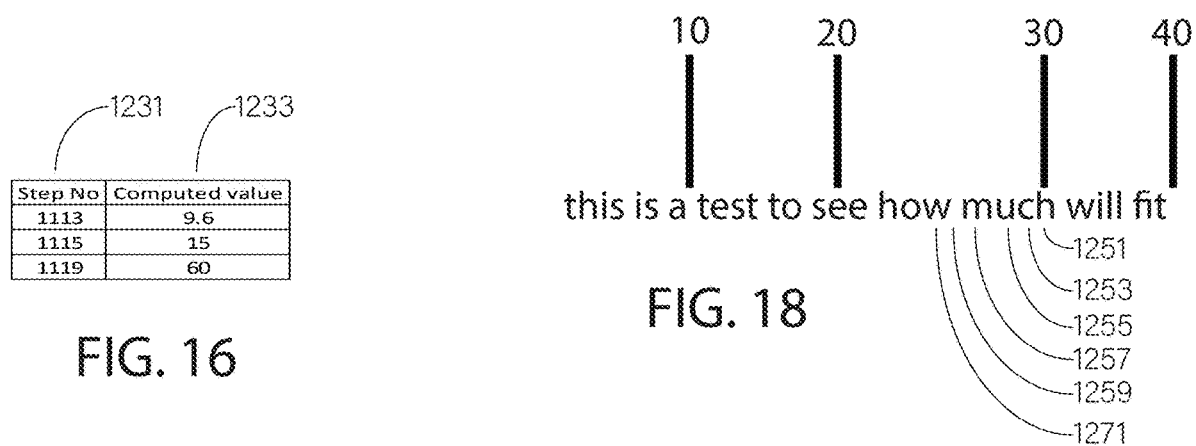
FIG. 16
FIG. 18
FIG. 17

FIG. 20

1401 — Personal Information Section:
1403 — Family Information:
1405 — Parent: Morris | Relationship: Father (1421) | Age: 62 (1423, 1425, 1427) | Occupation: Mechanical Engi (1429, 1431)
Education: 4 - Year Degree | Rel. Status: Married | Deceased? ○Yes ●No | If yes, date:
1407 —
Parent: Betty | Relationship: Mother | Age: 61 | Occupation: Retired
Education: High School | Rel. Status: Married | Deceased? ○Yes ●No | If yes, date:

1409 — Please provide the names and relationships of additional family members starting with step parents, siblings, spouse / partner, children.

1411 — Additional Family: | Relationship: | Age: | Occupation:
Education: | Rel. Status: | Deceased? ○Yes ○No | If yes, date:

Additional Family: | Relationship: | Age: | Occupation:
Education: | Rel. Status: | Deceased? ○Yes ○No | If yes, date:

1413 — Additional Family: | Relationship: | Age: | Occupation:
Education: | Rel. Status: | Deceased? ○Yes ○No | If yes, date:

Additional Family: | Relationship: | Age: | Occupation:
Education: | Rel. Status: | Deceased? ○Yes ○No | If yes, date:

Additional Family: | Relationship: | Age: | Occupation:
Education: | Rel. Status: | Deceased? ○Yes ○No | If yes, date:

1415 — Medical Information Section:
1417 — Medical / Psychological History

Chronic Health Concerns  ● Yes  ○ No    If yes, please describe:
1419 —                                    Ulcerative Colitis

FIG. 21

1401 — Personal Information Section:
1403 — Family Information:
1405 — Parent: Morris | Relationship: Father (1421, 1423) | Age: 62 (1425, 1427) | Occupation: Mechanical Engi (1429)
Education: 4 - Year Degree | Rel. Status: Married | Deceased? ○Yes ●No
1407 —
Parent: Betty | Relationship: Mother | Age: 61 | Occupation: Retired
Education: High School | Rel. Status: Married | Deceased? ○Yes ●No 1409 — Please provide the names and relationships of additional family members starting with step parents, siblings, spouse / partner, children.

1415 — Medical Information Section:
1417 — Medical / Psychological History

Chronic Health Concerns  ● Yes  ○ No    If yes, please describe:
1419 —                                    Ulcerative Colitis

| | Pass | Heading | Before Next heading | RecordType | After Next heading |
|---|---|---|---|---|---|
| 1501 | 3 | 1417 | #LookForNormalHeading | #NormalHeading | #LookForOtherHeading |
| 1503 | 4 | 1415 | #LookForOtherHeading | #OtherHeading | #LookForOtherHeading |
| | 45 | 1409 | #LookForNormalHeading | #NormalHeading | #LookForOtherHeading |
| | 62 | 1403 | #LookForNormalHeading | #NormalHeading | #LookForOtherHeading |
| 1505 | 63 | 1401 | #LookForOtherHeading | #OtherHeading | #LookForOtherHeading |

FIG. 22

Personal Information Section:

Family Information:

| | | | |
|---|---|---|---|
| Parent: Morris | Relationship: Father | Age: 62 | Occupation: Mechanical Engineer |
| Education: 4 - Year Degree | Rel. Status: Married | Deceased? No | |
| Parent: Betty | Relationship: Mother | Age: 61 | Occupation: Retired |
| Education: Some College | Rel. Status: Married | Deceased? No | |

Medical Information Section:
Medical / Psychological History

Chronic Health Concerns: Yes     If yes, please describe: Ulcerative Colitis

FIG. 23

```
#define RECTYPE "RecType"
#define REVERSEAPPTCNT "ReverseApptCnt"
#define LASTVIEWED "LastViewed"
#define RELEVANTDATE "RelevantDate"
#define ALLERGYRECTYPE "AL"
#define MEDLOG1 "ME"
#define MEDLOG2 "M2"                           2961
#define INCLUDE_ALLERGIES -3    ─────────
#define INCLUDE_RECENT_APPT -4      2965
#define INCLUDE_UNREAD -5    ─────────
#define INCLUDE_MEDLOG -6           2969
#define INCLUDE_MEDLOG_BY_DRUG -7  ─────
#define HIDE_BEFORE_APPT -8         2973
#define HIDE_NOT_VIEWED -9   ─────────
#define HIDE_VIEWED -10             2977
#define HIDE_OLDER -11   ─────────
#define EXCLUDE_NOT_VIEWED -12      2981
#define EXCLUDE_VIEWED -13   ─────────
#define EXCLUDE_OLDER -14           2985
define EXCLUDE_BEFORE_APPT -15  ───── switch (currNodeTagNo) {
    case INCLUDE_ALLERGIES:
        rtnVal = RECTYPE + "=" + ALLERGYRECTYPE; break;
    case INCLUDE_RECENT_APPT:
    case HIDE_BEFORE_APPT:
    case EXCLUDE_BEFORE_APPT:
        rtnVal = REVERSEAPPTCNT + " BETWEEN 1 AND " + ToString(Qty); break;
    case INCLUDE_UNREAD:
    case HIDE_NOT_VIEWED:
    case EXCLUDE_NOT_VIEWED:
        rtnVal = LASTVIEWED + " IS NULL"; break;
    case INCLUDE_MEDLOG:
        rtnVal = RECTYPE + "=" + MEDLOG1 ; break;
    case INCLUDE_MEDLOG_BY_DRUG:
        rtnVal = RECTYPE + "=" + MEDLOG2 ; break;
    case HIDE_VIEWED:
    case EXCLUDE_VIEWED:
        rtnVal = LASTVIEWED + " IS NOT NULL"; break;
    case HIDE_OLDER:
    case EXCLUDE_OLDER:
        rtnVal = RELEVANTDATE + "<" + ToString(Date); break;
}
```

FIG. 28D

Include
   ☐Appointments
      ☐Couples
         ☐Couples initial consultation    *APPT_TYPE: 201*
         ☐Couples therapy    *APPT_TYPE: 225*
      ☐Individual
         ☐Individual initial consultation    *APPT_TYPE: 157*
         ☐Individual therapy    *APPT_TYPE: 218*
      ☐Group
         ☐Group screening    *APPT_TYPE: 125*
         ☐Group therapy    *APPT_TYPE: 126*
      ☒Pyschiatry
         ☒Psychiatry initial contulation    *APPT_TYPE: 131*
         ☒Ongoing psychiatry    *APPT_TYPE: 140*
   ☐Authors
      ☒Psychiatry
         ☒Gladys Friday, M.D.    *STAFF: 225*
         ☒Don Key, D.O.    *STAFF: 218*
         ☒Page Turner, M.D.    *STAFF: 140*
      ☐Special
         ☐Client    *STAFF: 50*
         ☐EMR Generated    *STAFF: 51*
         ☐Other    *STAFF: 53*
      ☐Therapy
         ☐Dr. Rob Berry    *STAFF: 126*
         ☐Dr. Tim Burr    *STAFF: 300*
         ☐Dr. Kash Register    *STAFF: 301*
   ☐Casenote type
      ☐Brief walkin    *NOTE_TYPE: 289*
      ☐Initial paperwork    *NOTE_TYPE: 126*
      ☐Session notes    *NOTE_TYPE: 225*
      ☐Termination    *NOTE_TYPE: 201*
      ☐Test results    *NOTE_TYPE: 157*
   Other
      ☐Include all since last ~Qty~ appointments    *SPECIAL: -4*
      ☐Include everything unread    *SPECIAL: -5*
      ☐Include medications    *SPECIAL: -6*
      ☐Include medications in drug order    *SPECIAL: -7*

FIG. 29A

Hide
- ☐ Appointments
    - ☐ Couples
        - ☐ Couples initial consultation — *APPT_TYPE: 201*
        - ☐ Couples therapy — *APPT_TYPE: 225*
    - ☐ Individual
        - ☐ Individual initial consultation — *APPT_TYPE: 157*
        - ☐ Individual therapy — *APPT_TYPE: 218*
    - ☐ Group
        - ☐ Group screening — *APPT_TYPE: 125*
        - ☐ Group therapy — *APPT_TYPE: 126*
    - ☐ Pyschiatry
        - ☐ Psychiatry initial contulation — *APPT_TYPE: 131*
        - ☐ Ongoing psychiatry — *APPT_TYPE: 140*
- ☐ Authors
    - ☐ Psychiatry
        - ☐ Gladys Friday, M.D. — *STAFF: 225*
        - ☐ Don Key, D.O. — *STAFF: 218*
        - ☐ Page Turner, M.D. — *STAFF: 140*
    - ☐ Special
        - ☐ Client — *STAFF: 50*
        - ☐ EMR Generated — *STAFF: 51*
        - ☐ Other — *STAFF: 53*
    - ☐ Therapy
        - ☐ Dr. Rob Berry — *STAFF: 126*
        - ☐ Dr. Tim Burr — *STAFF: 300*
        - ☐ Dr. Kash Register — *STAFF: 301*
- ☐ Casenote type
    - ☐ Brief walkin — *NOTE_TYPE: 289*
    - ☐ Initial paperwork — *NOTE_TYPE: 126*
    - ☐ Session notes — *NOTE_TYPE: 225*
    - ☐ Termination — *NOTE_TYPE: 201*  ← 3301
    - ☒ Test results — *NOTE_TYPE: 157* ← 3303
- Other
    - ☐ Hide items more then ~Qty~ appointments old — *SPECIAL: -8*
    - ☐ Hide items not previously viewed — *SPECIAL: -9*
    - ☐ Hide items previously viewed — *SPECIAL: -10*
    - ☐ Hide items prior to ~Date~ — *SPECIAL: -11*

FIG. 29B

Exclude
- ☐ Appointments
  - ☐ Couples
    - ☐ Couples initial consultation — *APPT_TYPE: 201*
    - ☐ Couples therapy — *APPT_TYPE: 225*
  - ☐ Individual
    - ☐ Individual initial consultation — *APPT_TYPE: 157*
    - ☐ Individual therapy — *APPT_TYPE: 218*
  - ☐ Group
    - ☐ Group screening — *APPT_TYPE: 125*
    - ☐ Group therapy — *APPT_TYPE: 126*
  - ☐ Pyschiatry
    - ☐ Psychiatry initial contulation — *APPT_TYPE: 131*
    - ☐ Ongoing psychiatry — *APPT_TYPE: 140*
- ☐ Authors
  - ☐ Psychiatry
    - ☐ Gladys Friday, M.D. — *STAFF: 225*
    - ☐ Don Key, D.O. — *STAFF: 218*
    - ☐ Page Turner, M.D. — *STAFF: 140*
  - ☐ Special
    - ☐ Client — *STAFF: 50*
    - ☐ EMR Generated — *STAFF: 51*
    - ☐ Other — *STAFF: 53*
  - ☐ Therapy
    - ☐ Dr. Rob Berry — *STAFF: 126*
    - ☐ Dr. Tim Burr — *STAFF: 300*
    - ☐ Dr. Kash Register — *STAFF: 301*
- ☐ Casenote type
  - ☐ Brief walkin — *NOTE_TYPE: 289*
  - ☐ Initial paperwork — *NOTE_TYPE: 126*
  - ☐ Session notes — *NOTE_TYPE: 225*
  - ☐ Termination — *NOTE_TYPE: 201*
  - ☐ Test results — *NOTE_TYPE: 157*
- Other
  - ☐ Exclude items not previously viewed — *SPECIAL: -12*
  - 3801 ☐ Exclude items previously viewed — *SPECIAL: -13*
  - ☐ Exclude items prior to ~Date~ — *SPECIAL: -14*
  - ☒ Exclude items more than ~Qty~ appointments old — *SPECIAL: -15*  — 3803

FIG. 29C

```
SELECT *, CASE WHEN (NoteType) IN (157) THEN 1 ELSE 0 END AS IsHidden
FROM extractTable
WHERE (ApptType IN (131,140) OR StaffId IN (225,218,140))
    AND NOT (ReverseAppointmentCount > 4)
```

FIG. 30

USER CONFIGURABLE ELECTRONIC MEDICAL RECORDS BROWSER

CROSS-REFERENCE AND PRIORITY CLAIM

This application claims the benefit of U.S. Provisional Application No. 62/918,580 filed Feb. 5, 2019, which is incorporated by reference herein in its entirety.

FIELD

This application relates to methods of displaying a plurality of documents on a screen and, more particularly, displaying electronic medical records on a screen.

BACKGROUND

Record keeping in medical facilities has been migrating to electronic medical record systems (EMR) for the past several years. More and more medical offices, hospitals, college counseling centers, and other providers are now on EMRs. EMRs provide standardized formats to enter information such as electronic data forms and allow for universal retrieval in fractions of a second where old paper chart systems required much longer times to access information.

Traditional EMRs suffer from being designed around a computer model that silos information and expects the user to follow the way programmers expected the information to be presented. The problem stems from how the data is stored and that programmers have built their navigation systems around the silos of each piece of information in the EMR's database.

The EMR data is stored as records. EMR systems are written to present records with navigation steps necessary to move from one record to another and in the traditional EMR, typically with a requirement to close one record before viewing the next record of the same type (which requires an additional navigation step for each record).

The typical navigation steps of using a traditional EMR to review a client's chart involves the following pattern:
  Navigate to a client's master record (requires aiming a mouse aiming and clicking)
  Navigate to the client's chart (requires aiming a mouse aiming and clicking)
  Open the first note in the chart (requires aiming a mouse aiming and clicking)
  Read the document
  Open the first attachment (requires aiming a mouse aiming and clicking)
  Read the first attachment
  Close the first attachment (requires aiming a mouse aiming and clicking)
  Open the second attachment (requires aiming a mouse aiming and clicking)
  Read the second attachment
  Close the second attachment (requires aiming a mouse aiming and clicking)
  Close the first note (requires aiming a mouse aiming and clicking)
  Open the second note (requires aiming a mouse aiming and clicking)
  Read the document
  Open the first attachment (requires aiming a mouse aiming and clicking)
  Read the first attachment
  Close the first attachment (requires aiming a mouse aiming and clicking)
  Open the second attachment (requires aiming a mouse aiming and clicking)
  Read the second attachment
  Close the second attachment (requires aiming a mouse aiming and clicking)
  Close the second note (requires aiming a mouse aiming and clicking)

And so on for however many documents were in the chart and however many attachments were in each particular note. There could be hundreds of documents in a client's chart, so even though pointing a mouse and clicking is quick, the process adds up to fatigue on the user.

Often times it is hard for an EMR to predict exactly how much of a document needs to be presented to the user because different documents have different space requirements, so it often becomes a matter of having a small window or using the full screen without the user being able to choose, or if they can, again requiring navigation operations to set the window size each time. Once the full window mode is chosen, obviously, the window eventually has to be closed to navigate elsewhere in the EMR by another mouse aiming and clicking action.

Accordingly, those skilled in the art continue with research and development efforts in the field of EMR systems.

SUMMARY

Disclosed are methods for displaying a plurality of documents, especially documents related to electronic medical records, on a screen.

A method for displaying a plurality of documents on a screen. The plurality of documents include an electronic medical record. Each document of the plurality of documents defines a plurality of document criteria based on the substance of the documents. At least one document criterion of the plurality of document criteria includes a date. The screen includes a plurality of display tabs. The method includes: selecting a first document criterion; selecting a second document criterion; storing the first document criterion and the second document criterion on a computer readable medium; retrieving the first document criterion and the second document criterion from the computer readable medium; filtering the plurality of documents based on the first document criterion to yield a first plurality of filtered documents, wherein each filtered document of the first plurality of filtered documents includes a plurality of document criteria that includes the first document criterion; filtering the plurality of documents based on the second document criterion to yield a second plurality of filtered documents, wherein each filtered document of the second plurality of filtered documents includes a plurality of document criteria that includes the second document criterion; generating a placeholder for each filtered document of the second plurality of filtered documents; selecting a tab from the plurality of tabs; and displaying the first plurality of filtered documents and each generated placeholder on the tab in a sequential order that is based on the date for each document of the plurality of documents.

A method for selectively displaying elements from a plurality of documents on a screen. Each document of the plurality of documents includes at least one element. The elements include at least one of a title, a heading, a prompt, and a response related to a prompt, wherein each title, heading, prompt, and response defines a left boundary and a right boundary. The plurality of documents includes a first document that includes a prompt but no response. The plurality of documents further includes a second document that includes a prompt and a response. One of the left boundary of the prompt of the second document and the left boundary of the response of the second document is the furthest-left boundary. One of the right boundary of the prompt of the second document and the right boundary of the response of the second document is the furthest-right boundary. The furthest-left boundary and the furthest-right boundary collectively defines a pair of absolute boundaries. The method includes: reproducing the prompt of the second document to yield a reproduced prompt; converting the response of the second document into pure text to yield a converted response; combining the reproduced prompt and the converted response to form a prompt-response pair; and displaying the first document and the second document on the screen. The displaying includes replacing the prompt and the response of the second document with the prompt-response pair while remaining within the absolute boundaries. The displaying further includes excluding the prompt of the first document when displaying the first document on the screen.

A method for displaying a plurality of documents on a screen. The plurality of documents includes an electronic medical record. Each document of the plurality of documents defines a plurality of document criteria based on the substance of the documents. At least one document criterion of the plurality of document criteria includes a date. The screen includes a plurality of display tabs. The method includes: selecting a first document criterion; selecting a second document criterion; storing the first document criterion and the second document criterion on a computer readable medium; retrieving the first document criterion and the second document criterion from the computer readable medium; filtering the plurality of documents based on the first document criterion to yield a first plurality of filtered documents, wherein each filtered document of the first plurality of filtered documents includes a plurality of document criteria that includes the first document criterion, each filtered document of the first plurality of filtered documents further includes at least one of a prompt and a response related to a prompt, the first plurality of filtered documents includes a filtered document that includes a prompt but no response, the first plurality of filtered documents further includes a group of filtered documents, wherein each filtered document of the group of filtered documents includes at least one of a normal heading and a terminal heading, wherein the normal heading is followed by at least one of a prompt and a response, and wherein the terminal heading is followed by at least one of another terminal heading and the end of a filtered document of the group of filtered documents; identifying the normal headings and the terminal headings of the group of filtered documents; filtering the plurality of documents based on the second document criterion to yield a second plurality of filtered documents, wherein each filtered document of the second plurality of filtered documents includes a plurality of document criteria that includes the second document criterion; generating a placeholder for each filtered document of the second plurality of filtered documents; selecting a tab from the plurality of tabs; and displaying the first plurality of filtered documents and each generated placeholder on the tab in a sequential order that is based on the date for each document of the plurality of documents, wherein the displaying includes excluding the prompt of the filtered document, the normal headings of the group of filtered documents, and the terminal headings of the group of filtered documents from the display tab.

Other examples of the disclosed methods for displaying a plurality of documents on a screen will become apparent from the following detailed description, the accompanying drawings and the appended claims.

BRIEF DESCRIPTION OF THE DRAWINGS

FIG. 2 is a table summary depicting example methods of converting various types of prompts into pure text equivalents;

FIG. 4A is an example of a typical prompt-response field;

FIG. 4B is an example of a pure text conversion of the response field of FIG. 4A;

FIG. 4C is the pure text conversion of FIG. 4B as measured against an increasing count of characters;

FIG. 4D, is an example of the pure text conversion of FIG. 4B that has been shortened;

FIG. 15 is an example of a string of text being measured in accordance with the procedure of FIG. 13;

FIG. 16 is a table summary showing a number of different values calculated at various steps of the method of FIG. 13;

FIG. 17 is a table summary showing the calculated values at five different passes through the loop of FIG. 14 while processing the string of FIG. 15;

FIG. 18 is the string of text of FIG. 15 being processed through the loops of FIG. 12;

FIG. 20 is an example portion of a data entry form that will demonstrate removing an unused normal heading.

FIG. 21 is an example of how the portion of a data entry form of FIG. 20 may appear performing step 1309 the method of FIG. 19;

FIG. 22 is a table summary depicting the calculated values from the loop in 1307 of FIG. 19;

FIG. 23 is an example of how FIG. 20 may appear after being optimized in accordance with the method of FIG. 19;

FIG. 28D is pseudocode for an example method of generating SQL clauses from leaf nodes when the tag property of the leaf node for special cases is the single integer value currNodeTagNo;

FIG. 29A is an example of a simple Include configuration tree;

FIG. 29B is an example of a hide configuration tree;

FIG. 29C is an example of an exclude configuration tree

FIG. 30 is an example of a SQL generated for the configuration trees of FIGS. 29A-29D using the methods of FIGS. 27A and 27B, and FIGS. 28A-28D.

DEFINITIONS

Figure 1:
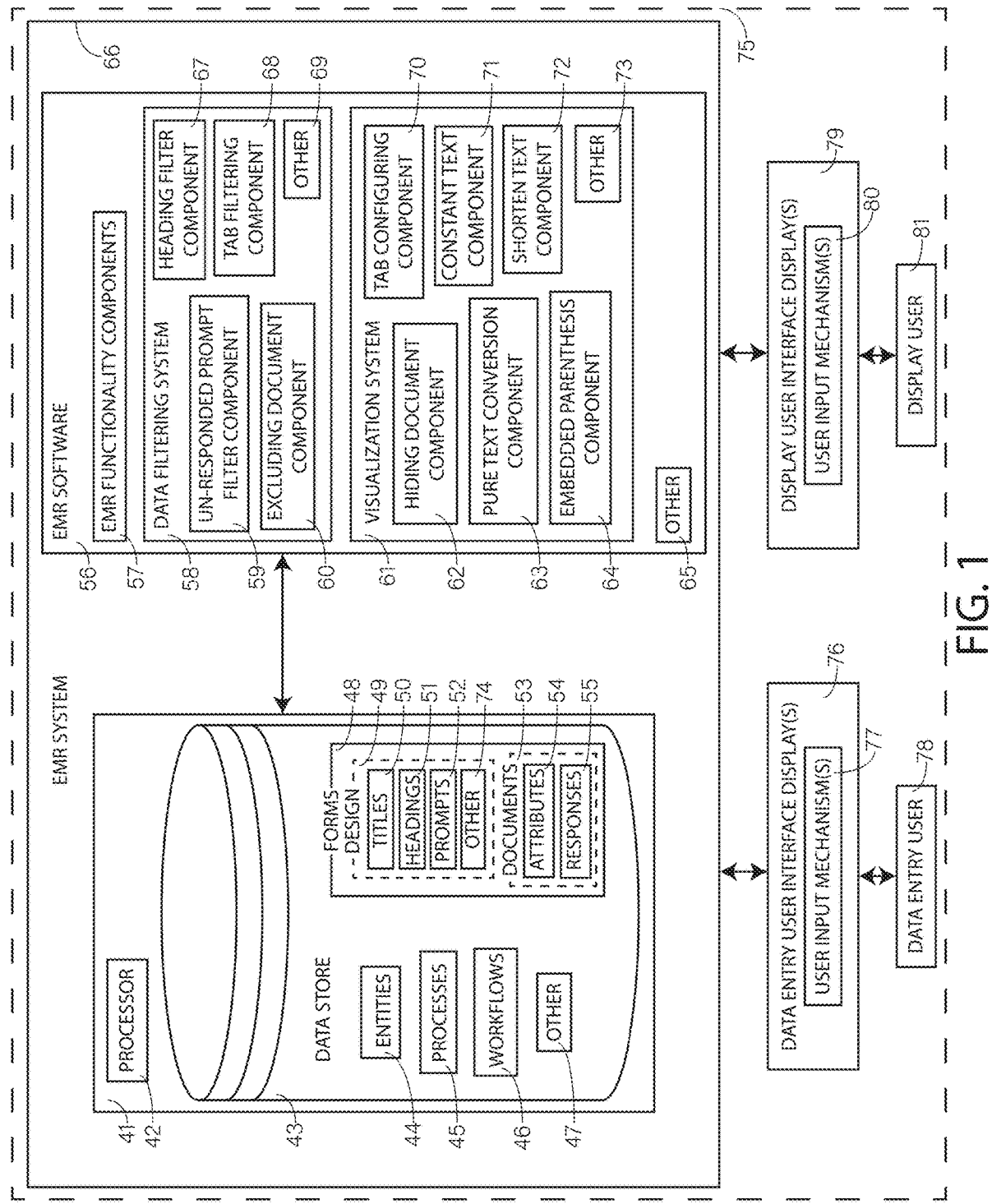
FIG. 1 is a block diagram of one example computer system.

"Attribute": the property of an entity, generally the formatting of the font and paragraph styles for titles, headings, prompts, responses, prompt-response pairs, combining string and concatenation string, but may also be such properties as whether a document is visible. The value of an attribute may be user definable.

"Combining string": the characters inserted between a prompt and a response to separate the two from each other. It may be user definable and can be such values as a colon and/or any other single character or multiple characters. A combining string cannot include any character which forces a new line every time the concatenation string is used, such as line feed ASCII character hexadecimal OA or carriage return ASCII character hexadecimal OD.

"Complete document": a document as it was initially presented to the data entry user, with every field available for the data entry user to enter data into. So, there is the potential to provide an answer to every question in a complete document. Not every completed document in an EMR may be a complete document, there may be some documents where individual questions are skipped or complete sections of the document are skipped.

"Concatenation string": the characters inserted between multiple responses to the same prompt to separate them from each other. It may be user definable and can be such values as NULL, a space, colon, any other single character or multiple characters. A concatenation string cannot include any character which forces a new line every time the concatenation string is used, such as line feed ASCII character hexadecimal OA or carriage return ASCII character hexadecimal OD.

"Data entry user": the user who responded to prompts in the computer typically using keyboard, mouse, touchscreen and like devices where the results of such input was stored back to the response field of the EMR. It is possible for the data entry user to be a system process or other such non-human data source.

"Data form": a method of controlling the structure of information entered by a data entry user where the data entry user is presented prompts for specific pieces of information and is often limited as the format of the responses they can provide. The design of data forms may be stored in the EMR data store as titles, headings, prompts and restrictions on responses. Then each instance of response may be stored with a reference pointer back to the design for the corresponding prompt.

"Display user": the user who looks up or reads information from the EMR, but whose records of which keystrokes, clicks or touches does not update the database with information specifically updating responses.

"Document": A named structural entity that can be stored, retrieved and exchanged among portions of the EMR and users as a separate entity. Some examples of documents may include, but are not limited to allergy records, appointments, case notes, client information, data forms, diagnoses, client flags, medication histories, staff details, and vital signs.

"Document criteria": a column in a document table that indicates the current row should be included in rows selected by a query. For example, a document criteria may include: record type (one of the values: allergies, appointments, case notes, client information, data forms, DSM-IV, DSM-V, client flags, medication, staff and vital signs), reverse appointment count (Sequential numbers for appointments this record is related to by date, starting at 1 for most recent appointment), viewed date, flag indicating appointment was attended, relevant date of document, appointment type id, case note type id, relevant staff member id, secondary relevant staff member id, data form id.

"EMR": abbreviation for electronic medical records.

"Exclude": to remove from being displayed.

"Heading": text on a data form where the data entry user cannot be prompted to enter any information because there is no associated response field and it is not the title of the data form. "Normal headings" are headings with a prompt that immediately follows the heading in a complete document. "Terminal headings" are headings where either no prompts appear below the heading or another terminal heading appears below the heading. "Other headings" are all other headings.

"Image": a response that cannot be altered to reduce the amount of space it occupies in the display of the EMR by an automated means other than scaling the complete response size, or by creating a link the displays the image when a display user activates that link thereby hiding portions of the EMR display screen. An image that is converted to a textual form, such as by using OCR, may itself be considered a data form with headings, prompts and responses and possibly a title, if the EMR is programmed to recognize which characters in the OCR image are values distinct for the client and which characters represent individual prompts and headings.

"Pointer": a variable that holds the address of a data object.

"Placeholder": any character or combination of characters inserted into the text that a data entry user would not be expected to type, such as "~1~", or certain control characters, etc. that will eventually be replaced with another character string. It can also be a substitute character that a user would accept as a replacement for some other character, such as using a square bracket (e.g., "[") as a substitute for a rounded parenthesis (e.g., "(") where the square bracket will later be changed to the corresponding parenthesis.

"Procedure": a block of code that is executed. As used in the present disclosure, "procedure" is used interchangeably with function, process and step.

"Prompt": text on a data form where the data entry user is prompted to enter information. The prompt object contains restrictions that controls what the response attribute and data type information and values that are valid to place in the response. When the word is used in association with the words "title", "heading" or "response", it generally means just the text of the prompt.

"Relevant date": a date that is significant to a document or data form. It may be such values as the date of an appointment, the date when the record was entered or updated or the creation date of the record.

"Response": values that the data entry user responded to when prompted on the screen to enter information. Response values are generally stored away from the form design elements with only a reference back to the prompt design element associated with the response. Responses may include, but are not limited to, text values, numeric values, date and time values, geography values, money values and Boolean values.

"Tab": a visible structure with a caption with a hotspot and an associated content view page(s), that allows a user to press on the caption and have the view being displayed switch to the associated content indicated by the tab, wherein the page(s) primarily comprises documents from an EMR. If there are multiple pages, pressing on the caption hotspot will either select the first page in the set of pages or the last page viewed for the set of pages.

"Terminal heading": a heading that follows the final prompt in a document (e.g., a data form).

"Title": a name that identifies the data form design. As used in the present disclosure, a title may appear on the first line of each data form to distinguish that data form from the previous and may have the relevant date appended to the field.

DETAILED DESCRIPTION

The invention of the present disclosure is a method of browsing documents in an EMR environment that has the advantages of (1) fitting more relevant information on the screen at one time with (2) fewer distractions to slow down the user's comprehension of the information on the screen and (3) quicker navigation through the client's chart. The invention is executable on a desktop or handheld computer in an EMR server environment. The communication between the computer and server is likely, at least partially, through the local area network.

In one example, the invention may be configured to fit more relevant information on a screen by using a creative way to utilize what was previously blank, unusable space on the screen. As will be shown further below, the invention can often reduce the amount of space required to present many prompt-response pairs to a user by a line or more. The more lines that are removed, the more information from further down the data form that used to be off the bottom of the screen becomes visible. Therefore more information is on the screen at a time and fewer navigation operations are required to obtain information from data forms.

In another example, the invention may be configured to eliminate elements on a screen that can programmatically be determine to be insignificant. As will be discussed further below, methods of removing insignificant elements may include, for example, (1) not presenting data to a display user in the same format as it was originally presented to the data entry user, where unselected options do not need to be presented back to the display user; (2) eliminating headings when sections they introduce were skipped by the data entry user; (3) removing certain pre-defined constant text that is presented on the screen as a flag for maintaining forms but are useless and distracting to the display user; (4) shortening certain text to be no more than a pre-specified length, while avoiding shortening text typed by the data entry user; (5) removing embedded parenthetical comments, again while avoiding removing anything from text typed by the data entry user; (6) removing unnecessary lines and other visual distractions.

In yet another example, the invention may include a method for converting records stored in an EMR into what resembles tabs of an internet navigation browser, with the user in full dynamic control of the criteria that selects which documents will appear on each page of the browser and the capability to store the configuration settings of each tab. This allows the display user to further customize which information will be displayed and scroll through rather than navigate with mouse clicks for each individual record, opening and closing each before moving on to the next.

The invention may improve the space utilization of the screen so that more lines of information fits on the screen at a time when displaying data forms. This has an advantage when browsing the screen to review a client's chart, as there are fewer navigation operations necessary because more information was on the screen at a time.

Without being bound by any particular theory, it is believed that by formatting the prompt and response different from each other, the human eye is more quickly able to distinguish the responses, and therefore able to more assimilate and use the information.

It is generally contemplated that displaying a prompt that has not been answered serves only to distract the display viewer's eyes when trying to quickly digest the information on the display screen and can add to the amount of scrolling necessary to view all the information on a data form.

Additionally, some prompts, headings or titles are excessively long. For example, a terms of service disclosure form can go on for pages with little need for a display user to view the details. It is generally contemplated that once a display user is familiar with information on the data form, the display user should be able to recognize the information on the data form without seeing more than the start of the prompt.

Additionally, it is further contemplated that if a data entry user skips a section, there is generally no reason to display the heading on the display, thereby further saving vertical space.

Those skilled in the art will appreciate that in an EMR, there is certain information that one generally does not want to view. For example, if a client fills out a data form with their responses to a scored assessment instrument, it is likely that the display user would want to view only the scored results, not the individual responses the client filled in.

Depicted in FIG. 1 is a block diagram of one non-limiting example of an enterprise computing system 75. This system 75 includes an EMR system 66 and a database server 41. EMR system 66 illustratively generates one or more data entry user interface displays 76, 79 by using user input mechanisms 77, 80 to interact with a data entry user 78 and/or a display user 81. Nothing herein is meant to imply the user input mechanisms 77 and 80 are necessarily different devices. To the contrary, they may be the same user input mechanisms, just being used at different times and these times may be separated only by a fraction of the second. Display user 81 may interact with user input mechanisms 80 to control and manipulate EMR system 66. The display user may also be the same individual as the data entry user, just at a different time, also where the time could be as small as a fraction of a second. In one embodiment, the individual may change from a display user 81 into a data entry user 78 by activating a data entry mode, and change back by deactivating the data entry mode. The same individual may also perform a different job function at different times.

EMR system 66 further includes database server 41 and EMR Software 56. The database server includes a database processor 42, and a data store 43. Data store 43 may store, for example, entities 44, processes 45, workflows 46, forms 48, and other EMR system records and/or data 47. Forms 48 may further be divided into form design 49 and form documents 53 to store responses 55 that may be submitted by a data entry user 78. Form design 49 may further be divided into titles 50, headings 51, prompts 52 and other items 74 such as lines and extra blank space. Data store 43 stores the data associated with the EMR system 66. Further, EMR Software 56 may include, among other items 65, EMR functionality components 57, data filtering system 58, visualization system 61, and the like.

Entities 44 illustratively represent various entities that may be defined within the EMR system 66. A client entity may describe and define a client. An appointment entity may describe and define an appointment. A staff entity may describe and define a therapist, medical doctor, and/or front desk work. A client file entity may describe and define a history of documents, lab reports, evaluations, medications supplied, allergies, and so forth. Those skilled in the art will appreciate that this is a non-limiting set of example entities, and that a wide variety of other entities may also be used without departing from the scope of the present disclosure. In addition, while the present discussion proceeds with respect to some EMR system records being described as entities, they can be other types of EMR system records as well.

Forms 48 illustratively represents various data (e.g., form designs 49 and form documents 53) within data store 43, and may be used as a mechanism by which to present the data on a user interface display 76, 79 to a data entry user 78 and/or a display user 81. In some examples, forms 48 may include entities 44 and other data records, and may also include a wide variety of controls, such as text fields, buttons, check boxes, links, icons, navigation elements, etc.

EMR system functionality components 57 illustratively runs various processes 45 and workflows 46, using the data stored in data store 43, to enable a data entry user 78 and/or a display user 81 to perform tasks on the EMR system 66. These EMR system functionality components 57 may be selectively chosen based on the needs of any particular organization deploying the EMR system 66. For example, if the EMR system 66 is being deployed by a medical office, EMR functionality components 57 that may be necessary or otherwise useful for such an organization may include scheduling applications, inventory tracking applications, external provider interaction applications, various audit tracking applications, and the like.

Data filtering system 58 illustratively includes un-responded prompt filter component 59, excluding document component 60, heading filter component 67, tab filtering component 68, and other items 69 as well (e.g., document criteria). Un-responded prompt filter component 59 may provide and control a process that removes prompts 52 from the data that is returned from the data store 43 during instances when the data entry user 78 did not respond to a prompt 52. Excluding document component 60 may remove whole documents 53 from data returned from the data store 43 that contains specific document attributes 54. Heading filter component 67 may analyze documents 53 to find and remove certain headings in their entirety from documents 53. Tab filtering component 68 may select which documents 53 will be included on a tab based on document attributes 54.

Visualization system 61 may generate user interface displays 76, either by itself, or under the control of other items in EMR system 66, and may include a hiding document component 62, a pure text conversion component 63, an embedded parenthesis component 64, a tab configuring component 70, a constant text component 71, a shorten text component 72, and other items 73 as well. The hiding document component 62 may select which documents 53, amongst the documents 53 that have already been selected, will be visible on a tab based on document attributes 54. The pure text conversion component 63 may change prompts 52 and their respective responses 55 into a text format wherein the characters are more efficiently positioned on the screen, such that more text may appear on a single page of the screen compared to previously available systems. The pure text conversion component 63 may exclude everything except titles 50, headings 51, prompts 52 and responses 55, so that other items 74 (e.g. extra lines and spacing) do not appear on the page even if the other items 74 are encoded into the form design 49. The embedded parenthesis component 64 may exclude from the data returned from the data store 43, the characters between parentheses in headings 51, prompts 52, and certain responses 55 depending on the document attributes 54 of the responses 55. The tab configuring component 70 may select which attributes 54 will be active to choose documents 53 to include, hide and exclude from tabs. The constant text component 71 may exclude from the data returned from the data store 43 pre-specified strings from headings 51, prompts 52 and certain responses 55. The shorten text component 72 may trim from data returned from the data store 43 any text beyond a pre-specified maximum length from headings 51, prompts 52 and certain responses 55.

Referring to FIG. 2, an example of a full and partial user interface displays 79 will now be described. As shown, a summary table 100 may demonstrate how most common types of prompts and responses may be converted into pure text. The left column of the summary table 100 provides a name of the prompt (e.g. response layout). The middle column of the summary table 100 shows how the prompt response might appear to a data entry user after the data entry user has completed answering the prompt. In each case, the word "Prompt" followed by a suitable arrangement of responses (such as any ones the ones shown) may appear where the prompt 52 would have appeared. The right column of the summary table 100 shows one example of how the prompt and response fields might appear in pure text. In this column, the prompt is shown in regular text and the response in bold text, the combining string is a colon (":") followed by a space, and the concatenation string is a space followed by a vertical bar ("|") followed by a space.

The fonts (boldness, italics, color, etc.) and paragraph characteristics (indentation, hanging indents, line spacing, paragraph spacing, etc) for each type of field (title, heading, prompt and response), the combining string and the concatenation string are typically options set by the user, any may vary without departing from the scope of the present disclosure.

Multi-select check boxes 102 may be converted to pure text by presenting the prompt (in the user defined prompt attributes), followed by the combining string, then each selected response (in the user defined response attributes) with the concatenation string between them.

Single select option groups 104 may be converted to pure text by presenting prompt (in the user defined prompt attributes), followed by the combining string, then the selected response (in the user defined response attributes).

Combo boxes differ only from multi-select dropdown lists 106 in that the latter allows selecting multiple answers. However, it is possible to answer a multi-select dropdown list 106 as if it is just a combo box by only selecting one answer. Combo boxes and multi-select dropdown lists 106 may be converted into pure text by presenting the prompt (in the user defined prompt attributes), followed by the combining string, then each selected response (in the user defined response attributes) with the concatenation string between them. If there is only one selected response, then there would be no concatenation string.

Free text boxes 108 differ only from edit boxes in the length of the expected response. Free text boxes 108 and edit boxes may be converted into pure text by presenting the prompt (in the user defined prompt attributes), followed by the combining string, then the text of the response (in the user defined response attributes).

Likert groups and numeric fields 110 are two example methods of selecting numbers. Likert groups and numeric fields 110 may be converted into pure text by presenting the prompt (in the user defined prompt attributes), followed by the combining string, then the number (in the user defined response attributes).

Yes/No fields 112 may be converted to pure text by presenting the prompt (in the user defined prompt attributes), followed by the combining string, then the selected value (in the user defined response attributes).

Dates may be entered into the prompt in many different formats (e.g., standard date 114, "7/1/1990," "07/01/90," "July 1, 90," etc.). To show a date in pure text, the same prompt (in the user defined prompt attributes), may be followed by the combining string, the date (in the user defined response attributes) using whatever date format the user has selected for dates (for example, by an operating system setting).

It is also possible to have a field that includes generated information as part of the response, such as a date with age calculation 116 that uses the identical formatting for the fields. In this case, square parentheses may be used (e.g., in one or more embodiments) in accordance with one or more optimizations that may exclude characters within parenthetical comments (discussed below). This is because square parentheses will not be recognized as the usual curved parentheses. If rounded parentheses are desired in the final display, it may be possible to use a placeholder (such as a square parenthesis) for the rounded parenthesis during the conversion into pure text. The other processing (such as excluding characters within parenthesis from all non-user typed text) may then be performed before finally converting all the placeholders to rounded parentheses. In other examples, the field may be evaluated to determine if the field is a computed field (as shown) before removing parenthetical comments, and if so, it skips removing the parenthetical comments.

Individual check boxes 118 may be converted into pure text by displaying the prompt in prompt format, followed by the combining sting, then the response in response format. If there are more than one individual check boxs, then each check box may have its own prompt and response fields.

In one or more examples, it is also possible to have an individual check box without a prompt 126, which may correspond to the pure text conversion 120 shown. A field with response following checkbox without a prompt 124 may have an identical pure text conversion 122. There will always be a response field when there is a check box, even if there is no prompt. If there is no prompt, there is no need to have a combining string and there is nothing to format in the user defined prompt attributes. The response is still formatted using the user defined response attributes.

Figure 3A:
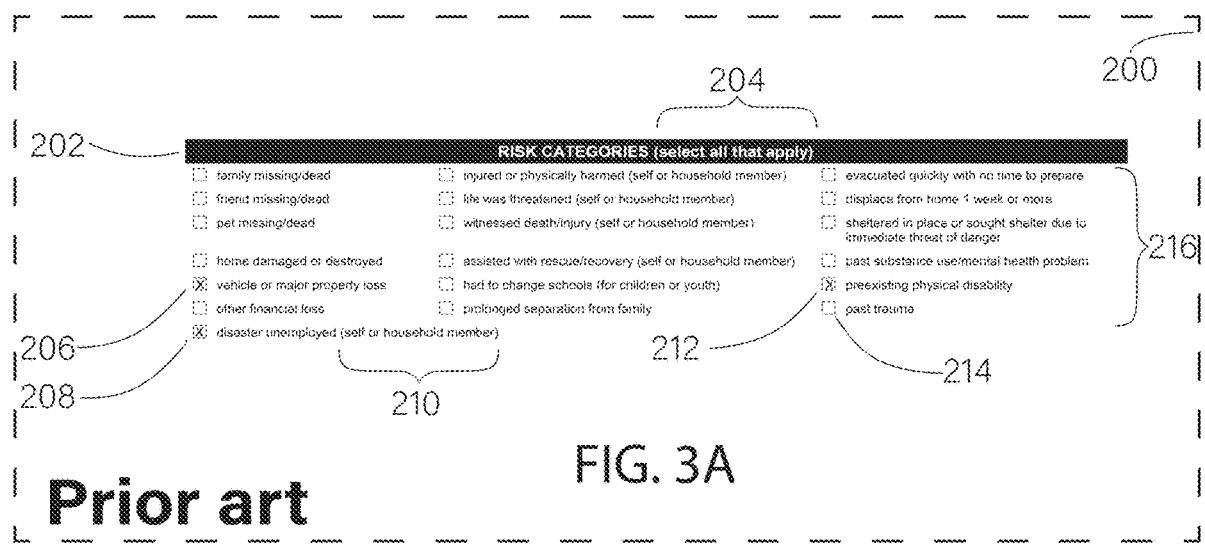
FIG. 3A is an example of a typical multi-select check box.

FIG. 3A depicts an example of how a typical EMR would display a multi-select checkbox 200 prompt response question and answer to a data entry user and/or a display user. The multi-select checkbox 200 has a prompt 202 with parenthetical comment 204 "(select all that apply)," and 19 responses available in the response area 216. In a typical display user interface display, both the prompt 202 and response area 216 would be shown as displayed in FIG. 3A (e.g., identical to the data entry user interface). In this example, there are three selected items (206, 208, and 212) chosen by the data entry user and multiple unselected options (e.g., 214). A parenthetical comment 210 is shown in the response area. The total height of the prompt 202 and response area 216 in this format is 9 lines.

Figure 3B:
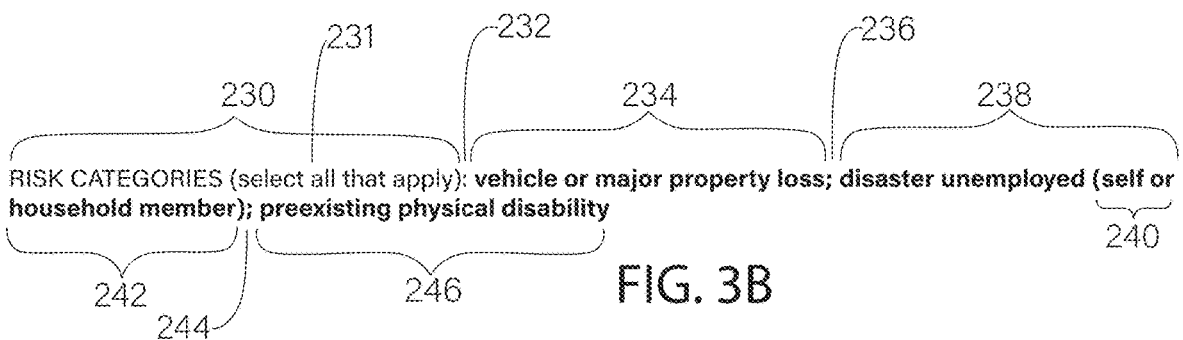
FIG. 3B is a first example of a pure text conversion of the multi-select check box of FIG. 3A.

FIG. 3B shows an embodiment of a conversion to pure text, converting the 9-line display of 3A into just 2 lines of pure text. The prompt 202 has been converted to pure text 230 by converting the text of 202 into pure text and applying the user defined prompt attributes to format the pure text prompt 230, adding the combining string 232, adding the first response 234 with the user defined response attributes plus the concatenation string 236, then the second response 238 similarly formatted plus the concatenation string 244, then the third response 246 similarly formatted.

Notably, the parenthetical comment 204 in FIG. 3A may be retained in the prompt 230 of the full text conversion of FIG. 3B. These parenthetical comments may be employed to provide instructions that may assist/instruct the data entry user in responding to the prompt. Other examples of such instructions may include, for example "(select the top 3 responses)" or "(include subjective and objective info)". These instructions can be excluded from the prompt without changing the meaning of the prompt, especially if the display user is familiar with the data form as presented to the data entry user. Fewer words on the screen means there will be fewer distractions on the screen to slow the eye from discerning the important information on the screen. Without being bound by any particular theory, it is believed that this conciseness helps to attract the user's eye to the response rather than the prompt. In other embodiments, lines may also be dropped from the display user's 81 screen.

There is also a parenthetical comment (240 plus 242) in the second response (238 plus 242). Parenthetical comments within responses typically help a data entry user 78 discern the bounds of the option by further defining the response. But if a display user 81 is familiar with the data form presented to the data entry user 78, the parenthetical comment can be excluded from the response for the display user 81. If the parentheses are not something that the user typed or is in a format that includes some system generated information (such as an age in a date with age calculation 116 field). Furthermore, if a form designer knows that a display user 81 will need to see any parenthetical information, the form designer can avoid triggering automatic parenthetical information exclusion by using a placeholder character for the parenthesis.

Figure 3C:
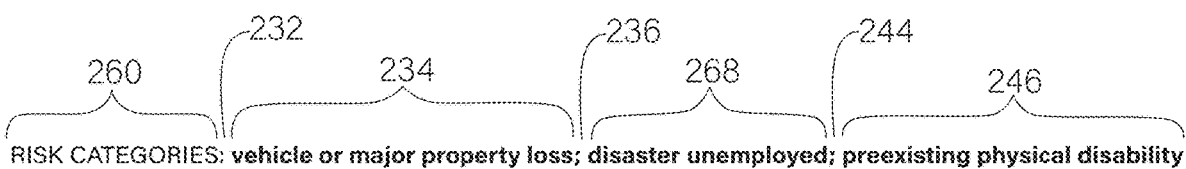
FIG. 3C is a second example of a pure text conversion of the multi-select check box of FIG. 3A excluding parenthetical comments within fields.

FIG. 3C shows another pure text conversion of FIG. 3A but excluding parenthetical comments. In doing so, the same prompt response sequence may be shorted by an additional line, depending on the user defined attributes and the screen size. The prompt 260 is created by deleting the parenthetical comment 204. Similarly, the response 268 is created by deleting parenthetical comment 210. In one or more examples, a marker may also be left in the field to indicate to the display user 81 that a parenthetical comment had been excluded, such as using "RISK CATEGORIES ( )" for prompt 260.

FIG. 4A depicts an example of a common prompt and response field. Included are the prompt 302, selected item 304 and unselected option 308 (which may be representative of other unselected options). Ideally, a response 306 may be enhanced by changing the wording slightly to take full advantage of the current text, such as by rewording the text as "temporary home with minor children (check this box for a temporary home with children under age 18 in the home)". Of course, in doing so, it is generally contemplated that appropriate checks/protocols should also be in place to ensure that the new prompt completely reflects the intention of the original prompt.

FIG. 4B shows a pure text conversion of the information shown in FIG. 4A. The prompt 320 of the pure text conversion is calculated from the original prompt 302 by adding the user defined prompt attributes with the combining string 322 and response 324. The response 324 was created from the selected item 304 by adding the user defined response attributes. In doing so, the approximately twelve lines of FIG. 4A was shortened to two lines, thereby requiring significantly less scrolling to read the client chart.

FIG. 4C illustrates how to calculate the longest string of full words without going beyond the predetermined maximum length of characters. This illustration is based only on the length of the pure text. The same principle can be applied to when the base string is some other field (e.g., a heading string, a prompt string or a response string). Those skilled in the art will appreciate that this may be particularly desirable for heading strings since they are known to include long, often undesirable (from the perspective of the user) sections of text (e.g., legal disclosures) that correlates to proportionately long, often undesirable scrolling to read the client chart.

FIG. 4C shows a count of characters 340 from the first character of the prompt. As shown, the $82^{nd}$ character is an "s", the $83^{rd}$ character is a comma, and the $84^{th}$ character is a space following the word "homes" (e.g., ref. nos. 354, 352, and 350, respectively). If the pre-determined length is eighty-three characters, then the longest string of full words may be calculated by first looking at the $84^{th}$ character 350 in search of an alphanumeric character. Since neither the $84^{th}$ character 350 nor the $83^{rd}$ character 352 are alphanumeric, the process turns to the $82^{nd}$ character 354, which is alphanumeric, to determine where the pure text string should be trimmed before adding an ellipse.

By way of example, if the pre-determined length was 70 characters, the process would start by looking at the $71^{st}$ character 360, which is an alphanumeric character ("f"). Since, at this point, there is no indication that the $71^{st}$ character 360 is the last character of the word, the process works backwards along the pure text string until the last character of a word is found. In the example shown, the $70^{th}$ character 362 is a space and the $69^{th}$ character 364 is an alphanumeric character. Thus, when the process reaches the $70^{th}$ character 362 and sees a space, the process may then switch to looking for the next alphanumeric character (e.g., the $69^{th}$ character 364) which should be the last character of a word. At which point, the pure text string may be trimmed.

FIG. 4D shows the final pure text of the prompt 320 and combining string 322 of FIG. 4B that is generated as a result of trimming based only on length. Trimmed response 376 is what remains of the response 324 after it has been trimmed. An ellipse 378 is appended to the end of the trimmed response 376. In this specific case, however, a shorter pure text string may also have been calculated by excluding parenthetical comments prior to applying the trimming because no trimming would have been required.

Figure 5A:
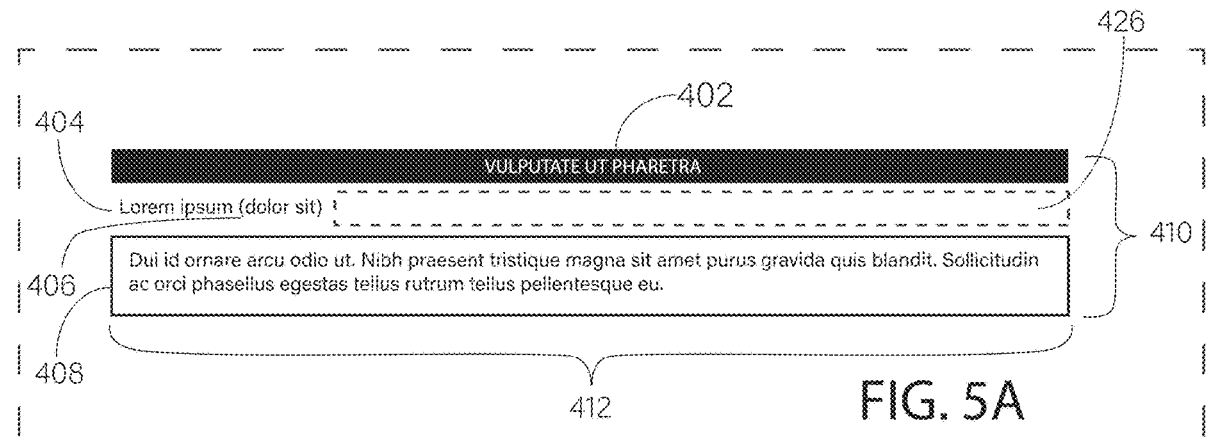
FIG. 5A is an example of a typical prompt-response field where the prompt is on a separate line from the response.
Figure 5B:
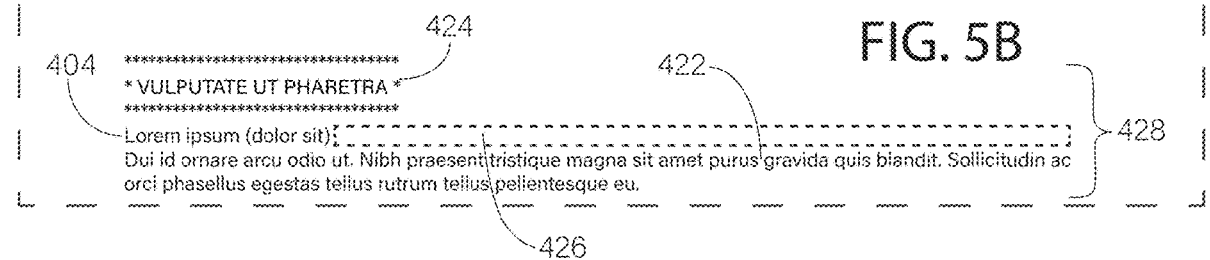
FIG. 5B is an example of what a user may see after completing the response of FIG. 5A.
Figure 5C:
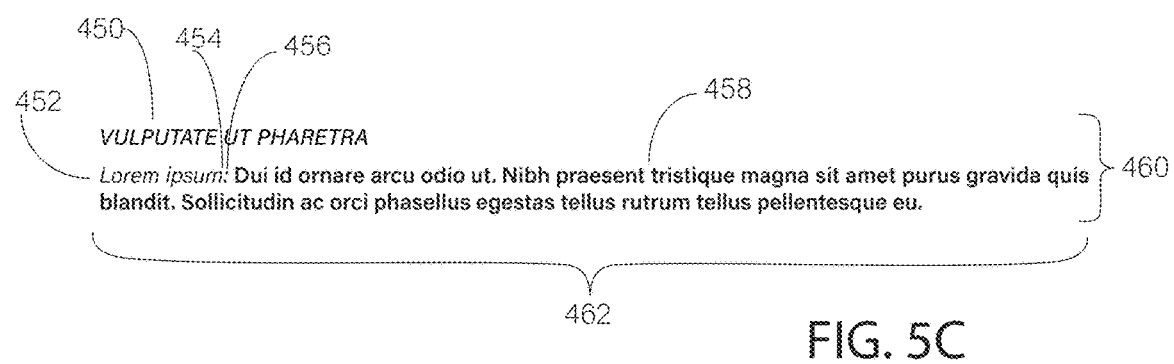
FIG. 5C, is an example of an optimized pure text conversion of the prompt-response field of FIG. 5A.

FIGS. 5A and 5B depict examples of what a data entry user and/or a display user may see before and after completing the response using existing EMR systems. Referring specifically to FIG. 5A, the prompt-response field includes a heading 402, a prompt 404 and a response 408. The prompt 404, may also include a parenthetical comment 406. The total height 410 and total width 412 of prompt-response field may be largely dependent on the heights and widths of the heading 402, prompt 404 and response 408 as shown. Referring specifically to FIG. 5B, a typical print out from an EMR is shown (e.g., as a display user might see it). The printout includes a heading 424, a prompt 404, and a response 422. The total height 428 of this prompt-response field is 4 lines even though heading 424 is identical to the data entry user's heading 402. Thus, in this example, the prompt-response field that is presented to a data entry user 78 may be shorter than what is presented to the display user 81. FIG. 5C depicts an embodiment of a pure text line that may be generated from the data shown in FIGS. 5A and 5B using the process of the present invention.

Notably, the prompt-response field shown in FIGS. 5A and 5B includes unused space 426 defined by the blank areas proximate (e.g., at or near) the lines of text. Those skilled in the art will appreciate that unused space 426 may be representative of other areas of unused space common to most data presentation formats (be it for EMR documents or otherwise). By employing the process of the present invention, it is possible to utilize the unused space 426, often saving at least one line of text to fully reproduce the answer.

Further, in one or more examples, the process may also be employed to find text that can generally be excluded safely with minimal impact on the completeness of the information presented on the screen. Since, in the English language, parenthetical comments are generally employed to explain, clarify or qualify something, it is generally contemplated that leaving out the parenthetical comments that are part of the basic data form should still present a substantially complete data form to a data entry user 78 and/or a display user 81 who is familiar with the form from prior use.

On the other hand, not all parenthetical comments can be omitted. If the data entry user 78 typed the parenthetical comment, the parenthetical comment must be left in because it explains, clarifies, or qualifies something the data entry user 78 wanted to communicate to the display user 81. Secondly, there may also be some computer-generated information that the format may use parentheses, such as a date with age calculation 116 field, day of week calculation, etc. Care must be taken to not exclude these parenthetical comments of calculated fields.

Referring to FIG. 5C, heading 450 is computed from heading 402 by applying the user defined heading attributes for font and paragraph. Prompt 452 is what remains of the prompt 404 after excluding the parenthetical comment 406 at the point where the parenthesis began 454. The output string continues with the user defined combining string 456. The response 458 is the response 408 with the user defined response attributes. Notably, the total height 460 of the pure text version is at least one line less than the height 410 of the prompt-response field presented to the data entry user or the height of a printout 428 because it made use of the previously unused space 426. The total width 462 of the pure text version may fill the same percentage of the page that the original total width 412 did.

Figure 6A:
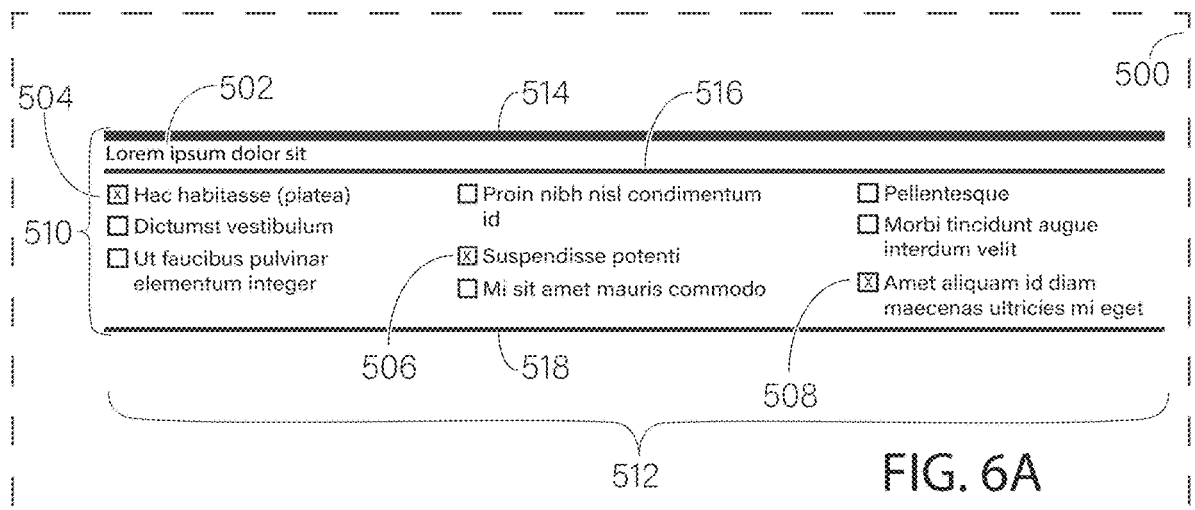
FIG. 6A is an example of a typical multi-select text box.
Figure 6B:
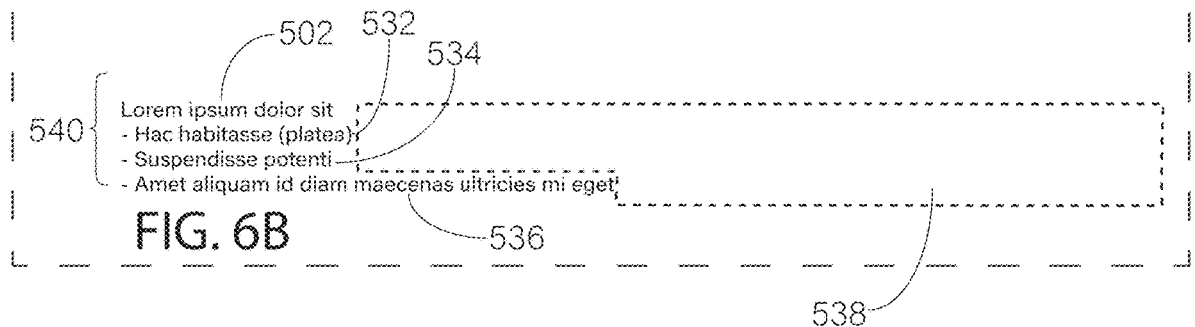
FIG. 6B is an example of what a user may see in a printout on paper after completing the multi-select text box of FIG. 6A.

FIGS. 6A and 6B depict an example of what a data entry user 78 would normally see after completing a multi-select text box using existing systems (e.g., currently employed EMR systems). The current example includes a prompt 502 and three selected response options (504, 506 and 508) that show which response field options the data entry user 78 selected. The current example has a total height 510 and a total width 512, as shown. The current example includes a line 514 that that separates the current prompt 502 from the previous question, a line 516 that separates the prompt 502 from the potential response options and a line 518 that separates the current question from the next question.

FIG. 6B shows a typical printout from an EMR, as a display user 81 might see it. On the successive lines following the prompt are the texts of the various options selected (532, 534 and 536) each prepended with a tick mark to indicate a separate response to the current prompt. It is generally contemplated that the vertical alignment of the responses may help the user determine where each answer begins and ends. There is unused space 538 caused by the format of the display, that may be representative of other unused spaces common to [typical document formats], including EMR documents.

Figure 6C:
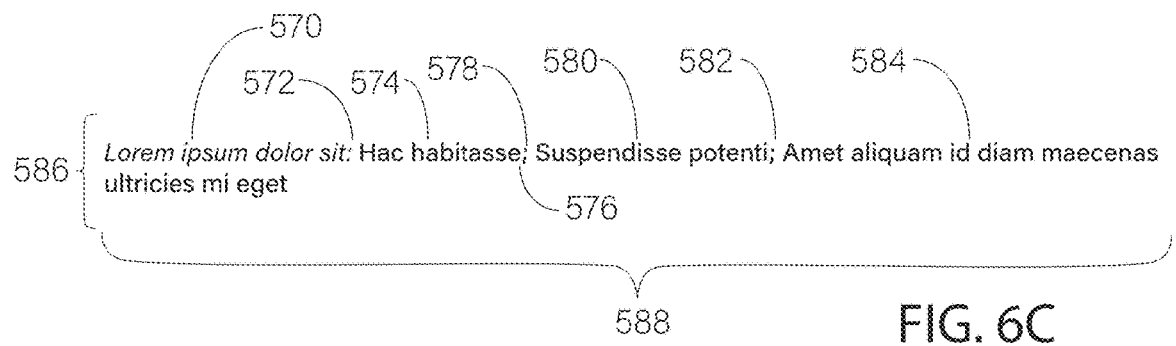
FIG. 6C is an example of an optimized pure text conversion of the multi-select text box of FIG. 6A.

FIG. 6C shows an embodiment of a pure text conversion, generated in accordance with the present invention, of the data shown in FIG. 6A. The prompt 570 shows the prompt 502 after applying the user defined prompt attributes. More specifically, the prompt 570 is appended by the user defined combining string 572 (in this case, a colon followed by a space) and the first option selected 574 is formatted using the user defined response attributes. Note that the selected response option 504 ended with a parenthetical comment. The place 576 where the parenthetical comment "(plates)" was excluded, is shown. The other two selected response options (580 and 584) are appended by user defined concatenation strings (578 and 582) between each. Both of these are also displayed using the user defined response attributes. The total width 588, which is proportional to the width allowed to display documents on the display user's screen, and total height 586 are also shown.

The lines of the form design 49 fit into the subcategory of non-textual design of the other 74 box and as such are excluded from being incorporated.

Note that the prompt-response field of FIG. 6A has a total height 510 of approximately 6 lines, prompt-response field of FIG. 6B has a total height 540 of 4 lines, and the prompt-response field of FIG. 6C has a total height 586 of only 2 lines to display the same content. Both the total width 512 of the prompt-response field of FIG. 6A and the total width 588 of the prompt-response field of FIG. 6C are identical. The amount of space used up by the selected fonts in this example is larger in FIG. 6C than in FIG. 6B because bold proportional fonts occupy more space than non-bolded versions of the same font. Even with the wider, more readable font of the response text in FIG. 6C, the invention of the present disclosure takes fewer lines to display the same text than it would have required otherwise (e.g., using existing systems). The result is that more information is now able fit on the screen because there will be more space available for additional rows that were previously lower than the bottom of the display screen.

Figure 7A:
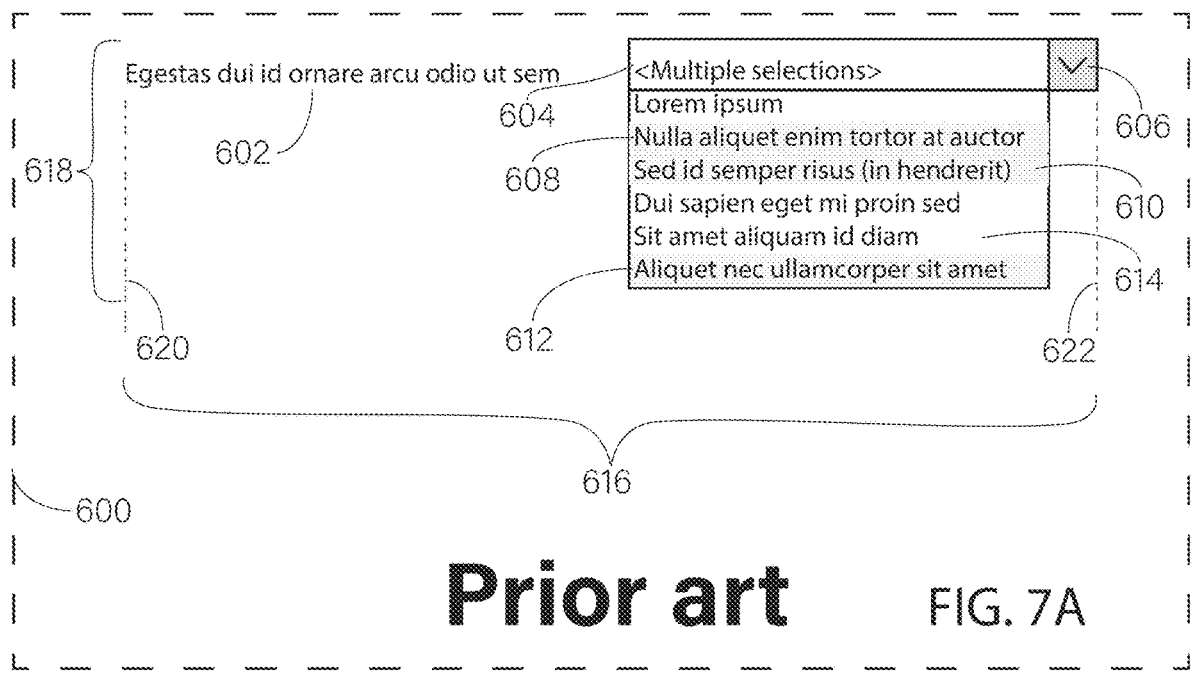
FIG. 7A is an example of a typical multi-select dropdown list.

FIG. 7A depicts an example of what a data entry user would typically see immediately after completing a multi-select dropdown list, using existing systems (e.g., currently employed EMR systems). The prompt 602 is shown. The response box 604 includes the available options that may be selected and viewed. The response box 604 had a hotspot 606 to toggle dropdown viewing. In this example, three selected options (608, 610 and 612) and a sample unselected option 614 is demonstrated. Shown is the left boundary 620 for the start of the prompt area (e.g., the furthest-left boundary), and the right boundary 622 for the end of the response area (e.g., the furthest-right boundary). In one or more examples, the left boundary 620 and the right boundary 622 collectively define a pair of "absolute boundaries." The total height 618 and total width 616 of the multi-select dropdown are also shown, with the width being measured from the left boundary 620 to the right boundary 622.

Figure 7B:
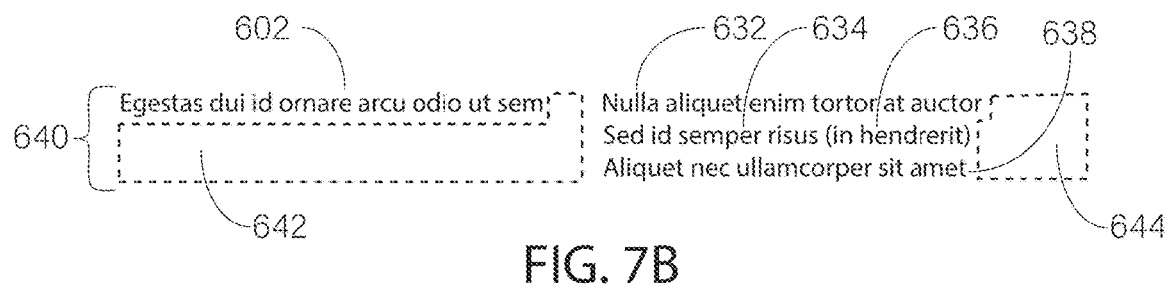
FIG. 7B is an example of what a user may see in a printout on paper after completing the multi-select dropdown list of FIG. 7A.

FIG. 7B shows a hypothetical printout from an EMR, as a display user 81 might see it. There are three selected options (632, 634 and 638) and one parenthetic comment 636 within these selected options. The total height 640 is shown, as are unused spaces (642 and 644).

Figure 7C:
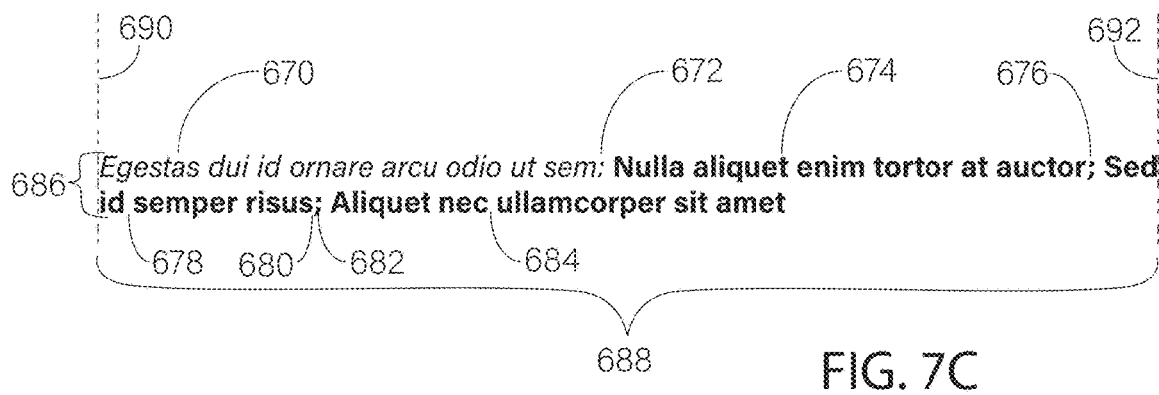
FIG. 7C is an example of an optimized pure text conversion of the multi-select dropdown list of FIG. 7A.

FIG. 7C shows a line of pure text generated using the process of the present disclosure to display the data shown in FIG. 7A. The prompt 670 is formatted in the following order: (1) using user defined prompt attributes and has the user defined combining string 672 appended; (2) the first response 674 formatted using the user defined response attribute; (3) the user defined concatenation string 676; (4) the second response 678 in the same format; (5) the second user defined concatenation string 682; and finally (6) the third response 684. The second response originally included a parenthetical comment 636 that was excluded at point 680 since it was not typed by a data entry user 78 and is not part of a computed field format. The height 686 of this prompt-response field easily fits into just 2 lines.

Another issue that is illustrated in FIG. 7C is the calculation of horizontal boundaries. In FIG. 7A, the information started at left boundary 620 and ended at right boundary 622, and was laid out as if it was 2 columns with a non-zero quantity of space between the columns. Thus, the total horizontal space allowed when the prompt-response field is the total width 616, which is the same total width 688 of the prompt-response field used in FIG. 7C. As shown, it has a left boundary 690 and a right boundary 692, both corresponding to the data entry user's boundary of 620 and 622.

Figure 8:
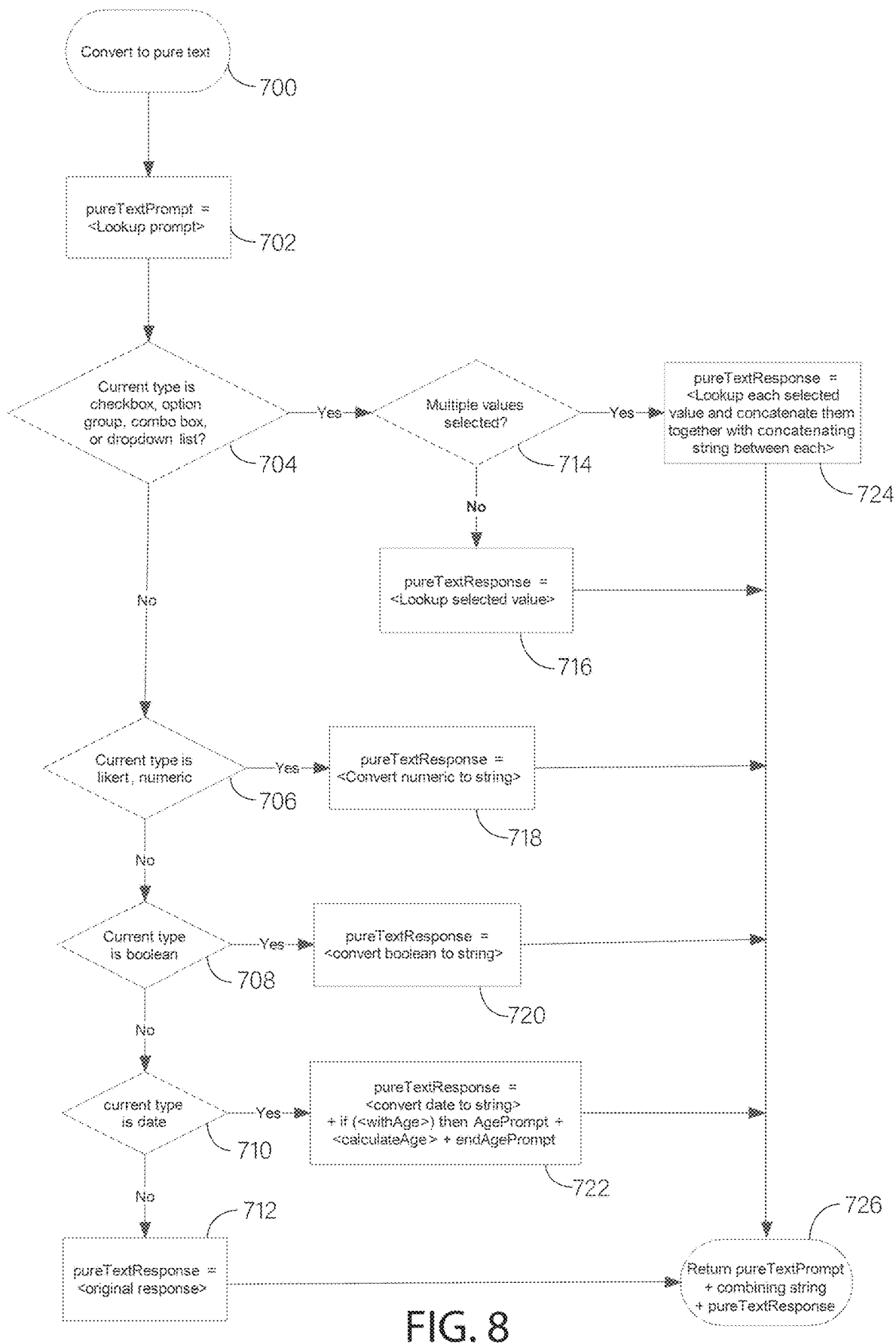
FIG. 8 is a flow diagram depicting how to convert prompt-response fields into pure text.

Referring to FIG. 8, depicted is a flow diagram illustrating one example of a method for converting prompt-response fields into pure text. Step 700 is the start. This function needs to be passed a pointer to the prompt, another pointer to the list of responses and an indication of the type of response that is being passed (e.g., a checkbox, an option group, a combo box, a dropdown list, a Likert group, a numeric value, a Boolean, a date, etc). Alternatively, a pointer could be passed to a structure that contains this information.

Step 702 converts the pointer to the prompt, to text. Doing so may entail, for example, reproducing the prompt to yield a reproduced prompt. In general, however, this may be performed by a lookup in a database, such as "SELECT PromptText FROM Lookup WHERE Id=:PromptKey".

Step 704 checks if the response is going to be text that merely needs to be looked up from the response pointer. If so, step 714 checks whether there are multiple values to look up. If there are not multiple values, then step 716 converts the single value to pureTextResponse (e.g., a "converted response"). Again, this is generally done by a database lookup, such as "SELECT ResponseText AS pureTextResponse FROM Lookup WHERE Id=ResponseKey". If there are multiple values, then step 724 does such a lookup for each response and combines them all together with the user defined combining string to create pureTextResponse. Either way, the data is ready to return from the function afterwards in step 726.

Step 706 checks if the response is a numeric value. If so, the process converts the numeric value to pureTextResponse in step 718 (e.g., a "converted response"). The conversion is done using processes well known to those skilled in the art. The process then returns both pure text fields in step 726.

Step 708 checks if the response is a Boolean value. If so, the process converts the Boolean value to pureTextResponse in step 720 (e.g., a "converted response"). This conversion is done using processes well known to those skilled in the art. The process then returns both pure text fields in step 726.

Step 710 checks if the response is a date value. If so, the date is converted to a string format (e.g., a "converted response") using, for example, the well-known processes described in step 722. The process at step 722 then checks if the format of this date includes an age calculation. If an age calculation is included, calculation of age is done by processes well known to those skilled in the art (such as . . . ). The age is then appended to the pureTextResponse string in a pre-determined format. For example, the format could be "7/1/90 (Age 28)".

If the format includes parenthesis, as in this example, it is generally contemplated that something should be done to prohibit other portions of the current embodiment of the invention from automatically deleting the parenthetical comment. This may include, for example, using square parenthesis instead of rounded parenthesis, inserting a placeholder in place of the parenthesis at this stage and replacing the placeholder with parenthesis after automatic excluding of parenthetical comments is complete, and/or inserting a flag in the response string that that tells the automatic exclusion of parenthetical comments to skip this string when processing, then removing that flag from the string after automatic exclusion of parenthetical comments is complete. The process then returns both pure text fields in step 726.

If none of the above is applicable, step 712 copies the response submitted to the pureTextResponse field and then returns both pure text fields in step 726 (e.g., a "converted response").

Figure 9:
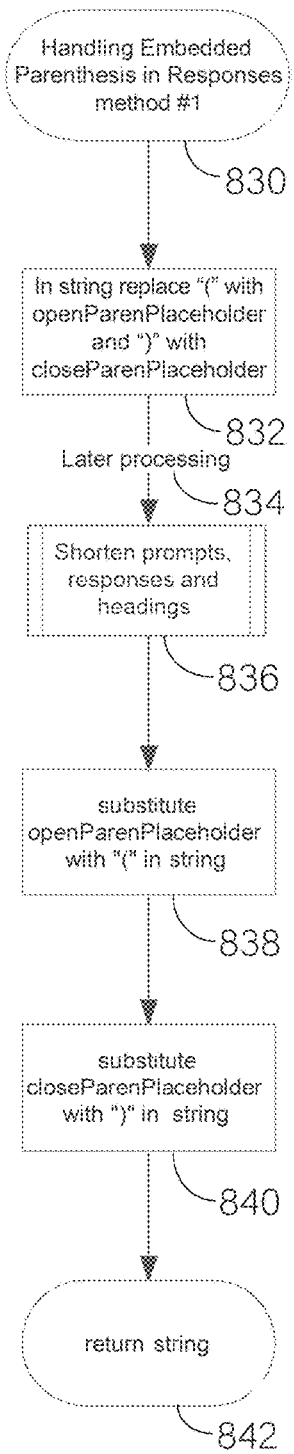
FIG. 9 is a flow diagram depicting a first example method of suppressing automatic exclusion of parenthetical comments.
Figure 10:
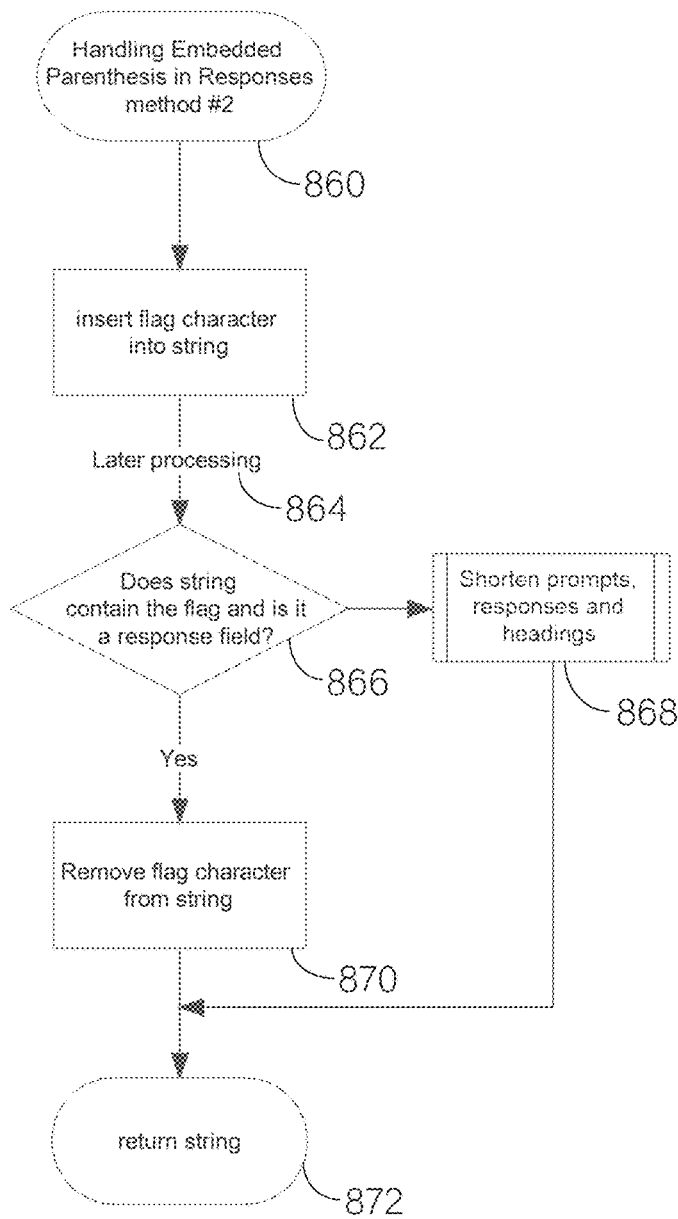
FIG. 10 is a flow diagram depicting a second example method of suppressing automatic exclusion of parenthetical comments.

FIGS. 9 and 10 show two alternate functions that restrict shortening by excluding parenthetical comments in responses that were either manually typed by the data entry user 78 or are computed fields that include a parenthesis in the format. If the format includes parenthesis, these functions prohibit Shorten prompts, responses and heading function method #2 from automatically deleting the parenthetical comment. The various methods of doing this may include, for example, (1) using square parenthesis instead of rounded parenthesis, (2) the method starting in step 830 (e.g., inserting a placeholder in place of the parenthesis at this stage and replacing the placeholder with parenthesis after automatic excluding of parenthetical comments is complete), and (3) the method starting in step 860 (e.g., inserting a flag in the response string that that tells the automatic exclusion of parenthetical comments to skip this string when processing, then removing that flag from the string after automatic exclusion of parenthetical comments is complete).

In step 830, a string is passed into the function.

In step 832, the string has all the parenthesis replaced by openParenPlaceholder or closeParenPlaceholder, depending on whether it is an open parenthesis or a close parenthesis.

In step 834, a period of time is provided during which other processing operations may occur. Then, in 836, once the Shorten prompts, responses and headings function is executed, the temporary openParenPlaeholder and closeParenPlaceholder with "(" in step 838 and ")" in step 840, respectively. Finally, return the computed string in step 842.

In step 860, a string is passed.

In step 862, a flag is set to indicate that this string does not get processed through the Shorten prompts, responses and headings function. This may be as simple as placing a tilde character as the first character of the string or as complex as having a structure that accompanies the string through processing.

In step 864, another period of time is provided during which other processing operations may occur. A check is made to see if the flag is associated with the string, and whether it is a response field in step 866. (Obviously, a check could have been made before executing step 862 to see if it is a response field and move that test to there and that would accomplish the same thing.) If the flag is not present, the call is made to the Shorten prompts, responses and headings function in step 868.

If the flag is present, then it may optionally be removed after it has served its purpose in step 870. Finally, the computed string is returned in step 872.

Figure 11:
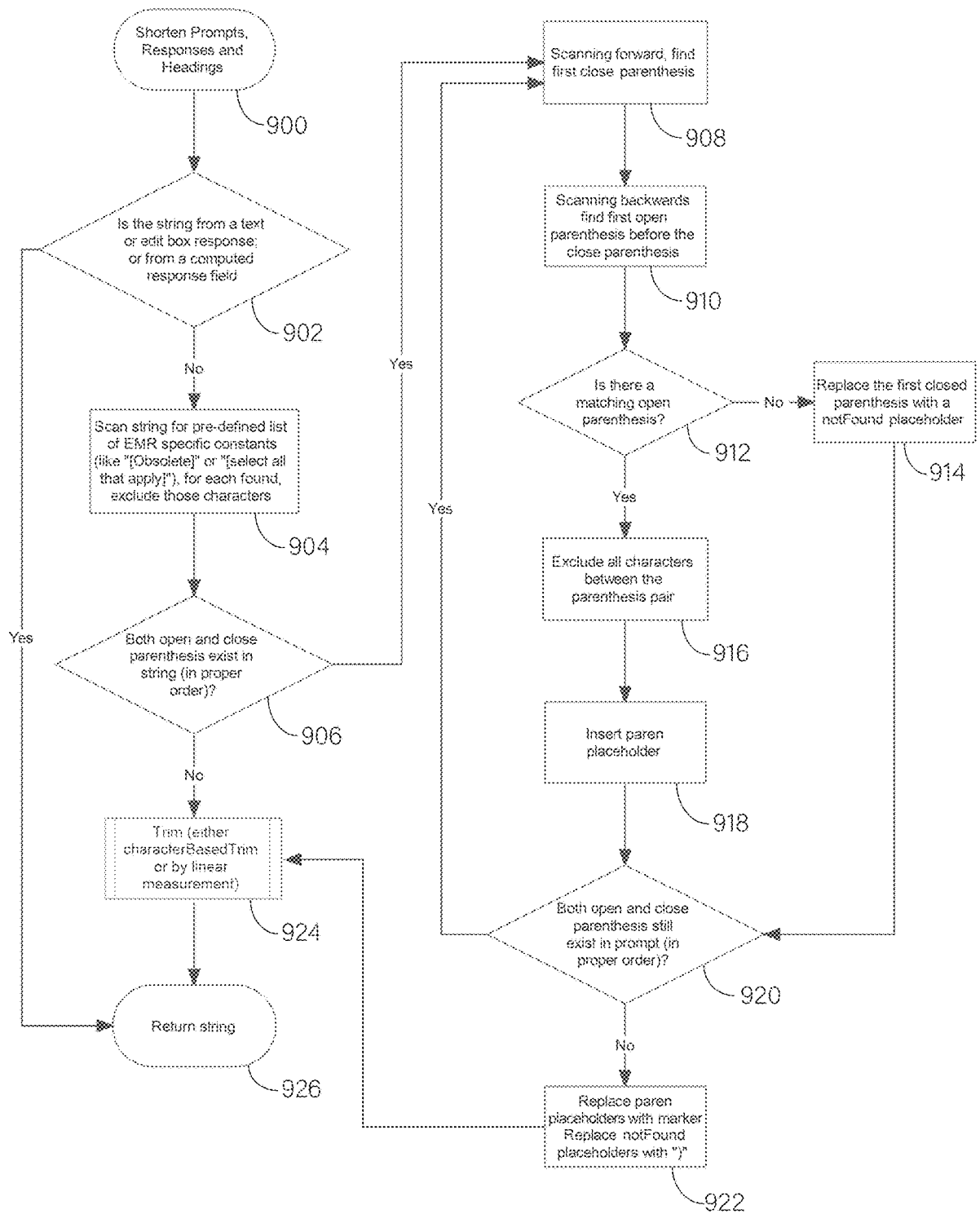
FIG. 11 is a flow diagram depicting an example method of shortening prompts, responses and headings by excluding characters.

Referring to FIG. 11, a flow diagram that depicts an example process of how to shorten prompts by excluding characters. It starts at step 900 by passing in the string to shorten.

In step 902, a check is made to prevent character exclusion when either the data entry user 78 types the text of the current field or the current field is a system generated field that includes a parenthesis. If so, the process skips to step 926.

In step 904, the program is presented with a list of phrases that may be automatically excluded when they are encountered. For example, one phrase on the list in an embodiment is "OBSOLETE:<space>", where "<space>" represents the ASCII character hexadecimal 20 (which has been previously employed to mark no longer used fields in standardized data forms with this as a prefix). Then, if an obsolete prompt is accidentally included in the design of a data form, that prompt will start with the characters "OBSOLETE:", thereby making it easier for a form designer to catch the error. This practice, however, unfortunately produces an exorbitant number of "OBSOLETE:" strings when older data forms are viewed. Excluding these "OBSOLETE:" strings not only potentially reduces the quantity of lines required to display the data form, but also makes the resulting data forms more readable because they do not contain random "OBSOLETE:" strings scattered around the data form.

To complete this example of excluding this specific visual prompt queue, a command may be issued to exclude the first 10 characters from any string starting with "OBSOLETE:", such as "UPDATE # Elements SET Prompt=SUBSTRING (Prompt, 11, LEN(Prompt)) WHERE Prompt LIKE 'OBSOLETE: %%'".

A similar example would be to eliminate the characters "(select all that apply)" from the end of a prompt. A sample SQL command for this may be: UPDATE # Elements SET Prompt=RTRIM(LEFT(Prompt, LEN(Prompt)−23)) WHERE Prompt LIKE '%% (select all that apply)'.

In step 906, a scan may be performed in search of open parenthesis followed by, after some quantity of characters, a close parenthesis. If so, at step 908, a scan may be performed to find the first closed parenthesis. Once found, a scan may be performed for the matching open parenthesis by scanning backwards from that point in step 910. If, in step 912, no open parenthesis is found in this backward scan, then the closed parenthesis that was found may be hidden by changing it to a notFound placeholder in step 914.

If, in step 912, an open parenthesis was found, then all the characters between the parenthesis pair may be excluded, including the parenthesis in step 916. In step 918, a paren placeholder can optionally be added to mark where the parenthesis pair was excluded.

In step 920, the same check that was performed in step 906 may be performed again to determine whether any further open and close parentheses pairs still exist in the string.

In step 922, if there were any paren placeholders placed in the string, they may be replaced with appropriate character strings. This character string can be any suitable value, such as NULL, "0" or any other suitable character or combination of characters. The character string may also be user definable. Also, the notFound placeholder may be changed back to the character it replaced (i.e., ")").

In step 924, an optional call may be to a procedure for trimming the string such that the string does not exceed a maximum length. This can be accomplished with a call to procedure 1031 or a call to procedure 1111.

Finally, in step 926, the string is returned from the function.

Figure 12:
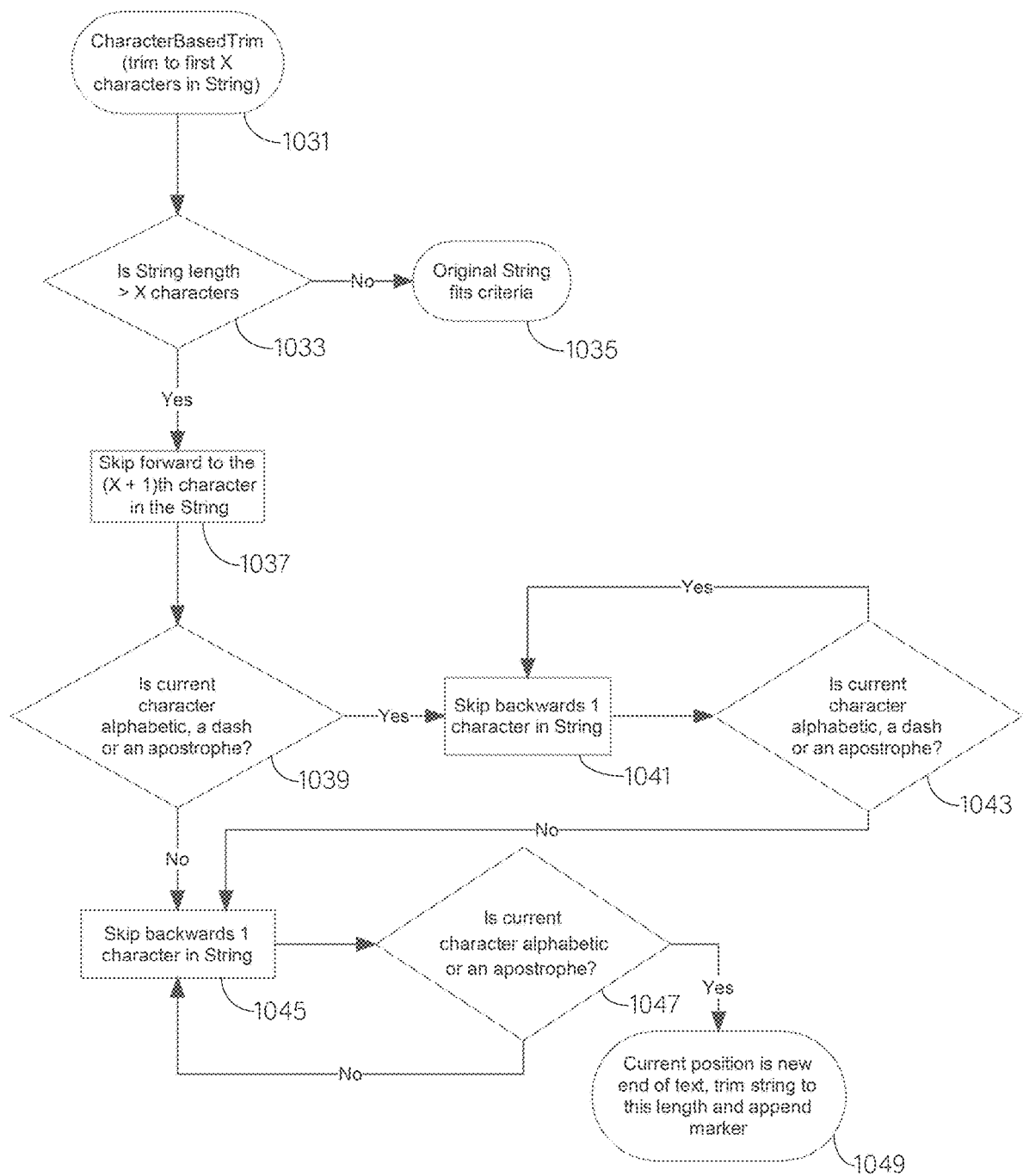
FIG. 12 is a flow diagram depicting an example method of trimming a string to the maximum number of whole words less than a pre-specified maximum quantity of characters.

Referring to FIG. 12, depicted is a flow diagram illustrating one example of how to trim a string to the maximum number of whole words less than a pre-specified maximum quantity of characters.

Procedure 1031 starts with step 1033, checking if the string is larger than the pre-specified maximum quantity of characters. If not, step 1035 may exit the function by returning the whole string. In step 1037, the function skips to one character beyond the pre-specified quantity of characters (e.g., the "current character").

Step 1039 checks if the current character could be a character within a word (e.g., alphabetic, a dash for hyphenated words or a character that can end a word). If so, step 1041 scans backwards looking for the first character that is not a character within a word in step 1043. Once that first character is encountered, processing resumes at step 1045, as if step 1039 had not detected a character in the middle of a word.

If the current character at step 1039 is not a character within a word, then step 1045 backs up one character, and loops through backing up a single character at a time until a character is encountered that could be the last character in a word in step 1047.

Finally, the end of the last word has been located in step 1049. The function may then return the characters from the start up to the end of that last word.

Figure 13:
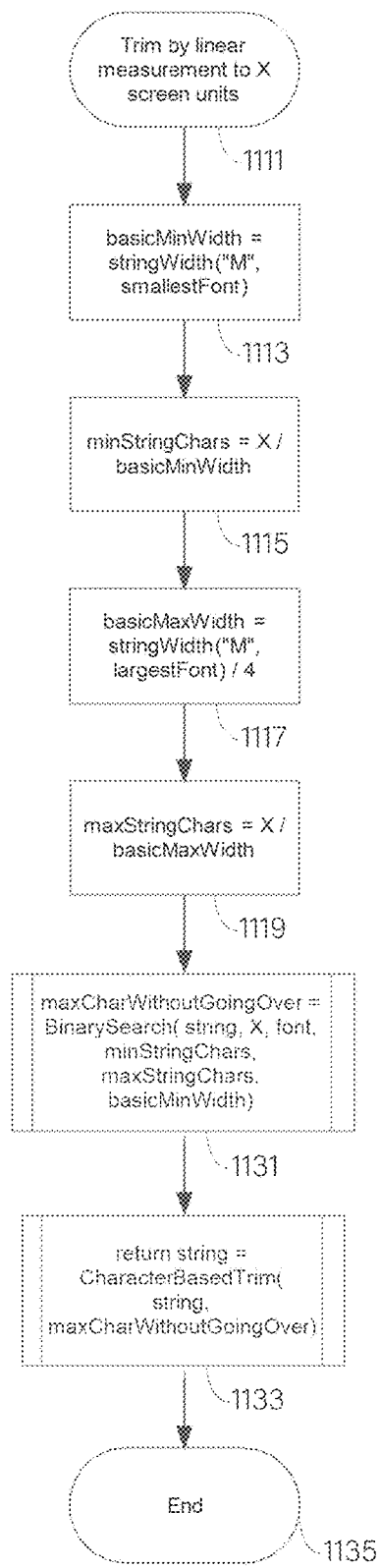
FIG. 13 is a flow diagram depicting an example method of trimming a string to a linear length only showing whole words.

Referring to FIG. 13, depicted is a flow diagram illustrating an example of how to trim a string to a linear length, as measured in points, number of characters, and/or traditional measurement units (e.g., Imperial system and/or Metric system). The function shown may be considered optimized, in that it minimizes how many loops are necessary to determine how wide a long string is in a specific font.

This function assumes the availability of a system function that you can feed a pure text string to, plus a font definition (font name, size and other font attributes such as weight) and it returns the linear length of the string.

The widest standard character in most proportionally spaced fonts is a capital "M". The smallest character in most proportionally spaced fonts is a period and it usually takes four periods to have a string about the same width, or ever so slightly wider than a letter "M".

Procedure 1111 starts with steps 1113 and 1115 calculating the minimum quantity of characters that could fit in a space that is being requested. Similarly, in steps 1117 and 1119, a calculation is made of the maximum quantity of characters that could fit in the space being requested.

In step 1131, a call is made to procedure 1171 to determine the maximum quantity of characters that will fit in the pre-specified linear length.

In step 1133, a call is made to procedure 1031 to force the trimming to end with a whole word.

The function ends in step 1135. At this point, a person skilled in the art will appreciate that mixed font strings, such as a prompt-response string, may be handled by handling each font separately, and in the order in which they appear in the string until the desired total length is reached.

Figure 14:
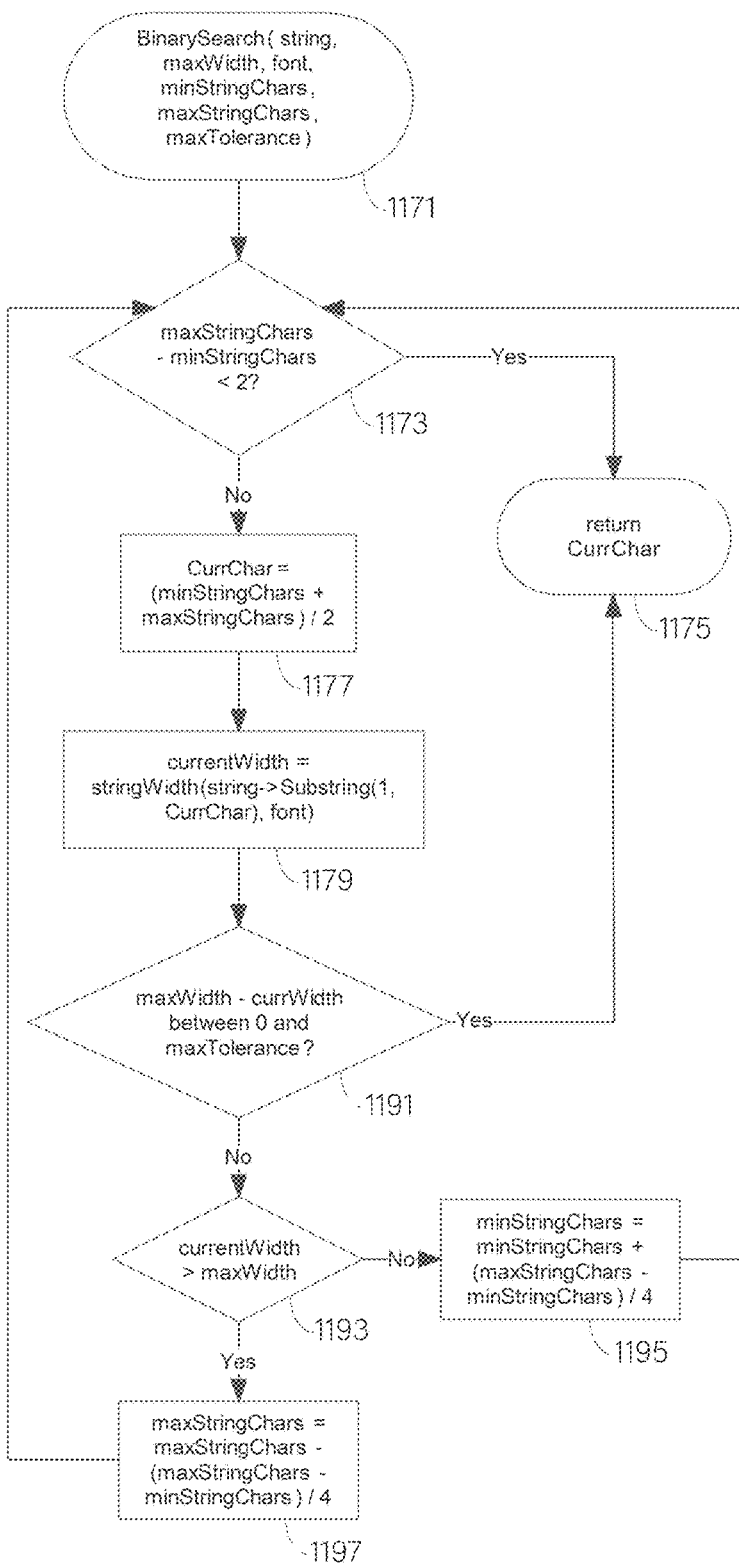
FIG. 14 is a flow diagram depicting an example method of performing a binary search to find a string with a linear length not exceeding a pre-determined length.

Referring to FIG. 14, depicted is a flow diagram illustrating how to perform a binary search in order to find a string whose linear length does not exceed a pre-determined length, and does not split words. The function begins in step 1171. Note that the parameters start with an estimate of both the minimum quantity of characters and a maximum quantity of characters, and a tolerance of how close one has to be before exiting the loop early. This degree of tolerance may be applied later in step 1191.

In step 1173, the loop should exit if the difference between the minimum and maximum character position is less than a predetermined quantity of characters. In the embodiment shown, two is the predetermined quantity.

In step 1177, the current character position may be calculated. Because the current character is positioned between the minimum and maximum character, in one example, the calculation may include averaging the two extremes (e.g., the minimum and the maximum character). If the result of averaging in this step results in a number with a fractional value, the fractional value is dropped to get the current character position with a bias toward the lower value (e.g., rounding down).

In step 1179, a system call may be made to determine how wide the string up to the current character position would be when printed to the screen using the current font.

In step 1191, a check may be made to determine if the current character position would yield a string that is not larger than the maximum width, but within the pre-specified tolerance for being acceptably close. Those skilled in the art will appreciate that it may be expensive in terms of computer cycles to perform step 1179, but once that value has been calculated for the loop, it is relatively quick to do this check and possibly shortcut several cycles of the loop. Further, if it is within the pre-specified tolerance, the character position has been found and is returned at step 1175.

In step 1193, a check may be performed to determine which value to adjust for the next pass through this function. This may entail raising the minimum quantity of characters and/or reducing the maximum quantity of characters.

In step 1195, the minimum quantity of characters may be increased if the current width is less than the pre-determined length. In the example shown, the amount of increase is ¼ of the difference between the minimum quantity of characters and the maximum quantity of characters. If the result of calculating the increase results in a fractional amount, the fractional amount may be dropped.

In step 1197, the maximum quantity of characters may be decreased if the current width is more than the pre-determined length. In the example shown, the amount of decrease is ¼ of the difference between the minimum quantity of characters and the maximum quantity of characters. If the result of calculating the decrease results in a fractional amount, the fractional amount may be dropped and the maximum quantity may be increased by 1.

In FIG. 15, the string "this is a test to see how much will fit" 1215 is being processed starting at step 1111. Character count positions are shown for the $10^{th}$, $20^{th}$, $30^{th}$, and $40^{th}$ character positions 1211. An inch ruler 1219 and a point ruler 1217 is shown to measure the width of the string. Further, string width 1213 also shows a graphical representation of the values for the $1^{st}$, $2^{nd}$, $3^{rd}$, $4^{th}$ and $5^{th}$ cycles of step 1179 through the loop.

FIG. 16 shows a number of different values calculated at various steps of FIG. 13 while processing the string of FIG. 15. The first column 1231 shows the step number. The second column 1233 shows the computed values resulting from executing that step.

FIG. 17 shows the calculated values at five different passes through the loop of FIG. 14 while processing the string of FIG. 13. First column 1281 shows the various pass numbers where 1 corresponds to the first pass, 2 corresponds to the second pass, and so on. The cycle numbers 1213 correspond to the pass numbers 1281. The second column 1283 and third column 1285 show the values for the minimum quantity of characters and maximum quantity of characters respectively at the start of the loop, step 1173. The fourth column 1287, shows the value of CurrChar at the end of step 1177. The fifth column 1289, shows the value of CurrWidth at the end of step 1179. The sixth column 1291, shows the choice of whether the calculated value was too long in step 1193. The seventh column 1293, shows the calculated values calculated during the loop at the end of step 1195. The eighth column 1295 shows the values calculated during the loop at the end of step 1197. On the fifth pass, the loop exits early in step 1193.

FIG. 18 shows the processing of the text string of FIG. 15 through the loops of FIG. 12. The value passed in step 1133 to the function 1031 is 29. After step 1037, the pointer to the string point to the "h" in "much" 1251. Since "h" 1251 is alphabetic, step 1041 changes the pointer to the string to the "c" in "much" 1253. Since "c" 1253 is alphabetic, step 1041 changes the pointer to the string to the "u" in "much" 1255. Since "u" 1255 is alphabetic, step 1041 changes the pointer to the string to the "m" in "much" 1257. Since "m" 1257 is alphabetic, step 1041 changes the pointer to the string to the space before "much" 1259. Since the space 1259 is not alphabetic, step 1045 changes the pointer to the string to the "w" in "how" 1271. Since "w" 1271 is alphabetic, the function has found the end of the last whole word that can be displayed with the string.

Figure 19:
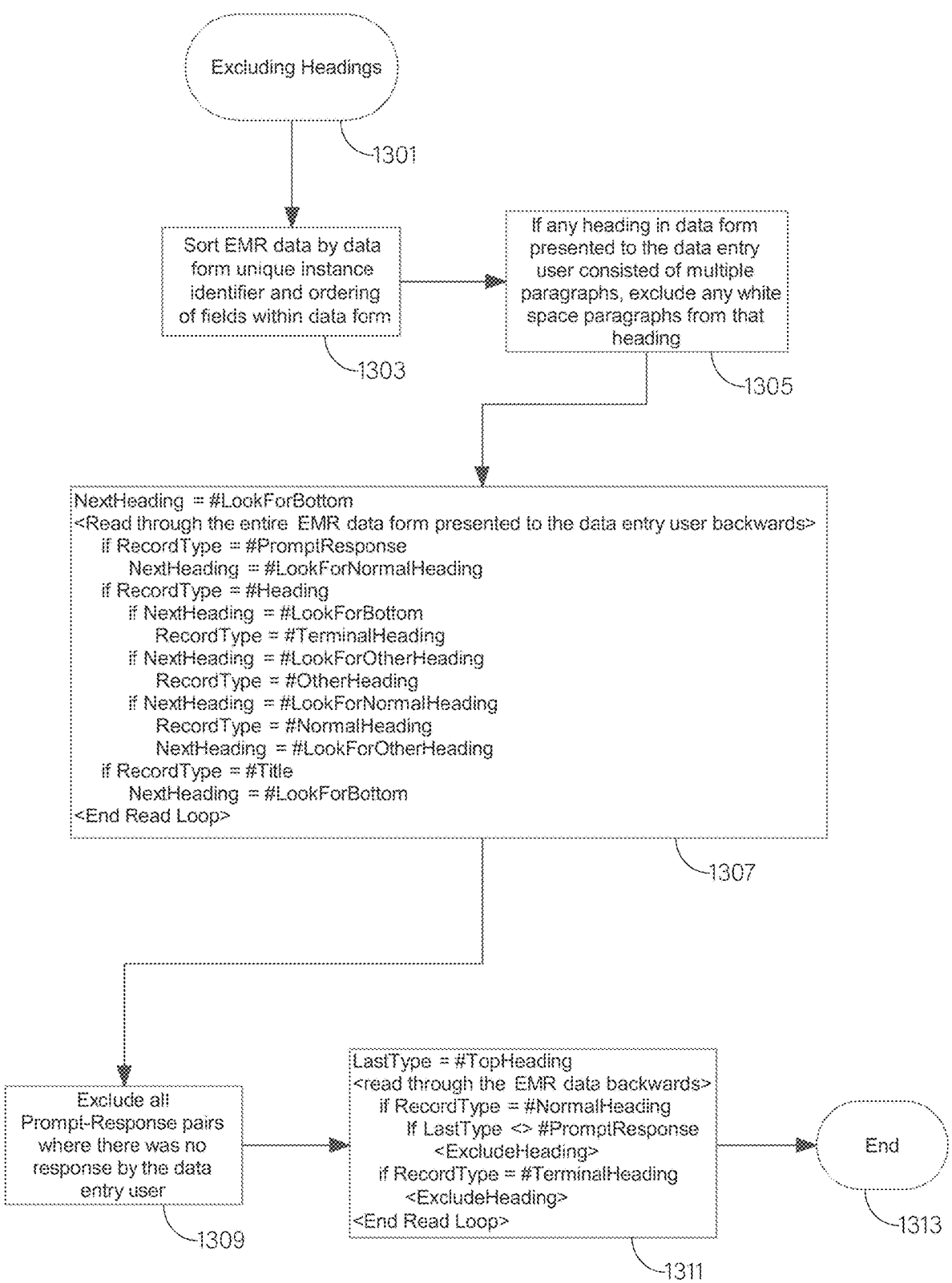
FIG. 19 is a flow diagram depicting an example method of calculating headings to exclude.

FIG. 19 shows how to calculate which headings may be excluded from an electronic medical record data form beginning in step 1301. Excluding headings may be performed by calculating what type of heading each one is, and by removing any low-level heading that is not followed immediately by a prompt-response field.

The first step 1303 sorts data from the EMR for the data forms being viewed. This may be done using a unique instance identifier that identifies the data form being used and the data set of responses that fills in that data form. In one example, this might include the date or appointment identifier plus the type of data form or it might be a single identifier that identifies the data responses such as a primary key; and an ordering of the fields within the documents, this is typically either a row plus column number (and optionally, a panel identifier) or a ViewByOrder column associated with the data form layout in the EMR.

In step 1305, any blank lines may be excluded in headings. These blank lines may have been added to the data form design for emphasis but generally are not required.

In step 1307, a loop may be set up to classify the different types of headings. In step 1307, the data form fields being referred to are the data form design, regardless of whether any prompt-response field is responded to. A heading after the last prompt-response field in a data form is classified a terminal heading. A heading immediately before a prompt response field is classified as a normal heading. All other headings are classified as other headings. Since headings are classified based upon what follows the heading, it is more efficient to scan the data form from the bottom to the top so processing can be done in a single pass without any back-tracking. The analysis of step 1307 can be done long before any analysis of a specific completed response and store the classification of the headings somewhere for future use. These classifications would only need to be updated after changing the design of a data form.

In step 1309, every prompt-response pair may be excluded where the prompt was not responded to. What remains is processed in step 1311, where any normal heading that is followed by anything other than a prompt-response field means the normal heading needs to be excluded. Also in this step, all terminal headings need to be excluded. As in step 1307, it is more efficient to read the EMR data backwards (from bottom to top). The difference with step 1307 is that the only data being included in step 1311 are titles, headers and prompt-response fields with responses. Recall, in step 1307, the data being included was titles, headers and all prompt-response fields.

In step 1313, the process is complete.

FIG. 20 shows a small portion of an example of a data entry form that will demonstrate removing an unused normal heading. There are five headings shown (1401, 1403, 1409, 1415 and 1417). Upon initially looks at these headings, they all appear identical in structure, just with different wording for each heading. There are seven repetitions of the structure between the parent free text box 1405 and the date box 1431, some headings and an option group 1419. There are three free text boxes (1405, 1411 and 1429), three combo boxes (1423, 1407 and 1421), one numeric field 1425, one option group 1427, and one date field 1431 in the structure.

1407 is a combo with possible responses: "Grade School", "Less than High School", "Completed High School", "Some College", "4-Year Degree", and "Graduate/Professional Degree".

1421 is a combo box with possible responses: "Single", "Serious dating or committed relationship", "Civil union, domestic partnership, or equivalent", "Married", "Separated", "Divorced", and "Widowed".

1423 is a combo box with possible responses: "Father", "Mother", "Guardian", and "Spouse/Partner".

FIG. 21 shows an example of how FIG. 20 may appear after step 1309. All the unanswered prompts have been removed, otherwise, everything else remains.

FIG. 22 shows the calculated values from the loop in step 1307 as it processes FIG. 20. The second pass through the loop looks at Yes/No prompt field 1419, it is in the category of a # PromptResponse. As a # PromptResponse, NextHeading is set to # LookForNormalHeading. Then, at the third pass 1501 through the loop, the loop processes heading 1417. Since heading 1417 is a heading, it categorizes the RecordType as # NormalHeading and sets the NextHeading to # LookForOtherHeading. Then, in the fourth pass, it finds heading 1415. Since heading 1415 is a heading, it categorizes the RecordType as # OtherHeading.

Similarly, in pass 44, the loop is processing the prompt-response field 1411, which set NextHeading to # LookForNormalHeading. Then pass forty five 1503 classifies heading 1409 as a # NormalHeading.

Finally, in pass 61, the loop is processing the prompt-response field 1405, which set NextHeading to # LookForNormalHeading. Then pass sixty two 1505 classifies heading 1403 as a # NormalHeading and NextHeading is set to # LookForOtherHeading. Then pass 63 classifies heading 1401 as a # OtherHeading.

FIG. 23 shows an example how FIG. 20 may appear using an embodiment of the current invention after step 1311 with the heading removed and everything turned to pure text. Step 1311 may remove heading 1409 from FIG. 21 because heading 1409 is a normal heading and is followed by heading 1415, which is another heading, not a prompt-response.

Figure 24:
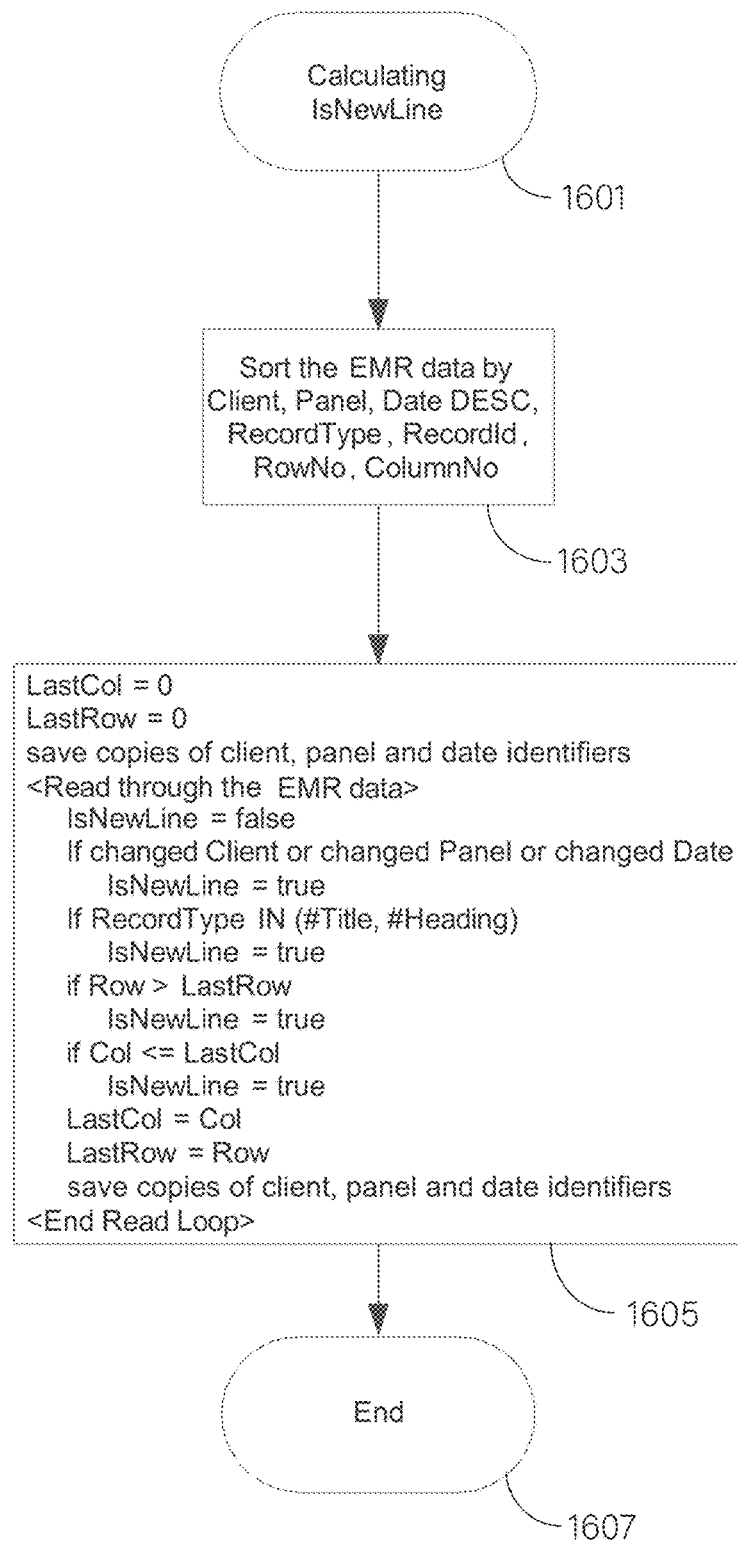
FIG. 24 is a flow diagram depicting an example method of computing a flag indicating whether the current record starts on a new line.

FIG. 24 shows an example of how to compute a flag indicating whether the current record starts on a new line. This may be necessary if the EMR uses row numbers and columns numbers to lay out data forms rather than a flag that indicates the current record starts a new line since the goal of an embodiment of this invention is to remove lines that are no longer necessary.

Process 1601 starts with step 1603 sorting EMR data by the client identifier (typically, clientId); optionally, the panel on the page on which the data will appear; relevant date of the document; document record type; document record Id; row number; and column number. The "panel" here is being used in the sense of the TPanel object in Embarcadero products where one can have multiple layout panels on a single page.

In step 1605, all the records may be looped through reading one field at a time. Every row in the EMR for a client may be sequentially read through in order marking the row whether or not the row represents a new line on the screen. A new line on the screen occurs every time the row number changes, the client changes, the panel changes, the date changes, the record type is a title or a heading and whenever the column number is not larger than the last column number.

The process ends at step 1607.

Figure 25A:
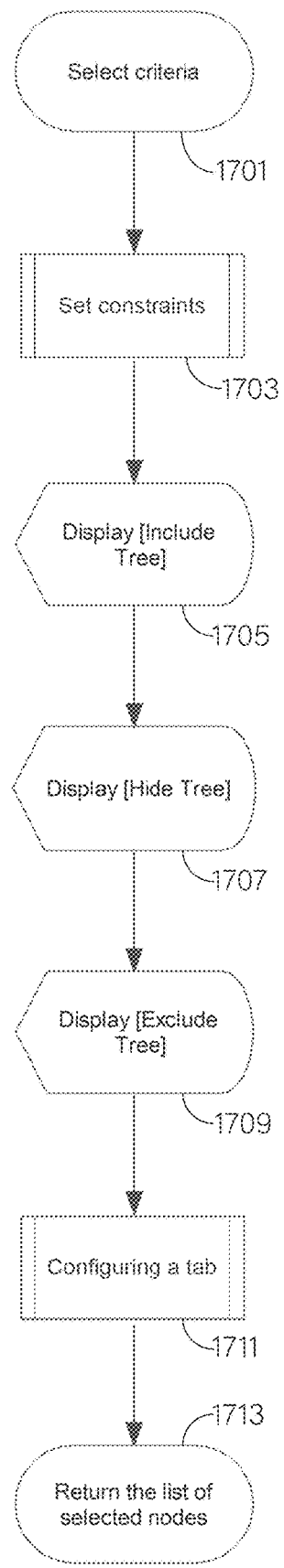
FIG. 25A is a flow diagram depicting an example method of selecting and storing document criteria.

FIG. 25A is a flow diagram depicting an example method of selecting and storing which document criteria will appear on each tab. This may entail more than one document criteria (e.g., a first document criterion, a second document criterion, a third document criterion, etc.). Procedure 1701 starts in step 1703 by setting the defaults for how the trees will interpret various variables that will replace placeholders in the text displayed to the user. The function called to accomplish this is procedure 1861.

In one embodiment, three different trees may be displayed to the user during the configuration state. The first tree has the user picking all the document categories to include on the current page in step 1705. The second tree has the user picking all the document categories to hide on the current page in step 1707. If a document is both included and hidden, the net result will be the document is hidden. If a document is selected to hide, but never selected to include, the document will not appear at all.

The third tree is the list of document categories to exclude from the current page in step 1709. It has priority over the other two trees, meaning that if a document is both selected to include or hide and also selected to exclude, the net effect will be that the document will be excluded.

It is generally contemplated that the idea of a tree may be novel for choosing document categories to include. By way of comparison, when one selects to print a report in an EMR, they are provided with a list of specific documents to include in the report. Effectively, the user has to either take a predefined list of documents or check or uncheck each individual document type, where the leaves of the tree is the level users have had to work in the past. By an embodiment of the invention using a tree to pick from provides different levels of granularity. The individual document types are all at the leaf level of the tree. Being able to pick at the level of branches of the tree allows quick selection of which document types to include rather than having to do it at the leaf level. In addition, as new document types are added to the EMR, if the selections have been made at the branch level rather than at the leaf level, the new document types will automatically be included whenever they fit under a previously selected branch.

In one or more examples, there are some documents that contain raw data that a user will generally not want to see, preferring instead to only see the computer generated reports that come from that raw data. For example, if the client took a standardized test to evaluate their mental state, the user would typically want to see the computer generated scores that indicate the client's mental status, and would only rarely want to see how a client answered all the individual questions. In addition, if there were a few questions that a user wants to see with the standardized report, the individual questions could be included on the tree allowing each user to have their own custom list of questions displayed with the standard computer score.

In the process of selecting and unselecting various branches or leaves of the tree, the corresponding parents or children of the current node will also be selected or unselected. The net effect of this is that only the root of each subtree need be saved and the tree can quickly be reconstructed with just a list of subtree root nodes.

After the trees are displayed, the trees may be used to select which leaf nodes will be included, hidden and excluded from the tab. This is done in step 1711, and the function called here is the procedure beginning at step 1801.

The process ends at step 1713.

Figures 25B, 25C, 25D:
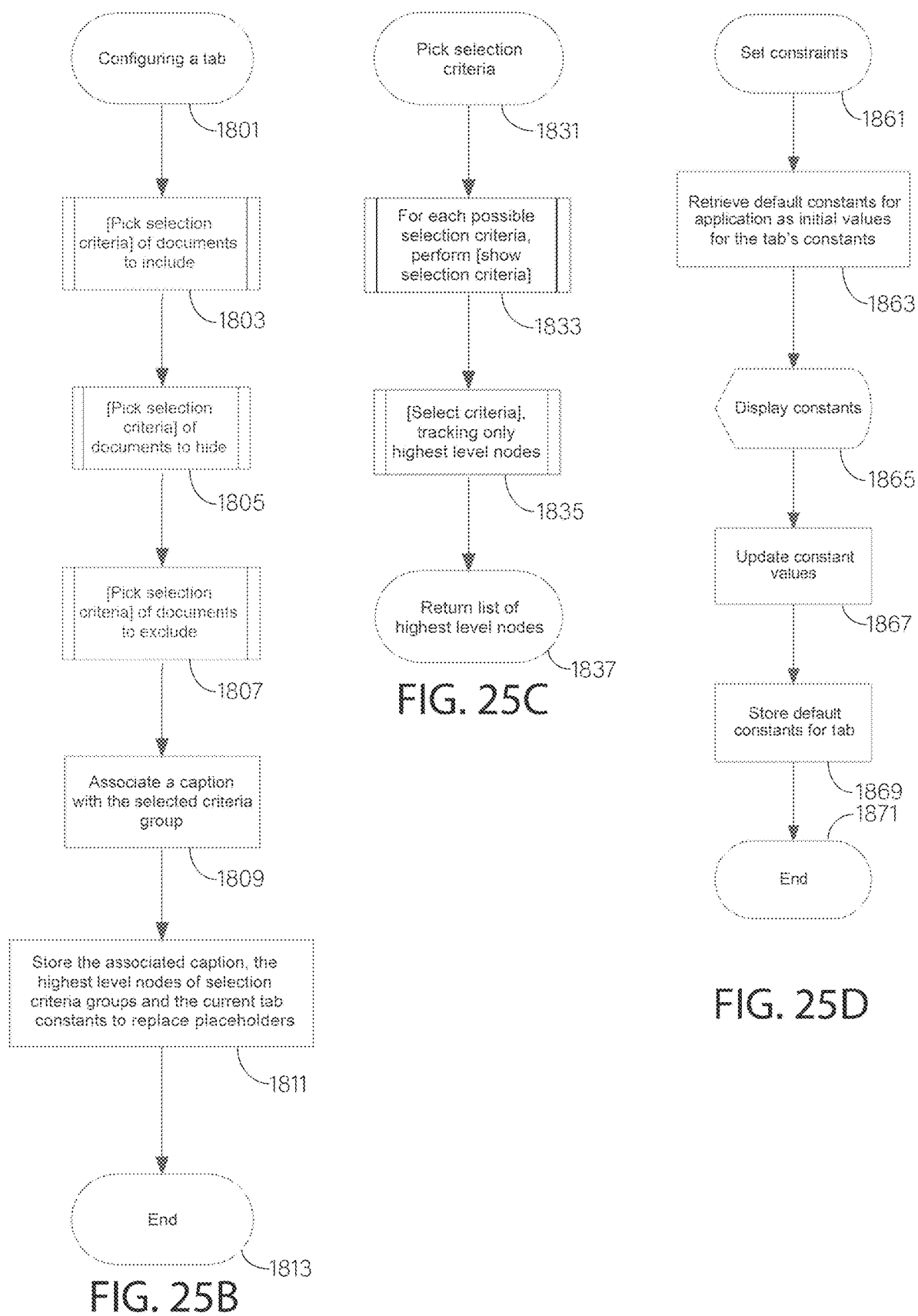
FIG. 25B is a flow diagram depicting an example method of choosing captions, laying out which nodes are selected by subtrees, picking which nodes are going to be selected and storing the captions and subtree roots on one tab.
FIG. 25C is a flow diagram depicting an example method of providing a caption and selecting nodes for one layout subtree.
FIG. 25D is a flow diagram depicting an example method of displaying, updating and storing the constraints.

FIG. 25B is a flow diagram depicting an example method of laying out which nodes are selected by subtrees and picking which nodes are going to be selected on one tab and what else needs to be stored with the criteria subtree nodes.

Process 1801 starts by calling process 1831 in steps 1803, 1805 and 1807. This generally represents the steps of a user selecting which document categories will appear on the tab.

In step 1809, a caption may be chosen for the tab. In one embodiment, the caption is stored with the constraints and list of subtree nodes selected in step 1811. The constants stored in that embodiment are: quantity of days, absolute date, use absolute dates flag, quantity of appointments, quantity of characters and length of measurement. Depending on how the software functions, this may be stored either in program data 4329, or in the data store 43, or some other location the computer has access to.

Step 1813 is the end of the process.

FIG. 25C is a flow diagram depicting an example method of providing captions for the layout subtrees, picking subtree roots and having those translate into leaf nodes, and picking combinations of leaf nodes and having that turn into subtree roots. The method starts at procedure 1831.

Step 1833 calls procedure 1901 which lays out a single caption of the tree. Procedure 1901 is called one time for each node in the three trees.

Step 1835 calls both procedure 2501 and its corresponding undo procedure 2201. Step 1835 is the user interactions of selecting and unselecting nodes and calculating which other nodes are selected or unselected when one node in the tree has its selection status changed.

Step 1837 returns a list of the highest level nodes for each subtree, one set of subtree root nodes for each of the three trees (include, hide and exclude).

FIG. 25D is a flow diagram depicting an example method of displaying, updating and storing the constraints (e.g., procedure 1861). The process starts out retrieving either the application wide current defaults for each of the constraints or the last saved defaults for the current tab in step 1863, depending on whether the defaults have already been saved for this tab. Depending on how the software functions, retrieving the application wide defaults may be performed either from program data 4329, or from the data store 43, or some other location the computer has access to. It then displays those values in step 1865, allows updating the values in step 1867, then stores the constraints for the single tab in step 1869. In 1865, the constraints listed are the tree constraints that will be applied to all three trees for the single tab. An example of these constraints is shown in FIG. 29. The process ends at step 1871.

Figure 25E:
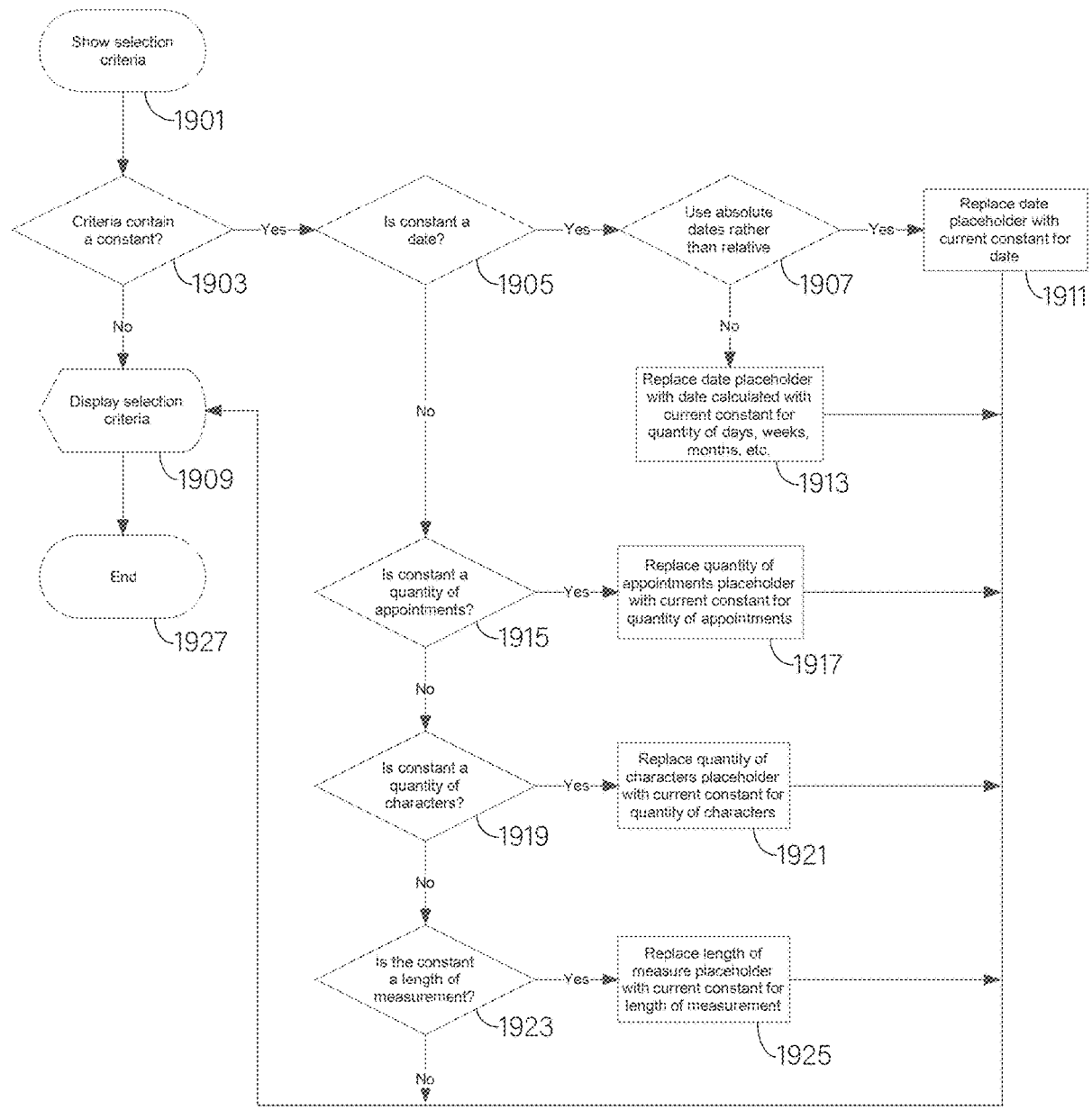
FIG. 25E is a flow diagram depicting an example method of displaying a single node caption of a tree.

FIG. 25E is a flow diagram depicting an example method of displaying of a single node caption of a tree (e.g., procedure 1901). In one embodiment, the tilde character marks the presence of a constant in the current line. A check is made to determine if the current line contains a placeholder for a constant in step 1903. If it does, a check is made for the type of constant to insert into the text.

Step 1905 checks if the placeholder is a date. If so, step 1907 checks if the use absolute dates flag is set true, if so, then step 1911 replaces the placeholder with the current absolute date constant. For example, if the prompt is "Only include appointments since ~Date~", the user would see "Only include appointments since 9/1/2019", if the absolute date constant for the tab was 9/1/2019 and the use absolute dates flag was true.

Similarly, if the current date is 1/24/2020 and relative date is set to 365 days and use absolute dates flag is false and prompt is "Only include appointments since ~Date~" then step 1913 calculates the 1/24/2020 minus 365 days is 1/24/2019 and the text the user would see is "Only include appointments since 1/24/2019".

If the constant is of type "quantity of appointments" in step 1915, then that quantity would be substituted in the text as above in step 1917. If the constant is of type "quantity of characters" in step 1919, then that quantity would be substituted in the text in step 1921. If the constant is of type "length of measurement" in step 1923, than that length would be substituted in the text in step 1925.

The use of this example of specific constants is not intended to be interpreted as these are the only constants, or any of these specific constants must be present, or all these constants must be present, or this is the only way to mark the presence of a constant. This is just one non-limiting embodiment of the invention functions.

The display is then updated in step 1909 and the process ends in step 1927.

Figure 25F:
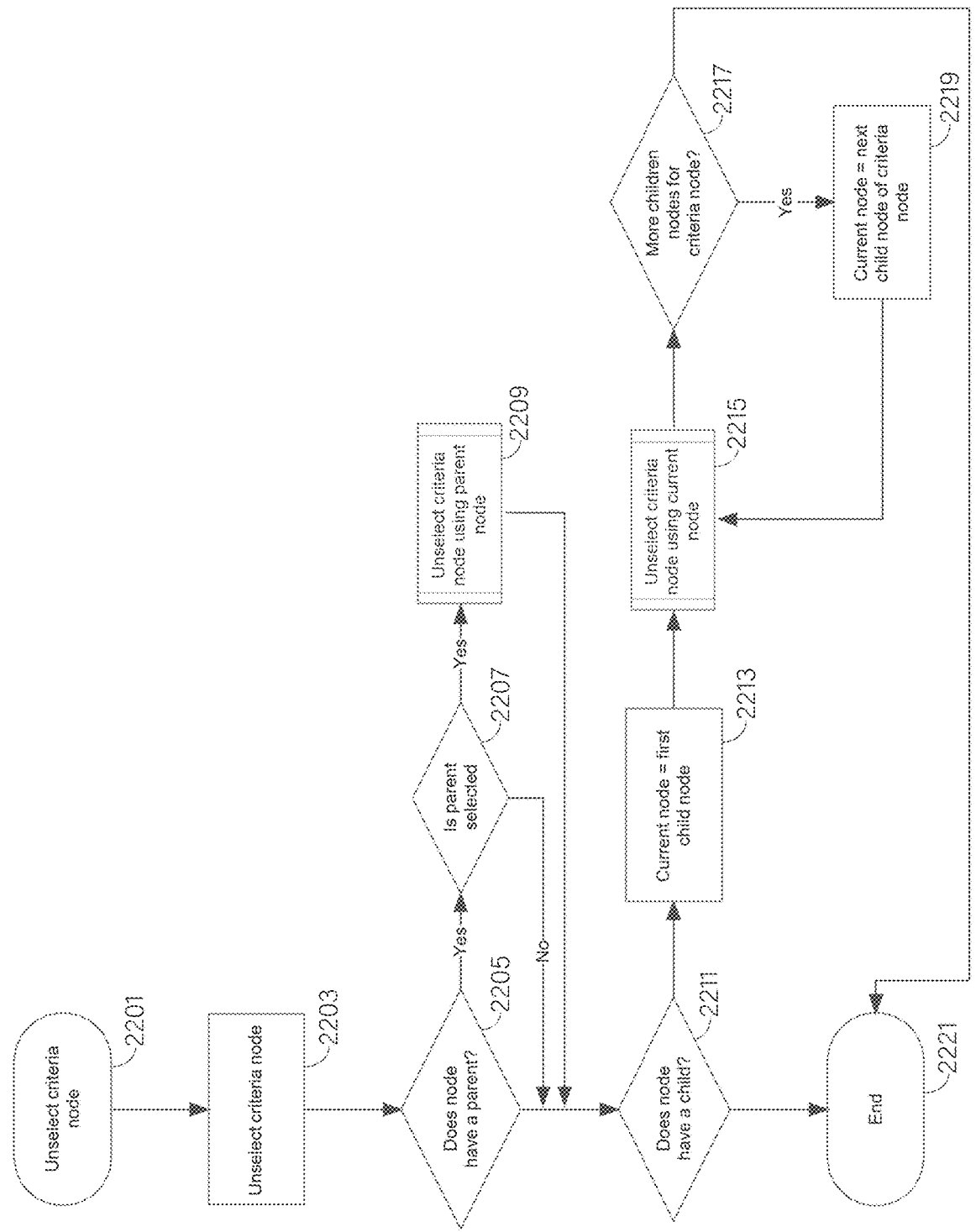
FIG. 25F is a flow diagram depicting an example method of propagating unselecting a tree node to the children and parents of the tree node.

FIG. 25F is a flow diagram depicting an example method of propagating unselecting a tree node to its children and parents (e.g., procedure 2201). Since this function can be recursively called, it starts with the user action to unselect the node in step 2203. A check is made to see if the current node has a parent in step 2205. If so, check if the parent is selected in step 2207. If the parent node is selected, then a recursive call is made to procedure 2201 in step 2209.

Next, the function checks if the current node has children in step 2211. If so, step 2213 sets the current node to the first child node. It then loops through each of the children recursively until there are no more children in steps 2215 through 2219. The loop recursively calls procedure 2201 in step 2215.

The function ends in step 2221.

Figure 25G:
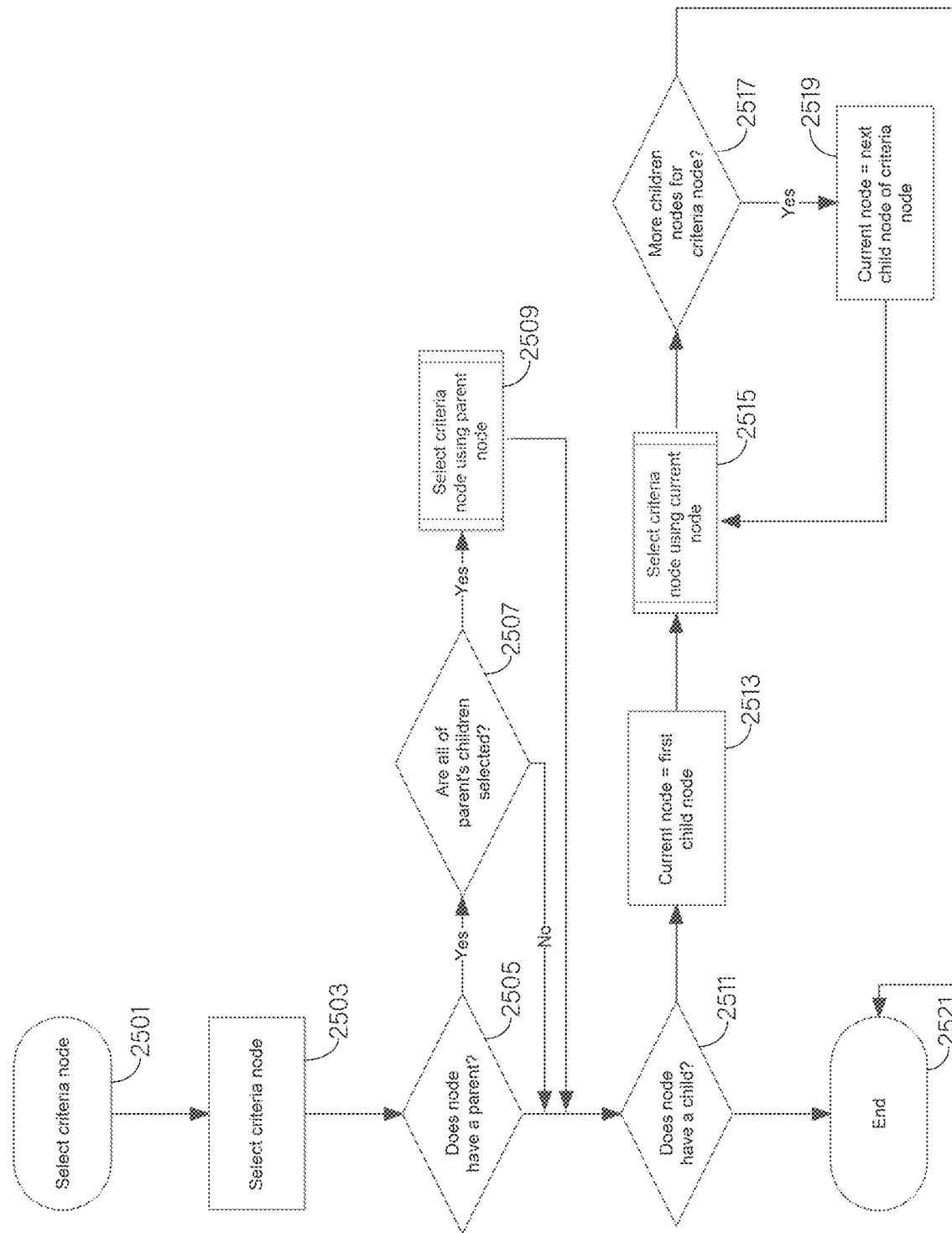
FIG. 25G is a flow diagram depicting an example method of propagating selecting a tree node to the children and parents of the tree node.

FIG. 25G is a flow diagram depicting an example method of propagating selecting a tree node to its children and parents (e.g., procedure 2501). Since this function can be recursively called, it starts with the user action to select the node in step 2503. A check is made to see if the current node has a parent in step 2505. If so, a check is made if all the parent's children are selected in step 2507. If all the parent's children are selected, then a recursive call is made to this same function to select the parent node in step 2509.

Next, the function checks if the current node has children in step 2511. If so, step 2513 sets the current node to the first child node. It loops through each of the children recursively until there are no more children in steps 2515 through 2519. The loop recursively calls procedure 2501 in step 2515.

The function ends in step 2521.

Figure 26:
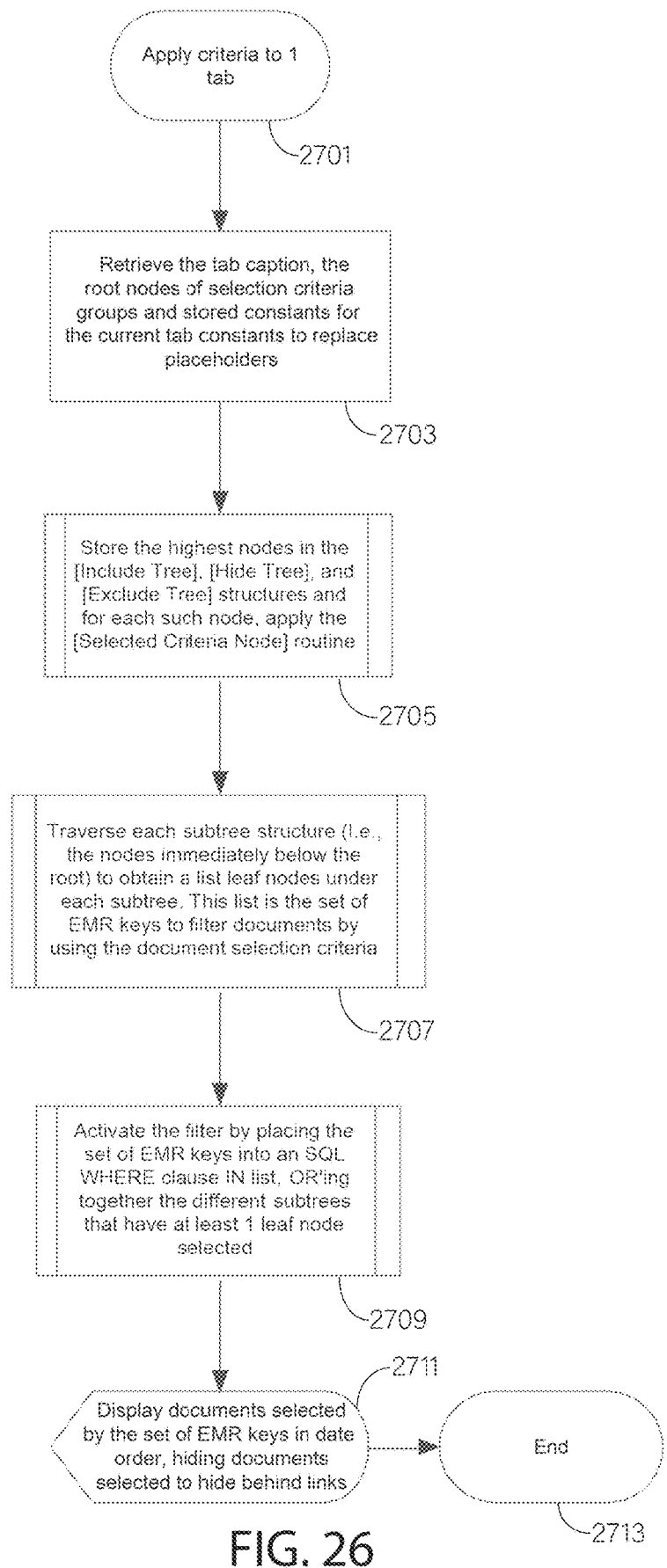
FIG. 26 is a flow diagram depicting an example method of retrieving the document criteria and activating the criteria for each tab to choose the documents to display on a tab.

FIG. 26 shows an overview of how to retrieve the document criteria and activate the criteria for each tab to choose the documents to display on the tab. It starts in step 2701.

There are number of items that should be stored with the tab information describing the appearance of a tab in step 2703. Depending on how the software functions, this information may be retrieved either from program data 4329, or from the data store 43, or some other location the computer has access to, but it will match where step 1811 stored it. This includes the caption of the tab, a list of the root nodes for each subtree selected and the stored constants that apply to that page. The stored contents in one embodiment may include, for example, an absolute date, a quantity of days to calculate a relative date, a quantity of appointments, a quantity of characters and a length of measurement. Certain special case nodes substitute the constant for the placeholder in the caption before displaying the caption, such as a node which states "Hide items more than ~Qty~ appointments old" where the current tab's quantity of appointments is substituted in the caption for the placeholder ~Qty~ before displaying the caption. Similarly, prior to filtering by this criteria, the current value for quantity of appointments on the current tab is substituted into the filtering statement. Another tab may use a totally different value for quantity of appointments. This is at least one reason why the constant values are stored and retrieved for each tab rather than just once for all tabs. The tabs are navigated to by pointing devices 4375 such as a mouse on a screen, pen, trackball, or even a finger or stylus on a touch screen 4377.

The very first time that the program is run, there are two possible options. The first option is that no criteria is selected by default. The second option is that there is some default list of what is initially selected and certain items are selected by default. One item that an embodiment considers hidden by default is to hide detailed test results, such as a mental status inventory questions that a client responded to.

Step 2705 calls procedure 2501 to activate each individual root node for subtrees retrieved in step 2703. The end result of this process is that all the leaf nodes under each subtree root node are also activated. The list of leaf nodes is the list that will be fed to the filter that chooses documents to display in step 2707.

Step 2707 calls procedure 2851 which builds a list of each selected leaf node's tag property; more specifically, in one embodiment, a primary key such as in 3105. These primary keys are concatenated together with commas between them to create a list that can be used by an SQL WHEN . . . IN ( . . . ) type clause.

In step 2709 calls procedure 2801 to build the full SQL WHERE clause.

Finally, the documents which have criteria keys that match the selected leaf nodes are displayed in step 2711. More specifically, the documents that selected by the set of EMR keys may be displayed in an order based on date (e.g., reverse chronological order such that newer documents are on top and older documents are on the bottom). Documents selected to be hidden may be hid behind appropriate placeholders (e.g., links). Once the tab is displayed, there is nothing further to be done in step 2713.

Figure 27A:
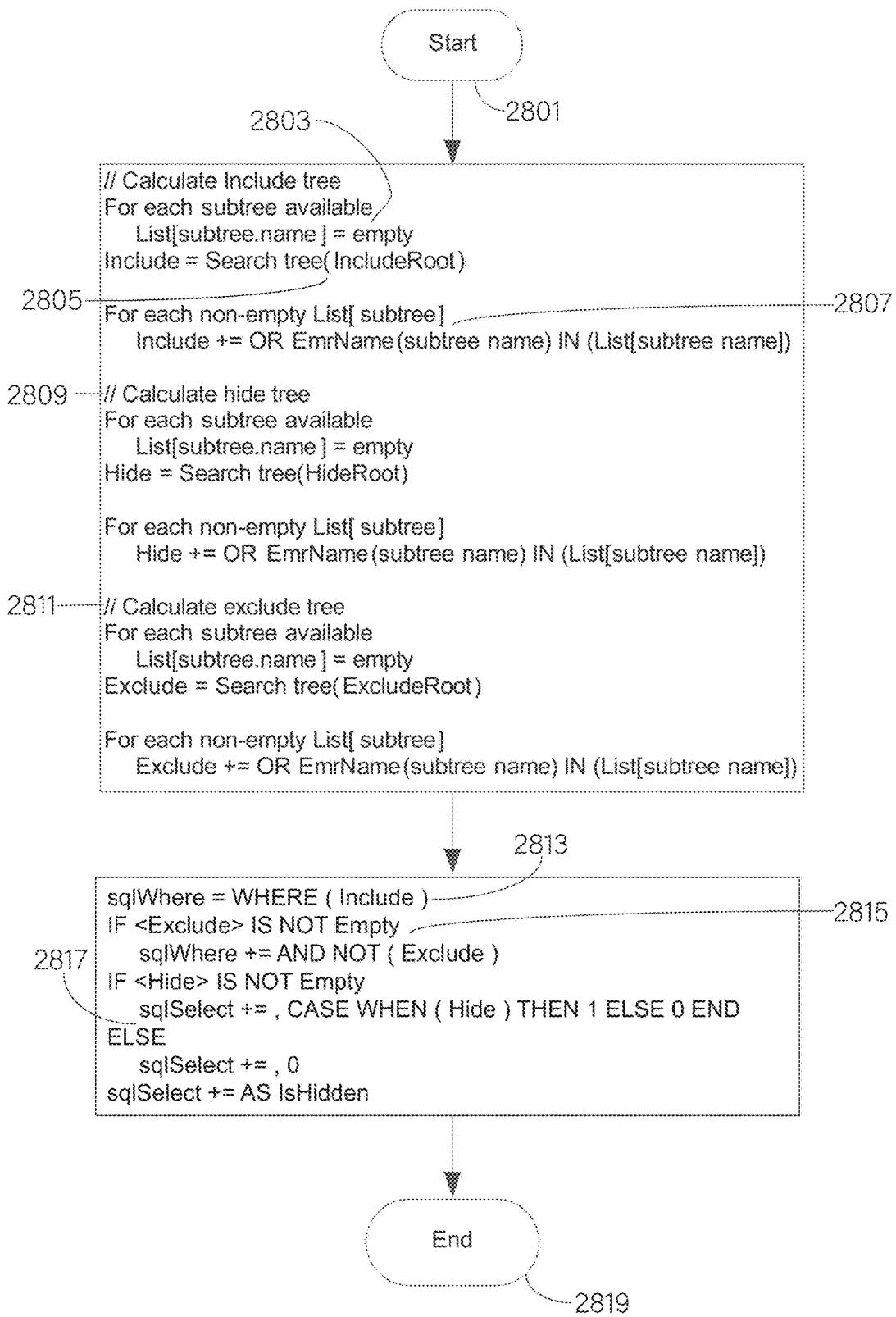
FIG. 27A is a flow diagram depicting an example method of generating SQL clauses from leaf nodes of the configuration trees.

FIG. 27A shows an example of a pseudocode for procedure 2801 of how to generate SQL clauses from leaf nodes of the configuration trees.

The process starts out in loop 2803 by creating an area to store a comma separated list of foreign keys or other values. These will be used for the values in a WHEN . . . IN ( . . . ) statement. In the case of the example of FIG. 29A, the two subtrees are "Appointments" and "Authors" and the manifest constants that represent these two are APPT_TYPE and STAFF, respectively.

In step 2805, a call is made to the function 2851, passing to the function the root of the Include tree. Step 2865 returns a value that needs to be captured which are SQL clauses computed by the special case function 2901.

As an alternative, it would also be possible to pass each immediate subtree of the Include, Hide and Exclude tree separately to procedure 2851, and then only one field in loop 2803 would have been required. (An immediate subtree is the tree that would be the subtree root if all the leaf nodes are selected that have the same manifest constant in FIG. 29A. So, for example, if all the leaf nodes that start "NOTE_TYPE" are selected, you will find that procedure 2501 will also check the box "casenote type". So "casenote type" is an immediate subtree.) This alternate method would have passed the Appointments subtree root and the Authors subtree root to function 2851 for the example tree of FIG. 29A.

Loop 2807 is a loop which accumulates WHEN . . . IN ( . . . ) clauses, OR'ing them together with the special case clauses returned from the same root node. Note, the "+=OR" in this clause is a bit more of a macro than purely a concatenation. If the Include clause is empty, no "OR" will be placed before the rest of the line. Also, if the values being inserted are empty, none of the text is generated. Also, note that the "EmrName(subtree name)" represents a simple function that, given the subtree name parameter, returns the name of the field that must be checked for the corresponding values, typically, a foreign key to some table that is a lookup table for appointments, authors, etc. The EmrName( ) function is commonly written for a specific EMR, but is not included here because that is dependent on the specific EMR to just list foreign key names. The EmrName( ) function would be very much like:

function EmrName(subtreeName)
switch(subtreeName) {
case APPT_TYPE: return "ApptType"; break;
case STAFF: return "StaffId"; break;
case NOTE_TYPE: return "NoteType"; break;}

Steps beginning 2809 to 2811 are exactly the same as above with the exception that HideRoot is referenced instead of the IncludeRoot. Also, steps beginning 2811 are identical with the exception that ExcludeRoot is referenced instead of IncludeRoot.

Step 2813 begins to accumulate the actual SQL WHERE clause by placing the word "WHERE" followed by the contents of the Include variable calculated in the code prior to 2809 inside of parenthesis.

Step 2815 checks if the Exclude variable is empty and, if not, then add the words "AND NOT" and the exclude variable may be added inside of parenthesis.

Finally, Step 2817 checks if the Hide variable is empty. If it is not empty then add an additional variable to the SELECT statement. An example format for doing so may include putting a comma, then the words "CASE WHEN" and the Hide variable contents inside parenthesis followed by the words "THEN 1 ELSE 0 END AS IsHidden". If it is empty, then add a comma and the words "0 AS IsHidden" to the SELECT statement.

Step 2819 is the end of the process.

Figure 27B:
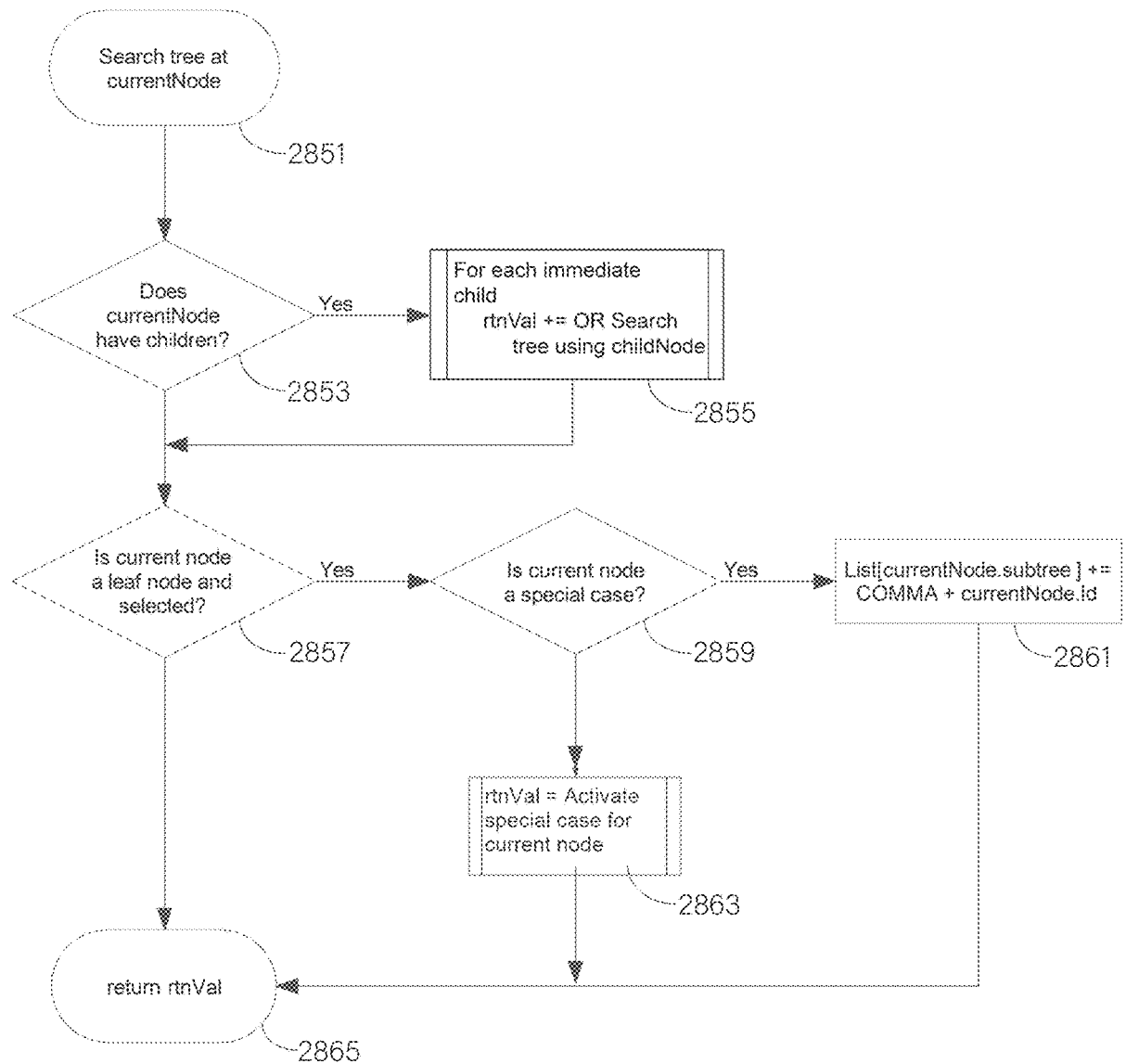
FIG. 27B is a flow diagram depicting an example method of searching a configuration tree to find the selected leaf nodes and collecting required information from those leaf nodes.

FIG. 27B is a flow diagram depicting an example method of searching a configuration tree to find the selected leaf nodes and collecting required information from those leaf nodes (e.g., procedure 2851).

The first step is to recursively call itself with each of its children nodes in steps 2853-2855.

Next, check if the current node is a selected leaf node in step 2857. If not, exit in step 2865. Next, check if the current node is a special case node in step 2859. If it is a special case, then step 2863 calls procedure 2901. Step 2863 stores the value returned from step 2929 for return from this function. If it is not a special case, then accumulate the foreign key stored in the leaf node into the memory prepared for this in step 2803. As was the case with a macro before, the "+=COMMA" macro, only adds a comma if there was a non-empty value in the field before adding the current entry.

The function exits in step 2865.

Figure 28A:
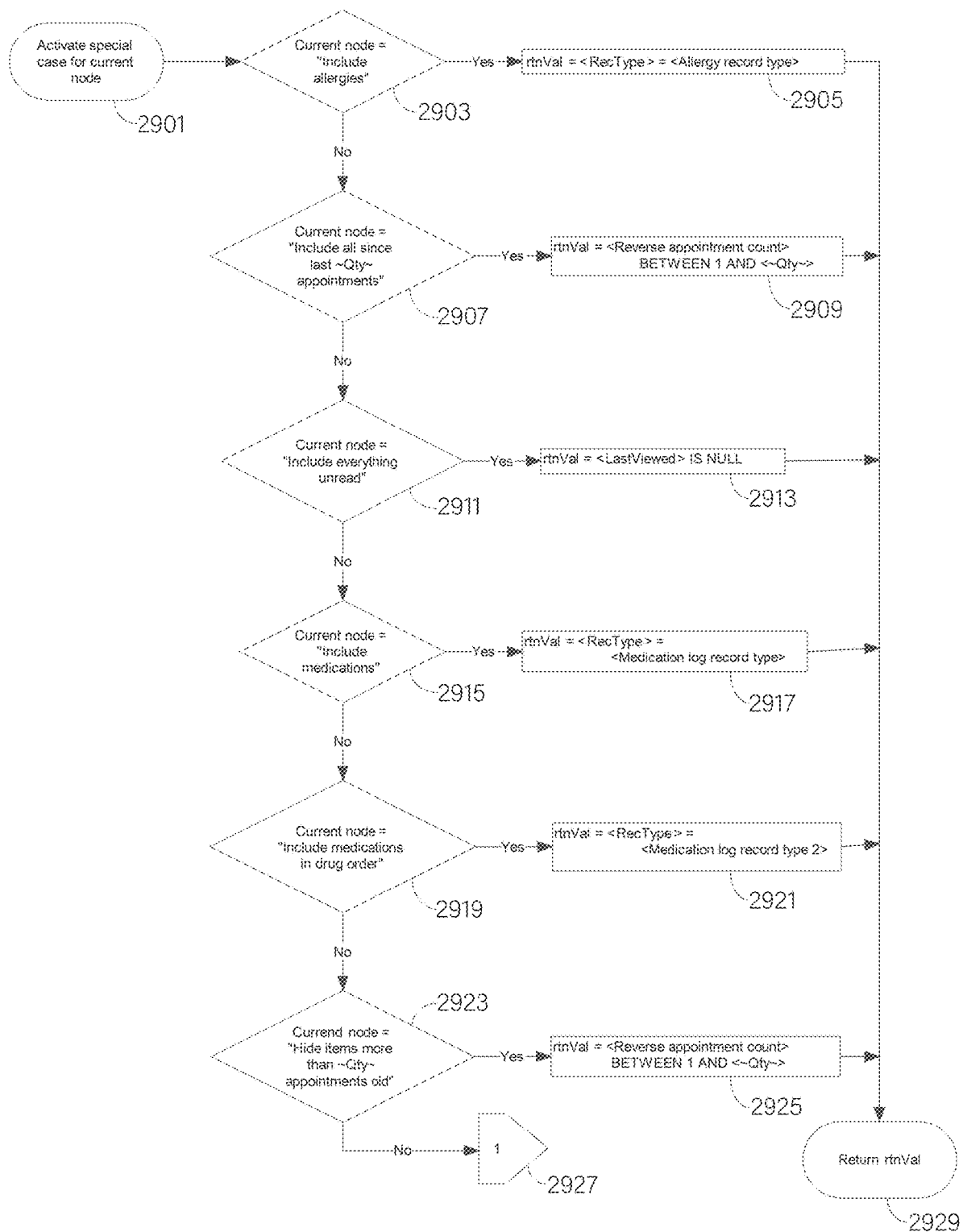
FIG. 28A is a flow diagram depicting the first part of a method of generating SQL clauses from special cases.
Figure 28B:
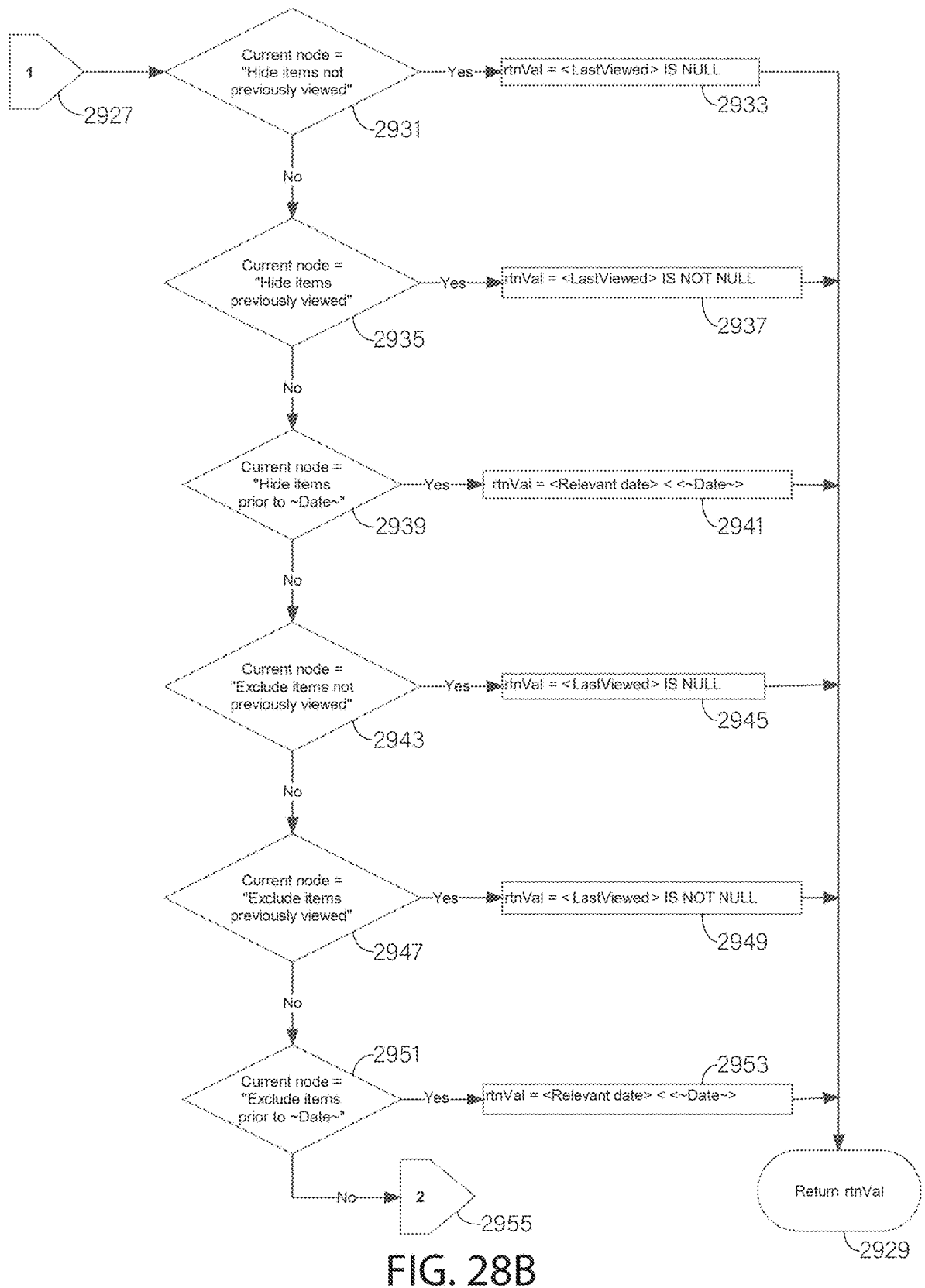
FIG. 28B is a flow diagram depicting the second part of a method of generating SQL clauses from special cases.
Figure 28C:
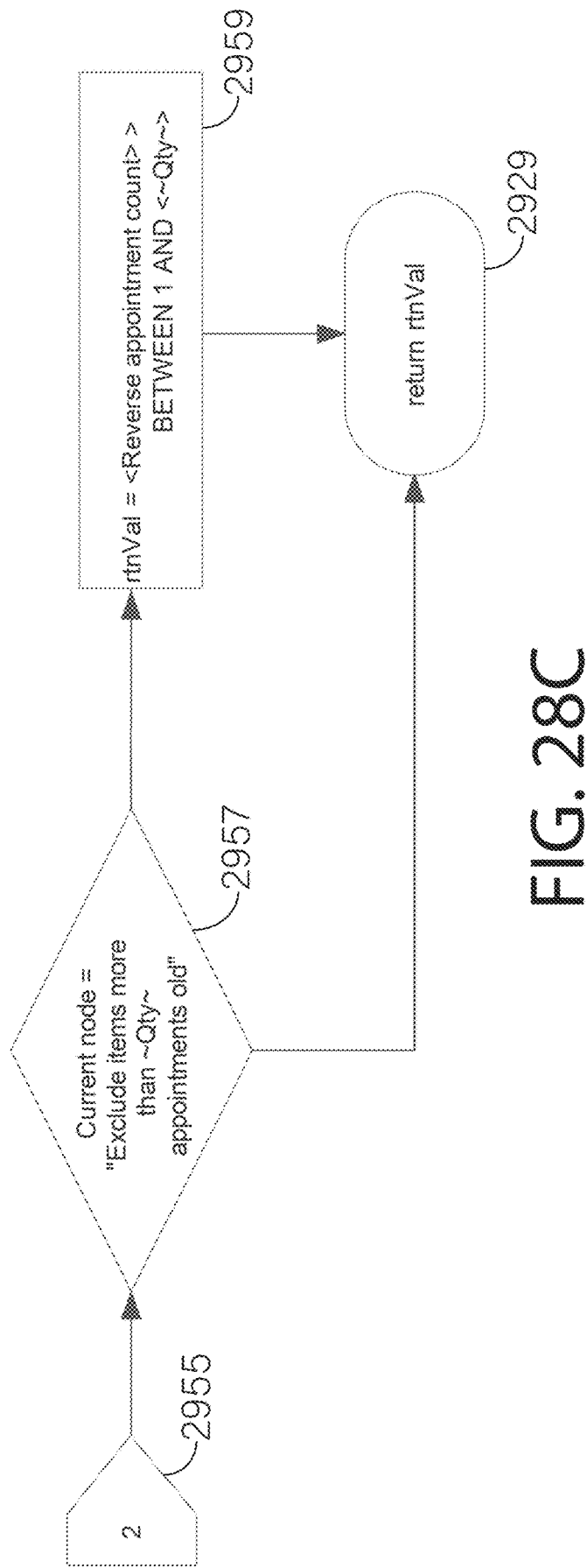
FIG. 28C is a flow diagram depicting the third part of a method of generating SQL clauses from special cases.

FIG. 28A to 28C shows procedure 2901 which generates SQL clauses for one embodiment's special cases. The three pages are one continuous function. The return step 2929 of the procedure is reproduced on each page.

If the current node caption is "Include allergies" in step 2903, then this one may be triggered. Alternatively, the leaf nodes contain a tag property and a negative number 2961 can be used to represent this special case (since that number represents foreign key values and foreign key values for real tables would always be positive) and compare the node's tag property to the constant negative number for this option to trigger it. If triggered, it sets the rtnVal to the RecordType column name, an equals sign, and the RecordType value indicating allergy records in step 2905. Control is then returned to the caller in step 2929.

If the current node caption is "Include all since last ~Qty~appointments" in step 2907, then this one is triggered. Alternatively, compare the node's tag property to a negative number 2963 representing this special case and if the two match, this option is triggered. If triggered, it sets the rtnVal to the ReverseApptCount field name, plus the text BETWEEN<space>1<space>AND<space>, plus value for the tab's quantity of characters in step 2909. Note that the comparison is easily performed by taking the string "Include all since last ~Qty~ appointments" and substituting the tab's quantity of characters for the "~Qty~" first, then perform the comparison against the caption that the user sees on the tab. Control is then returned to the caller in step 2929.

If the current node caption is "Include everything unread" in step 2911, then this one is triggered. Alternatively, compare the node's tag property to a negative number 2965 representing this special case and if the two match, this option is triggered. If triggered, it sets the rtnVal to the LastViewed column name, and the characters "<space>IS<space>NULL" in step 2913. Control is then returned to the caller in step 2929.

If the current node caption is "Include medications" in step 2915, then this one is triggered. Alternatively, compare the node's tag property to a negative number 2967 representing this special case and if the two match, this option is triggered. If triggered, it sets the rtnVal to the RecordType column name, an equals sign, and the RecordType value indicating medication log records in step 2917. Control is then returned to the caller in step 2929.

If the current node caption is "Include medications in drug order" in step 2919, then this one is triggered. Alternatively, compare the node's tag property to a negative number 2969 representing this special case and if the two match, this option is triggered. If triggered, it sets the rtnVal to the RecordType column name, an equals sign, and the RecordType value indicating medication log type 2 records in step 2921. Control is then returned to the caller in step 2929.

If the current node caption is "Hide items more than ~Qty~ appointments old" in step 2923, then this one is triggered. Alternatively, compare the node's tag property to a negative number 2971 representing this special case and if the two match, this option is triggered. If triggered, it sets the rtnVal to the ReverseApptCount field name, plus the text BETWEEN<space>1<space>AND<space>, plus value for the tab's quantity of characters in step 2925. Note that the comparison may easily be performed by taking the string "Hide items more than ~Qty~ appointments old" and substituting the tab's quantity of characters for the "~Qty~" first, then perform the comparison against the caption that the user sees on the tab. Control is then returned to the caller in step 2929.

Step 2927 is the off page connector that connects FIG. 28A to FIG. 28B.

Step 2929 is the end of the function. It returns the rtnVal to step 2863, which, in turn, gets the values concatenated together with ORs using prefix recursion in step 2855 and returned in steps 2865 to 2805 (and its equivalent in steps 2809 and 2811). Of course, it would be a trivial change to use postfix recursion.

If the current node caption is "Hide items not previously viewed" in step 2931, then this one is triggered. Alternatively, compare the node's tag property to a negative number 2973 representing this special case and if the two match, this option is triggered. If triggered, it sets the rtnVal to the LastViewed column name, and the characters "<space>IS<space>NULL" in step 2933. Control is then returned to the caller in step 2929.

If the current node caption is "Hide items previously viewed" in step 2935, then this one is triggered. Alternatively, compare the node's tag property to a negative number 2975 representing this special case and if the two match, this option is triggered. If triggered, it sets the rtnVal to the LastViewed column name, and the characters "<space>IS<space>NOT<space>NULL" in step 2937. Control is then returned to the caller in step 2929.

If the current node caption is "Hide items prior to ~Date~" in step 2939, then this one is triggered. Alternatively, compare the node's tag property to a negative number 2977 representing this special case and if the two match, this option is triggered. If triggered, it sets the rtnVal to the RelevantDate field name, plus the less than sign, plus value for the tab's (absolute or relative; the decision of which is determined by flag "use absolute dates") date field in step 2941. Note that the comparison is easily performed by taking the string "Hide items prior to ~Date~" and substituting the tab's date for the "~Date~" first, then perform the comparison against the caption that the user sees on the tab. Control is then returned to the caller in step 2929.

If the current node caption is "Exclude items not previously viewed" in step 2943, then this one is triggered. Alternatively, compare the node's tag property to a negative number 2979 representing this special case and if the two match, this option is triggered. If triggered, it sets the rtnVal to the LastViewed column name, and the characters "<space>IS<space>NULL" in step 2945. Control is then returned to the caller in step 2929.

If the current node caption is "Exclude items previously viewed" in step 2947, then this one is triggered. Alternatively, compare the node's tag property to a negative number 2981 representing this special case and if the two match, this option is triggered. If triggered, it sets the rtnVal to the LastViewed column name, and the characters "<space>IS<space>NOT<space>NULL" in step 2949. Control is then returned to the caller in step 2929.

If the current node caption is "Exclude items prior to ~Date~" in step 2951, then this one is triggered. Alternatively, compare the node's tag property to a negative number 2983 representing this special case and if the two match, this option is triggered. If triggered, it sets the rtnVal to the RelevantDate field name, plus the less than sign, plus value for the tab's (absolute or relative; the decision of which is determined by flag "use absolute dates") date field in step 2953. Note that the comparison is easily performed by taking the string "Exclude items prior to ~Date~" and substituting the tab's date for the "~Date~" first, then perform the comparison against the caption that the user sees on the tab. Control is then returned to the caller in step 2929.

Step 2955 is the off page connector that connects FIG. 28B to FIG. 28C.

If the current node caption is "Exclude items more than ~Qty~ appointments old" in step 2957, then this one is triggered. Alternatively, compare the node's tag property to a negative number 2985 representing this special case and if the two match, this option is triggered. If triggered, set the rtnVal to the ReverseApptCount field name, plus the text BETWEEN<space>1<space>AND<space>, plus value for the tab's quantity of characters in step 2959. Note that the comparison is easily performed by taking the string "Exclude items more than ~Qty~ appointments old" and substituting the tab's quantity of characters for the "~Qty~" first, then perform the comparison against the caption that the user sees on the tab. Control is then returned to the caller in step 2929.

FIG. 28D shows an example of a pseudocode for an alternate method of generating SQL clauses from the single integer value currNodeTagNo. The variable currNodeTagNo represents the current node's tag value.

FIG. 29A shows an example of a simple Include configuration tree. This tree could have been completed by selecting node 3101 and node 3103. This tree can be completely described by listing the path to the two subtree roots (Include|Appointments|Psychiatry;Include|Authors|Psychiatry). In one embodiment, this is an example of the string stored in 1811 and retrieved in step 2703 for the root nodes. There is no need to store any leaf nodes, in this case.

The box 3105 and 3107 are pointing to is not visible to the user. This box represents the tag property of the leaf nodes. The leaf nodes are the only items searched for when filtering data. In this case, the all cap words, "APPT_TYPE" and "STAFF", represent manifest constants and are used to look up the column names that contain foreign keys to a table that contains details of appointments and staff. The appointments table would contain such items as the appointment name and the default length of the appointment. The staff table would contain such items as the staff member's first and last name and possibly whether that staff member is able to prescribe medications in the EMR. When I say foreign key, there is no requirement that the program have access to the table being pointed to, just that there is some unique value that points to the table. Nothing further needs to be looked up in the EMR data store. In one embodiment, the data has all been extracted from the EMR and placed into a data extract table for the current appointment and these values are just a column of the extract table. If the value in the column matches what is in the extract table, that row of the table is included. For this specific example, suppose the foreign key to appointment table is ApptType and the foreign key to the staff table is Staff Id. Whenever the ApptType column has any of the values in the circle 3105 (i.e., 131 or 140), that row of information should be included on the screen display for the tab. Also, whenever the Staff Id column has any of the values in the circle 3107 (i.e., 225, 218 or 140), that row of information should be included on that tab also.

FIG. 29B shows an example of a hide configuration tree. Note that structure of this tree is nearly identical to FIG. 29A with the only differences being what appears under the "Other" subtree and the top level nodes ("Include" and "Hide"). Even when some of the lines in the "Other" subtree are similar, they should still be custom worded for the "Other" subtree rather than identical.

In this case the leaf node 3301 is checked. The casenote table contains such items as the name of the casenote. For this example, assume the foreign key to the casenote table stored in the extract table is NoteTypeId. Because the value in circle 3303 is 157, whenever NoteTypeId is 157, any data that otherwise would have been placed on the screen, needs to be initially hidden, such as behind a button 3901 or other link for the whole hidden document.

FIG. 29C shows an example of an exclude configuration tree. In this case, only the leaf node 3801 is checked. Notice that the text on that line with "~Qty~" never appears on the screen for the user. If the quantity of appointments is 4 then the actual message that would appear on the screen is "Exclude items more than 4 appointments old". One way to match text is to substitute the current value for ~Qty~ (i.e., 4) into the string "Exclude items more than ~Qty~appointments old", making it "Exclude items more than 4 appointments old", then compare the string with the caption of each selected node. The alternative way to identify the special cases discussed in step 2907 is shown in circle 3803, so it can be as easy as comparing the tag property value to −15 to identify this special case. That value could then be run through the pseudocode in FIG. 28D to obtain the SQL clause "ReverseApptCnt>4" (assuming that the current tab has a value of 4 for the variable "~Qty~").

Figure 29D:
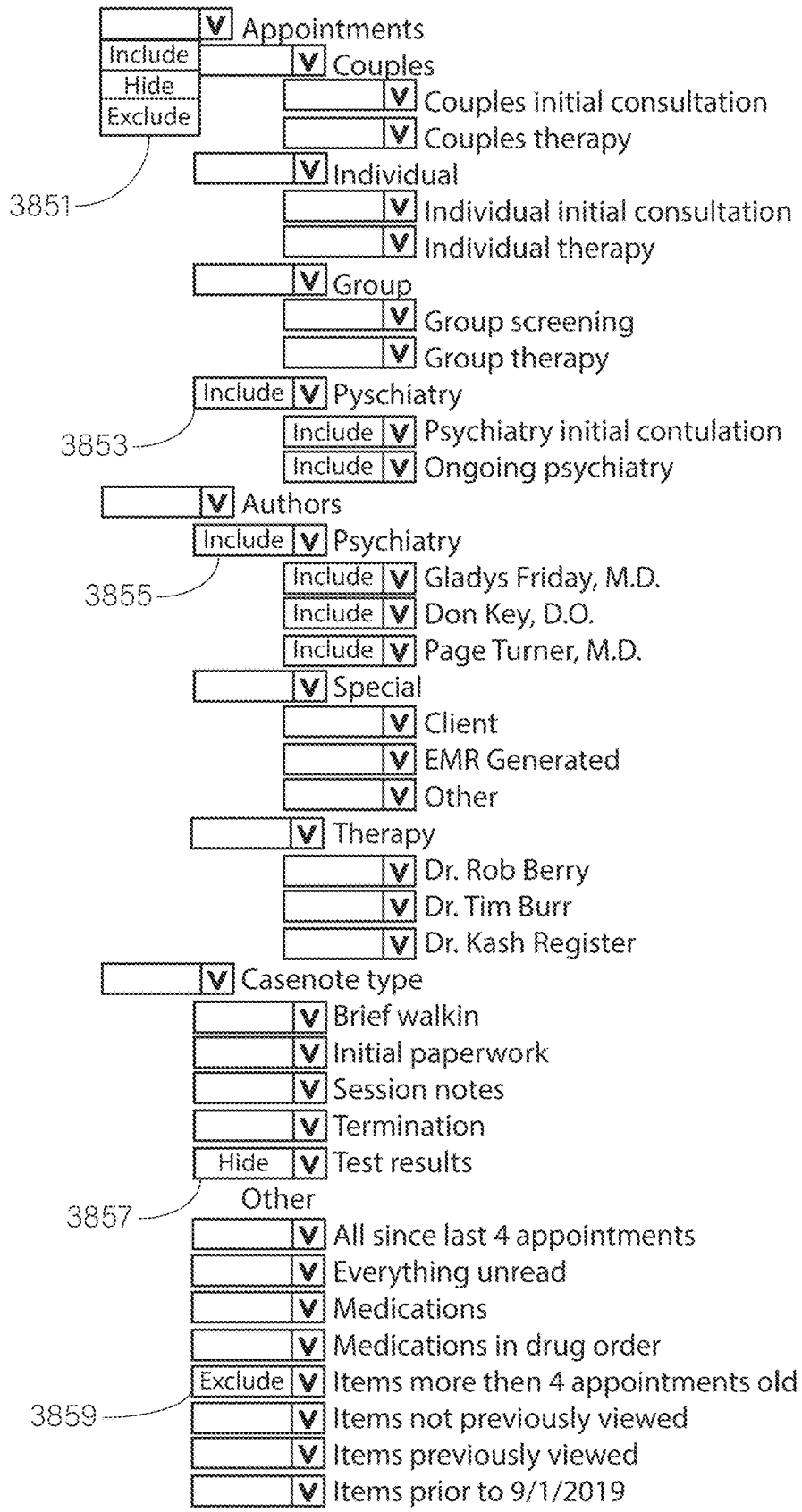
FIG. 29D is an example of a configuration tree that may be an alternative to the configuration trees of FIGS. 29A-29C.

FIG. 29D shows an alternate embodiment to FIG. 29A-29C setting up the identical case. Combo box 3851 is shown expanded to make clear how this tree is filled out. There is a similar combo box with the three options available at every node with the possible exceptions of the root node and the "Other" node. The most that would make sense at the root node would be to include the options "Include" and "Hide" (because it would be meaningless to exclude everything—that would just be a blank page associated with a tab).

Just like FIG. 29A, combo box 3853 and combo box 3855 only need be set to "Include" to set all the leaf nodes that are required for this example. Just like FIG. 29B, only the combo box 3857 needs to be set to "Hide". Like FIG. 29C, only the combo box 3859 needs to be set to "Exclude".

To program this embodiment, there are some obvious differences that would be apparent to anyone skilled in the art after reading this disclosure.

A node selected to "hide" has an implied value that the node is also selected to "include".

The propagating of values to the parent and child nodes also changes.

Propagation is done not just on parent and child paths, but on a priority system along those paths. The top priority is an Exclude. The middle priority is a Hide. And the lowest priority is an Include. Only higher priority nodes can overwrite lower priority nodes when propagating.

Care has to be taken when a node that was set to a non-blank value (either include, hide or exclude) is changed to a blank value, the current node has to inherit its parent value and propagates the new value to all of its children. If all the siblings of the parent all match the parent node, the grandfather node also gets recursively set to the parent's value.

FIG. 30 shows an example of a SQL generated for the configuration trees of FIG. 29A-29C using the methods of FIGS. 27 and 28.

Figure 31:
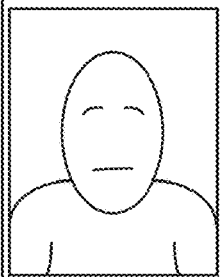
FIG. 31 is an example of two data forms being presented in the context of a tablet computer in accordance with step 2711 of the method of FIG. 26.

FIG. 31 shows an example of the appearance of some elements of an embodiment of the present invention in the context of a tablet computer.

Button 3901 shows an example of a hidden document as a result of the user configuring a document type to hide, like node 3301. For example, if this button hid the client's answers to a psychological inventory, because, in normal practice, one may only want to refer to the computer generated graphs and numerical computed values. However, if someone wanted to drill down to specific questions and answers they could by pressing this button.

Pure text 3903 shows the results of a multi-select check box, as in FIG. 6C.

Heading 3905, is an example of shortening a heading, as in FIG. 11. As in 1409, the full text of the heading was "Please provide the names and relationships of additional family members starting with step parents, siblings, spouse/partner, children." The original heading would have taken 2 lines to display.

Figure 32:
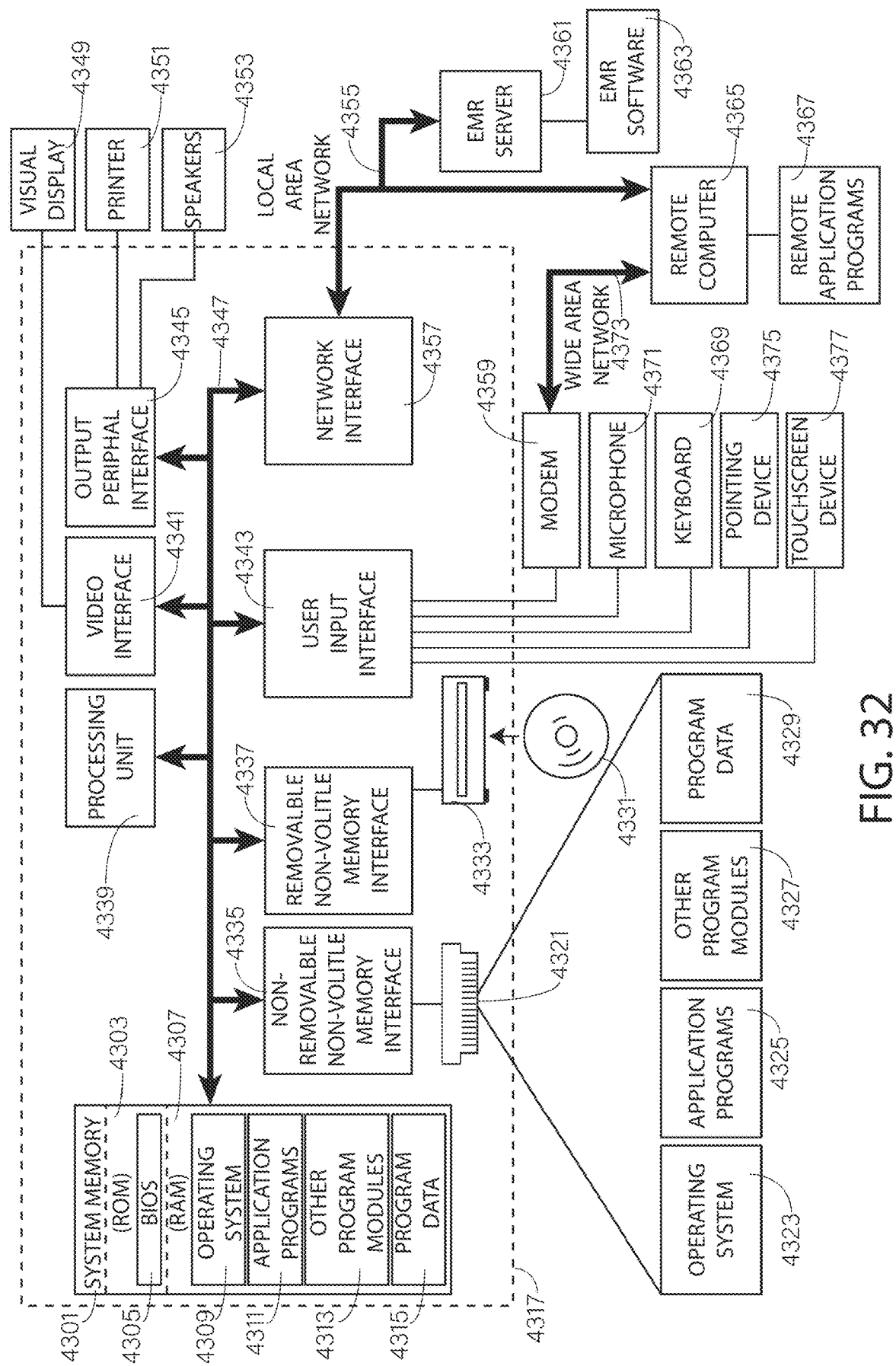
FIG. 32 shows a block diagram of one example of a computing environment.

FIG. 32 is one embodiment of a computing environment in which system 75, or parts of it, (for example) can be deployed. With reference to FIG. 32, an exemplary system for implementing some embodiments includes a general-purpose computing device in the form of a computer 4317. Components of computer 4317 may include, but are not limited to, a processing unit 4339 (which can comprise processor 42), a system memory 4301, and a system bus 4347 that couples various system components including the system memory to the processing unit 4339. The system bus 4347 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. Memory and programs described with respect to FIG. 1 can be deployed in corresponding portions of FIG. 32.

Computer 4317 typically includes a variety of computer readable media. Computer readable media can be any available media that can be accessed by computer 4317 (e.g., for storing and retrieving one or more document criteria) and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 4317. Communication media typically embodies computer readable instructions, data structures, program modules or other data in a transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 4301 includes computer storage media in the form of volatile and/or nonvolatile memory such as read only memory (ROM) 4303 and random access memory (RAM) 4307. A basic input/output system 4305 (BIOS), containing the basic routines that help to transfer information between elements within computer 4317, such as during start-up, is typically stored in ROM 4303. RAM 4307 typically contains data and/or program modules that are immediately accessible to and/or presently being operated on by processing unit 4339. By way of example, and not limitation, FIG. 32 illustrates operating system 4309, application programs 4311, other program modules 4313, and program data 4315.

The computer 4317 may also include other removable/non-removable volatile/nonvolatile computer storage media. By way of example only, FIG. 32 illustrates a solid state RAM drive 4321 that reads from or writes to non-removable, nonvolatile magnetic media, and an optical disk drive 4333 that reads from or writes to a removable, nonvolatile optical disk 4331 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, hard drive, solid state ROM, and the like. The solid state RAM drive (SSD) 4321 is typically connected to the system bus 4347 through a non-removable memory interface such as interface 4335, and optical disk drive 4333 are typically connected to the system bus 4347 by a removable memory interface, such as interface 4337.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The drives and their associated computer storage media discussed above and illustrated in FIG. 32, provide storage of computer readable instructions, data structures, program modules and other data for the computer 4317. In FIG. 32, for example, solid state RAM drive 4321 is illustrated as storing operating system 4323, application programs 4325, other program modules 4327, and program data 4329. Note that these components can either be the same as or different from operating system 4309, application programs 4311, other program modules 4313, and program data 4315.

Operating system 4323, application programs 4325, other program modules 4327, and program data 4329 are given different numbers here to illustrate that, at a minimum, they are different copies.

A user may enter commands and information into the computer 4317 through input devices such as a keyboard 4369, a microphone 4371, a pointing device 4375 such as a mouse, trackball or touch pad, and a touchscreen 4377. Other input devices (not shown) may include a joystick, game pad, satellite dish, scanner, or the like. These and other input devices are often connected to the processing unit 4339 through a user input interface 4343 that is coupled to the system bus, but may be connected by other interface and bus structures, such as a parallel port, game port or a universal serial bus (USB). A visual display 4349 or other type of display device is also connected to the system bus 4347 via an interface, such as a video interface 4341. In addition to the monitor, computers may also include other peripheral output devices such as speakers 4353 and printer 4351, which may be connected through an output peripheral interface 4345.

The computer 4317 is operated in a networked environment using logical connections to one or more remote computers, such as a remote computer 4365 and an EMR Server 4361. The remote computer 4365 may be a personal computer, a hand-held device, a server, a router, a network PC, a peer device or other common network node, and typically includes many or all of the elements described above relative to the computer 4317. The EMR server 4361 is an example of the remote computer 4365 and houses a data store and EMR software 4363. The logical connections depicted in FIG. 32 include a local area network (LAN) 4355 and a wide area network (WAN) 4373, but may also include other networks. Such networking environments are commonplace in offices, enterprise-wide computer networks, intranets and the Internet.

When used in a LAN networking environment, the computer 4317 is connected to the LAN 4355 through a network interface or adapter 4357. When used in a WAN networking environment, the computer 4317 typically includes a modem 4359 or other means for establishing communications over the WAN 4373, such as the Internet. The modem 4359, which may be internal or external, may be connected to the system bus 4347 via the user input interface 4343, or other appropriate mechanism. In a networked environment, program modules depicted relative to the computer 4317, or portions thereof, may be stored in the remote memory storage device. By way of example, and not limitation, FIG. 32 illustrates remote application programs 4367 as residing on remote computer 4365. It will be appreciated that the network connections shown are exemplary and other means of establishing a communications link between the computers may be used.

Figure 33:
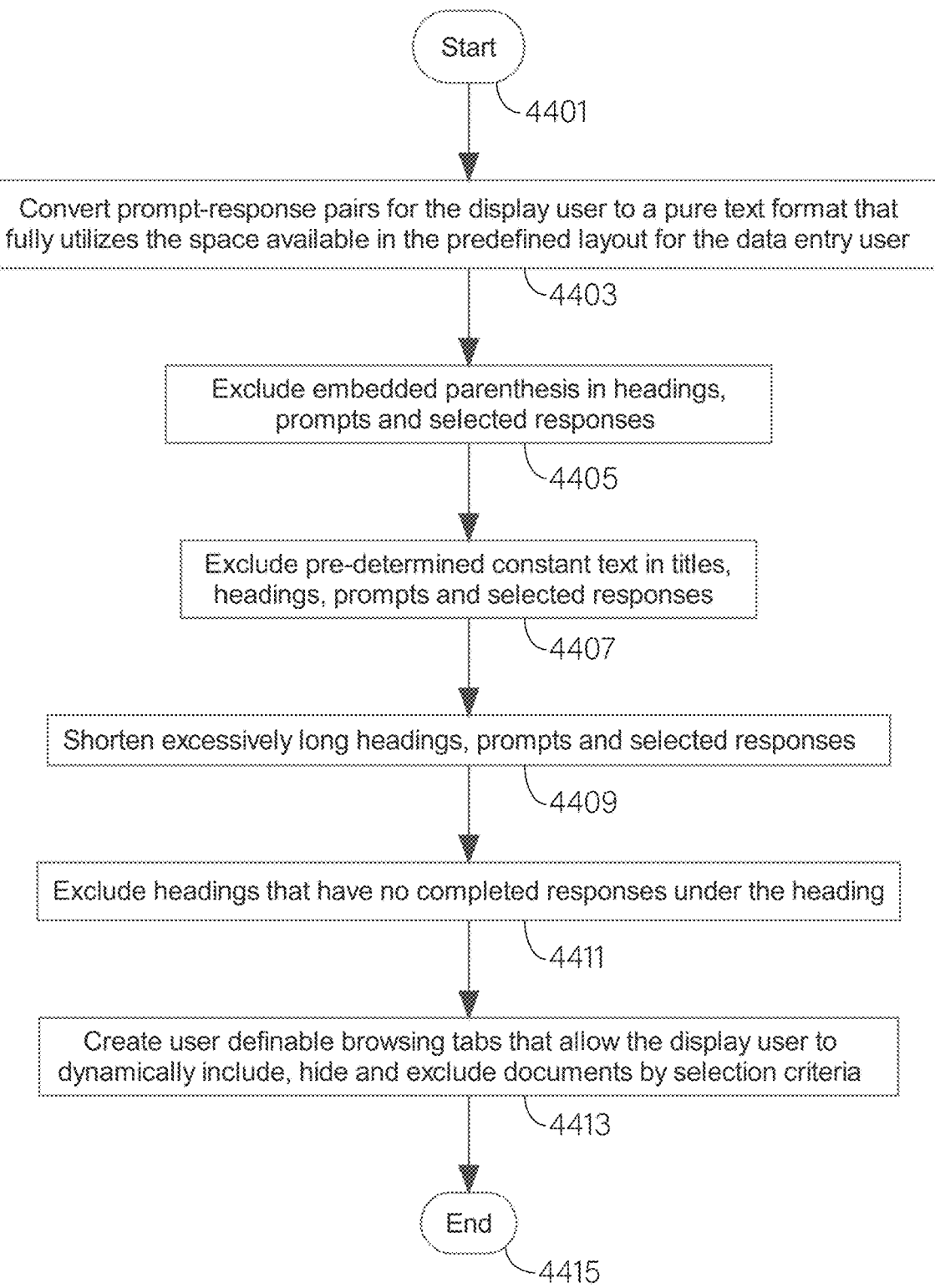
FIG. 33 is a flow diagram depicting the various methods of the present disclosure.

FIG. 33 is an example summary of known embodiments of the invention. This invention disclosure was written with the idea of most of these techniques are able to stand independently, but more powerful work can be done by combining the techniques. The process starts with step 4401.

Step 4403 is the most basic technique and it involves converting both prompts and responses to pure text, combining them with user defined strings, formatting the titles, headings, prompts and responses with user defined formats and place them back on the screen in the same horizontal width allowed defined by the left boundary of the prompt and right boundary of the response. This is covered in FIGS. 3-8.

Step 4405 excludes embedded parentheses in headings, prompts and selected responses. The selected responses eligible for this technique are any other than those typed by the data entry user and those which are computed responses. This is covered in FIGS. 9-18.

Step 4407 excludes certain constant text that is predetermined to never be useful to the display user, such as a prefix "OBSOLETE:" to mark certain titles, headings and prompts as no longer active in the form design area of the data store of the EMR system. This is covered in 904 of FIG. 11.

Step 4409 shortens excessively long headings, prompts and selected responses. The selected responses eligible for this technique are any other than those typed by the data entry user and those which are computed responses. This is covered in FIGS. 11-18.

Step 4411 excludes headings that are no longer necessary based on which responses the data entry user did not complete. This is covered in FIGS. 19-23.

Step 4413 separates the documents that make up a client chart into separate user definable tabs so that the information the display user is seeking is easier to find as there are fewer criteria on a tab. Configuring the tabs is covered in FIG. 25. Browsing the tabs is covered in FIGS. 24, and 26-31.

The process ends with step 4415.

What is claimed is:

1. A method for displaying a plurality of documents on a screen, said plurality of documents comprising an electronic medical record, wherein each document of said plurality of documents defines a plurality of document criteria based on the substance of said documents, at least one document criterion of said plurality of document criteria comprising a date, said screen comprising a plurality of display tabs, said method comprising:
   selecting a first document criterion;
   selecting a second document criterion;
   storing said first document criterion and said second document criterion on a computer readable medium;
   retrieving said first document criterion and said second document criterion from said computer readable medium;
   filtering said plurality of documents based on said first document criterion to yield a first plurality of filtered documents, wherein each filtered document of said first plurality of filtered documents comprises a plurality of document criteria that comprises said first document criterion, wherein at least one filtered document of said first plurality of filtered documents comprises at least one of a title, a heading, a prompt, and a response related to said prompt, wherein each title, heading, prompt, and response defines a left boundary and a right boundary, wherein said at least one filtered document of said first plurality of filtered documents comprises a group of filtered documents, each filtered document of said group of filtered documents comprises at least one of a normal heading and a terminal heading, said normal heading is not followed by at least one of a prompt and a response, said terminal heading is followed by at least one of another terminal heading and the end of a filtered document of said group of filtered documents;
   identifying said normal headings and said terminal headings of said group of filtered documents;
   excluding said normal headings and said terminal headings when displaying said filtered documents of said group of filtered documents on said display tab;

filtering said plurality of documents based on said second document criterion to yield a second plurality of filtered documents, wherein each filtered document of said second plurality of filtered documents comprises a plurality of document criteria that comprises said second document criterion;
generating a placeholder for each filtered document of said second plurality of filtered documents;
selecting a tab from said plurality of tabs; and displaying said first plurality of filtered documents and each generated placeholder on said tab in a sequential order that is based on said date for each document of said plurality of documents.

2. The method of claim 1 further comprising:
selecting a third document criterion;
storing said third document criterion on said computer readable medium;
filtering said plurality of documents based on said third document criterion to yield a third plurality of filtered documents, wherein each filtered document of said third plurality of filtered documents comprises a plurality of document criteria that comprises said third document criterion; and
generating a placeholder for each filtered document of said third plurality of filtered documents.

3. The method of claim 1 wherein at least one of said first document criterion and said second document criterion is selected from a default list of selectable document criteria.

4. The method of claim 1 wherein said at least one filtered document of said first plurality of filtered documents comprises a filtered document comprising a prompt but no response, said method further comprising excluding said prompt when displaying said filtered document on said display tab.

5. The method of claim 1 wherein: said at least one filtered document of said first plurality of filtered documents comprises a filtered document comprising a prompt and a response; said left boundary of said prompt of said filtered document is the furthest-left boundary; said right boundary of said response of said filtered document is the furthest-right boundary; said furthest-left boundary and said furthest-right boundary collectively define a pair of absolute boundaries; and said method further comprising: reproducing said prompt to yield a reproduced prompt;
converting said response into pure text to yield a converted response; combining said reproduced prompt and said converted response to form a prompt-response pair; and
replacing said prompt and said response of said filtered document with said prompt-response pair while remaining within said absolute boundaries.

6. The method of claim 5 wherein said reproducing said prompt comprises formatting said reproduced prompt in a different font than said converted response.

7. The method of claim 5 wherein said converting said response comprises shortening said response such that said converted response does not exceed a pre-determined length.

8. The method of claim 7 wherein said pre-determined length is measured in number of characters.

9. The method of claim 7 wherein said pre-determined length is measured using at least one of the Imperial system of measurement and the Metric system of measurement.

10. A method for selectively displaying elements from a plurality of documents on a screen, wherein each document of said plurality of documents comprises at least one element, said elements comprising at least one of a title, a heading, a prompt, and a response related to a prompt, wherein each title, heading, prompt, and response defines a left boundary and a right boundary, said plurality of documents comprising a first document comprising a prompt but no response, said plurality of documents further comprising a second document comprising a prompt and a response, wherein said left boundary of said prompt of said second document is the furthest-left boundary; wherein said right boundary of said response of said second document is the furthest-right boundary, wherein said furthest-left boundary and said furthest-right boundary collectively define a pair of absolute boundaries, wherein said plurality of documents comprises a group of documents, wherein each document of said group of documents includes at least one of a normal heading and a terminal heading, wherein said normal heading is not followed by at least one of a prompt and a response, wherein said terminal heading is followed by at least one of another terminal heading and the end of a filtered document of said group of filtered documents, said method comprising:
identifying said normal headings and said terminal headings of said group of filtered documents;
displaying said group of documents on said screen, said displaying said group of documents comprising excluding said normal headings and said terminal headings;
reproducing said prompt of said second document to yield a reproduced prompt;
converting said response of said second document into pure text to yield a converted response;
combining said reproduced prompt and said converted response to form a prompt-response pair; and
displaying said first document and said second document on said screen, said displaying comprising replacing said prompt and said response of said second document with said prompt-response pair while remaining within said absolute boundaries; said displaying further comprising excluding said prompt of said first document when displaying said first document on said screen.

11. The method of claim 10 wherein said converting said response comprises excluding at least one of embedded parentheses and parenthetical comments from said converted response.

12. The method of claim 10 wherein said converting said responses comprises excluding constant text from said converted response.

13. The method of claim 10 wherein said converting said response comprises shortening said response such that said converted response does not exceed a pre-determined length.

14. The method of claim 13 wherein said pre-determined length is measured in number of characters.

15. The method of claim 13 wherein said pre-determined length is measured using at least one of the Imperial system of measurement and the Metric system of measurement.

16. A method for displaying a plurality of documents on a screen, said plurality of documents comprising an electronic medical record, wherein each document of said plurality of documents defines a plurality of document criteria based on the substance of said documents, at least one document criterion of said plurality of document criteria comprising a date, said screen comprising a plurality of display tabs, said method comprising:
selecting a first document criterion;
selecting a second document criterion;
storing said first document criterion and said second document criterion on a computer readable medium;

retrieving said first document criterion and said second document criterion from said computer readable medium;

filtering said plurality of documents based on said first document criterion to yield a first plurality of filtered documents, wherein each filtered document of said first plurality of filtered documents comprises a plurality of document criteria that comprises said first document criterion, each filtered document of said first plurality of filtered documents further comprising at least one of a prompt and a response related to a prompt, said first plurality of filtered documents comprising a filtered document comprising a prompt but no response, said first plurality of filtered documents further comprising a group of filtered documents, wherein each filtered document of said group of filtered documents comprises at least one of a normal heading and a terminal heading, wherein said normal heading is followed by at least one of a prompt and a response, and wherein said terminal heading is followed by at least one of another terminal heading and the end of a filtered document of said group of filtered documents;

identifying said normal headings and said terminal headings of said group of filtered documents;

filtering said plurality of documents based on said second document criterion to yield a second plurality of filtered documents, wherein each filtered document of said second plurality of filtered documents comprises a plurality of document criteria that comprises said second document criterion;

generating a placeholder for each filtered document of said second plurality of filtered documents;

selecting a tab from said plurality of tabs; and displaying said first plurality of filtered documents and each generated placeholder on said tab in a sequential order that is based on said date for each document of said plurality of documents, wherein said displaying comprises excluding said prompt of said filtered document, said normal headings of said group of filtered documents, and said terminal headings of said group of filtered documents from said display tab.

17. A tangible, non-transitory, computer-readable medium storing program instructions that cause a computer to execute the method of claim 1.

18. A tangible, non-transitory, computer-readable medium storing program instructions that cause a computer to execute the method of claim 10.

19. A tangible, non-transitory, computer-readable medium storing program instructions that cause a computer to execute the method of claim 16.

* * * * *